US012704520B2

(12) United States Patent
Cho et al.

(10) Patent No.: US 12,704,520 B2
(45) Date of Patent: Aug. 11, 2026

(54) MELANOGENESIS DETECTION METHOD USING FAM86A

(71) Applicant: Research & Business Foundation Sungkyunkwan University, Suwon-si (KR)

(72) Inventors: Jae Youl Cho, Suwon-si (KR); Yo Han Hong, Goyang-si (KR); Sang Hee Park, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 1216 days.

(21) Appl. No.: 17/635,294

(22) PCT Filed: Aug. 14, 2020

(86) PCT No.: PCT/KR2020/095119

§ 371 (c)(1),
(2) Date: Feb. 14, 2022

(87) PCT Pub. No.: WO2021/034179

PCT Pub. Date: Feb. 25, 2021

(65) Prior Publication Data

US 2022/0334130 A1 Oct. 20, 2022

(30) Foreign Application Priority Data

Aug. 16, 2019 (KR) ........................ 10-2019-0100307
Aug. 16, 2019 (KR) ........................ 10-2019-0100308
Aug. 13, 2020 (KR) ........................ 10-2020-0101715
Aug. 13, 2020 (KR) ........................ 10-2020-0101716

(51) Int. Cl.

| | |
|---|---|
| ***C12Q 1/68*** | (2018.01) |
| ***A23L 33/00*** | (2016.01) |
| ***A23L 33/13*** | (2016.01) |
| ***A23L 33/17*** | (2016.01) |
| ***A61K 8/64*** | (2006.01) |
| ***A61K 38/17*** | (2006.01) |
| ***A61Q 19/02*** | (2006.01) |
| ***C12N 15/113*** | (2010.01) |
| ***C12P 19/34*** | (2006.01) |
| ***C12Q 1/6883*** | (2018.01) |
| ***G01N 33/50*** | (2006.01) |
| ***G01N 33/68*** | (2006.01) |

(52) U.S. Cl.

CPC .......... *G01N 33/6881* (2013.01); *A23L 33/13* (2016.08); *A23L 33/17* (2016.08); *A23L 33/40* (2016.08); *A61K 8/64* (2013.01); *A61K 38/1709* (2013.01); *A61Q 19/02* (2013.01); *C12N 15/113* (2013.01); *C12Q 1/6883* (2013.01); *G01N 33/5044* (2013.01); *A23V 2002/00* (2013.01); *C12N 2310/14* (2013.01); *C12N 2310/531* (2013.01); *C12Q 2600/158* (2013.01)

(58) Field of Classification Search

CPC combination set(s) only.
See application file for complete search history.

(56) References Cited

U.S. PATENT DOCUMENTS

2008/0207497 A1 8/2008 Ramakrishna et al.
2015/0064236 A1 3/2015 Bancel et al.

FOREIGN PATENT DOCUMENTS

KR 10-2010-0082202 A 7/2010
KR 10-2019-0016624 A 2/2019
KR 10-2019-0032250 A 3/2019

OTHER PUBLICATIONS

GenBank Locus: MN_201400 "Homo sapiens eukaryotic elongation factor 2 lysine methyltransferase (EEF2KMT), transcript variant 1, mRNA" Jun. 30, 2019, from https://www.ncbi.nlm.nih.gov/ (Year: 2019).*

Stacey A N D'Mello, et al. "Signaling Pathways in Melanogenesis" Int J Mol Sci. Jul. 15, 2016;17(7):1144. (Year: 2016).*

Eric C Lai, "Predicting and validating microRNA targets" Genome Biol. Aug. 31, 2004;5(9):115 (Year: 2004).*

San-Duk Yang, et al. "Estimation of Prognostic Marker Genes by Public Microarray Data in Patients with Ovarian Serous Cystadenocarcinoma" Yonsei Med J Jul. 2016;57(4):872-878 (Year: 2016).*

* cited by examiner

*Primary Examiner* — Stephen T Kapushoc

(74) *Attorney, Agent, or Firm* — NSIP Law

(57) ABSTRACT

The present invention relates to a melanogenesis detection method using FAM86A, and the like. The level of FAM86A of the present invention decreases according to an increase in the amount of melanin secretion or formation, and thus the present invention can whiten the skin by using protein FAM86A or an agonist thereof, and can prevent, treat or alleviate melanin-deficiency diseases such as vitiligo since the formation and secretion of melanin is promoted when FAM86A is inhibited. Therefore, the present invention is expected to be used in various ways, such as a composition for skin whitening using protein FAM86A or an agonist thereof, and as a composition for preventing and treating melanin deficiency diseases including vitiligo and canities by using a FAM86A inhibitor.

3 Claims, 20 Drawing Sheets

Specification includes a Sequence Listing.

MELANOGENESIS DETECTION METHOD USING FAM86A

CROSS REFERENCE TO RELATED APPLICATIONS

This application is a U.S. National Stage Application of International Application No. PCT/KR2020/095119 filed on Aug. 14, 2020, which claims the benefit under 35 USC 119(a) and 365(b) of Korean Patent Application Nos. 10-2019-0100307 and 10-2019-0100308, filed on Aug. 16, 2019, and Korean Patent Application Nos. 10-2020-0101715 and 10-2020-0101716, filed on Aug. 13, 2020, in the Korean Intellectual Property Office, the disclosure of which is incorporated herein by reference.

TECHNICAL FIELD

The present invention relates to a melanogenesis detection method using FAM86A.

BACKGROUND ART

The melanin pigment serves to determine a skin color and absorb UV rays to protect the skin. The melanin pigment consists of an amino acid called tyrosine, which is activated by an enzyme called tyrosinase. Tyrosine is synthesized into two types of melanin, pheomelanin and eumelanin, according to a conversion process. Pheomelanin is yellow to red in color, and eumelanin is a brown to black pigment, and generally found in Asians. Melanocytes producing the melanin pigment are derived from melanoblasts. When melanoblasts are stimulated to differentiate into melanocytes, tyrosinase is activated to change tyrosine contained in the cells into 3,4-dihydroxy-L-phenyl-alanine (DOPA), and DOPA is then changed into a material called dopaquinone by the action of an enzyme called dopaoxidase, followed by synthesis into melanin. After producing melanin, melanocytes move it to the epidermal tissue of the upper layer of the skin, and deliver it to keratinocytes present in the epidermal tissue. During the cell migration process, the melanin pigment is delivered while stored in melanosomes, and it is colorless at the beginning of production, filled with a black pigment over 4 to 5 steps while gradually moving to the upper layer, and finally becomes fully pigmented, mature melanin granules.

α-melanocyte-stimulating hormone (α-MSH) is very important for melanin production. α-MSH consists of the amino acid sequence of Ac-Ser-Tyr-Ser-Met-Glu-His-Phe-Arg-Trp-Gly-Lys-Pro-Val-$NH_2$, and is an agonist of melanocortin 1 receptor (MC1-R). When the agonist binds to MC1-R, MC1-R activates adenylate cyclase, and increases cAMP to activate PKA, and PKA phosphorylates a cAMP-responsive element binding protein transcription factor, finally activating a microphthalmia-associated transcription factor (MITF). MITF is also activated by the Wnt, GSK3β, and the MAPK signaling systems, and in response to various stimuli, it regulates the expression level of enzymes associated with melanin biosynthesis, such as tyrosinase (TYR), tyrosinase-related protein 1 (TYRP1), and dopachrome tautomerase (DCT; tyrosinase-related protein 2, also called TRP2).

The most important factor determining a human skin color is melanin produced by the action of several enzymes including tyrosinase in melanocytes in the human body, and when more melanin is produced than necessary, hyperpigmentation such as melasma, freckles and spots is caused, which is undesirable in terms of beauty. In addition, melanin generated by internal/external stressful stimuli does not disappear until it is released to the outside through keratinization of the skin even if the stress disappears.

Therefore, research is being conducted to inhibit the production of melanin, and materials having activity of suppressing ascorbic acid, kojic acid, arbutin, hydroquinone, glutathione or a derivative thereof, or tyrosinase have been used in combination with cosmetics or pharmaceuticals. However, their use is limited due to an insufficient whitening effect and a safety problem for the skin.

Also, vitiligo is an acquired depigmentation disorder in which white spots with various sizes and shapes appear on the skin due to the death or necrosis of melanocytes. This is a relatively common disease occurring in about 1% of the global population, and there is no difference according to race or region. The most common age of onset ranges from 10 to 30 years old, and 95% of cases occur before 40 years old, and 30% of vitiligo patients have a family history. The clinical features of vitiligo may include round or irregular-shaped white spots with various sizes, and in the beginning, the degree of discoloration is unclear, which however becomes apparent over time, and the boundary with normal skin may be unclear but may be darker and more distinct than a normal skin color. In rare cases, patients feel itchy. When white spots appear on hairy sites, particularly, hair and eyebrows, white hair may grow. Vitiligo may occur anywhere on the skin, but particularly, frequently occurs at bone-protruding regions such as fingers, toes, knees and elbows, around the mouth, nose or eye, underarms, or the inside of wrists. It can also occur on a mucous membrane such as the lips or genitals, and occurs particularly well in regions which are frequently damaged. Vitiligo is distributed symmetrically, or along nerves. In addition to the case in which white spots are simply generated on the skin, vitiligo may be accompanied by pigmentation abnormalities in the iris and retina of the eyes, and have complications such as diabetes, pernicious anemia, hypothyroidism or hyperthyroidism, Down's syndrome, biliary cirrhosis, gastric cancer, Addison's disease, alopecia areata, and an autoimmune disease such as lupus erythematosus. Although the exact cause of vitiligo is not yet known, several theories such as the autoimmune theory, stress, viral hypothesis, neurohumoral theory and melanocyte self-destruction theory have been proposed. In addition, various factors such as inherent cellular defects, genetic factors, apoptosis, and calcium metabolism abnormalities have been suggested.

When vitiligo is not treated, lesions worsen in most patients, so continuous treatment with steroids or UV light is required. However, since there are many cases in which proper treatment is not achieved with existing treatment methods, more effective treatment methods are urgently required.

In addition, there is a growing trend of preferring beautifully tanned skin from sunlight contrary to the wishes of ordinary people to have bright and smooth skin. In the world of black people, darker skin is accepted as beauty, and in the America and the East, healthy brown skin is also accepted as a symbol of leisure to play sports, so it is also used in fashion.

For this reason, conventionally, sunbathing was done using tanning oil containing a sunscreen, but is inconvenient and has disadvantages of rough skin and fine wrinkles. In addition, dihydroxyacetone was used to artificially darken the skin by a chemical bond on a skin surface. However, dihydroxyacetone makes the skin rough and causes irritation, and is difficult to apply evenly, and especially clothes are damaged by staining during use.

DISCLOSURE

Technical Problem

The technical problems to be achieved by the present invention are to provide a composition for detecting melanogenesis and a method of screening a skin whitening material, and the inventors confirmed that protein FAM86A is inversely proportional to the amount of melanin production, demonstrating that FAM86A may be used to detect melanogenesis and screen a whitening-associated material, and an effect of treating and alleviating a melanin-deficient disease such as vitiligo can be exhibited by suppressing FAM86A, and melanogenesis may be reduced by overexpressing FAM86A.

Therefore, the present invention is directed to providing a composition for detecting melanogenesis, which includes an agent for measuring an expression level of protein FAM86A or an expression level of mRNA thereof.

The present invention is also directed to providing a kit for detecting melanogenesis, which includes an agent for measuring an expression level of protein FAM86A or an expression level of mRNA thereof.

The present invention is also directed to providing a method of screening a skin whitening material, including the following steps:

(a) treating cells expressing protein FAM86A or mRNA thereof with a test material;

(b) measuring an expression level of the protein FAM86A or mRNA thereof in the cells treated with the test material and untreated cells; and (c) selecting a material increasing the expression level of the protein FAM86A or mRNA thereof, in comparison with control cells, as a skin whitening material.

The present invention is also directed to providing a composition for skin whitening, which includes protein FAM86A, an agonist thereof, or an activator thereof as an active ingredient.

The present invention is also directed to providing a composition for preventing or treating a pigmentation disorder, which includes protein FAM86A, an agonist thereof, or an activator thereof as an active ingredient.

The present invention is also directed to providing a composition for preventing, treating or alleviating a melanin-deficient disease, which includes an FAM86A inhibitor as an active ingredient.

The present invention is also directed to providing a method of screening a drug for preventing or treating a melanin-deficient disease, which includes the following steps:

(A) treating cells expressing protein FAM86A or mRNA thereof with a test material;

(B) measuring an expression level of the protein FAM86A or mRNA thereof in the cells treated with the test material and untreated cells; and (C) selecting a material reducing the expression level of the protein FAM86A or mRNA thereof, in comparison with control cells, as a drug for preventing or treating a melanin-deficient disease.

However, technical problems to be solved in the present invention are not limited to the above-described problems, and other problems which are not described herein will be fully understood by those of ordinary skill in the art from the following descriptions.

Technical Solution

To solve the above problems, the present invention provides a composition for detecting melanogenesis, which includes an agent for measuring an expression level of protein FAM86A or mRNA thereof; a use of an agent for measuring an expression level of protein FAM86A or mRNA thereof for detecting melanogenesis; and a kit for detecting melanogenesis, which includes an agent for measuring an expression level of protein FAM86A or mRNA thereof.

In addition, the present invention provides a method of screening a skin whitening material, which includes the following steps:

(a) treating cells expressing protein FAM86A or mRNA thereof with a test material;

(b) measuring an expression level of the protein FAM86A or mRNA thereof in the cells treated with the test material and untreated cells; and (c) selecting a material increasing the expression level of the protein FAM86A or mRNA thereof, in comparison with control cells, as a skin whitening material.

In addition, the present invention provides a composition for diagnosing a pigment-associated skin condition, which includes an agent for measuring an expression level of protein FAM86A or an expression level of mRNA thereof.

In addition, the present invention provides a kit for diagnosing a pigment-associated skin condition, which includes an agent for measuring an expression level of protein FAM86A or an expression level of mRNA thereof.

In addition, the present invention provides a method of providing information required for diagnosis of a pigment-associated skin condition, which includes the following steps:

(i) measuring an expression level of protein FAM86A or mRNA thereof in a sample obtained from a subject; and (ii) comparing the expression level of the protein FAM86A or mRNA thereof with a normal control and predicting that melanin is excessively produced in the subject in which the expression level of the protein FAM86A or mRNA thereof decreases.

In addition, the present invention provides a composition for skin whitening, which includes protein FAM86A, an agonist thereof or an activator thereof as an active ingredient; a skin whitening method, which includes administering a composition including protein FAM86A, an agonist thereof or an activator thereof into a subject; a use of a composition including protein FAM86A, an agonist thereof or an activator thereof for skin whitening; and a use of a protein FAM86A, an agonist thereof or an activator thereof for preparing an agent for skin whitening.

In addition, the present invention provides a pharmaceutical composition for preventing or treating a pigmentation disorder, which includes protein FAM86A, an agonist thereof or an activator thereof as an active ingredient; a method of preventing or treating a pigmentation disorder, which includes administering a composition including protein FAM86A, an agonist thereof or an activator thereof into a subject; protein FAM86A, an agonist thereof or an activator thereof; a use of a composition including protein FAM86A, an agonist thereof or an activator thereof for preventing or treating a pigmentation disorder; and a use of protein FAM86A, an agonist thereof or an activator thereof for preparing a drug for a pigmentation disorder.

According to one embodiment of the present invention, the agent for measuring an expression level of mRNA may be a probe or primer specifically binding to the mRNA of FAM86A.

According to another embodiment of the present invention, the agent for measuring an expression level of mRNA may be an antibody or aptamer specific for the protein FAM86A.

According to still another embodiment of the present invention, the mRNA of FAM86A may include or consist of a base sequence represented by SEQ ID NO: 6, but the present invention is not limited thereto.

The protein FAM86A may include or consist of an amino acid represented by SEQ ID NO: 1, but the present invention is not limited thereto.

According to yet another embodiment of the present invention, the agonist or activator may be one or more selected from the group consisting of an expression vector including a FAM86A gene, and cells including the vector, a compound and a peptide, but the present invention is not limited thereto.

According to yet another embodiment of the present invention, the pigmentation disorder may be one or more selected from the group consisting of pigmentation, melasma, freckles, blemishes, spots, macules, Nevus of Ota, cyanic melasma, gravidic chloasma, melasma shown in a woman taking an oral contraceptive, age spots, senile lentigines, wounds, hyperpigmentation after dermatitis-mediated inflammation and melanin dermatosis, but the present invention is not limited thereto.

In addition, the present invention provides a composition for preventing, treating or alleviating a melanin-deficient disease, which includes an FAM86A inhibitor as an active ingredient; a method of preventing or treating a melanin-deficient disease by administering a composition including an FAM86A inhibitor as an active ingredient into a subject; a use of a composition including an FAM86A inhibitor as an active ingredient for preventing or treating a melanin-deficient disease; and a use of an FAM86A inhibitor for preparing a drug for preventing or treating a melanin-deficient disease.

According to one embodiment of the present invention, the composition may be provided in the form of a pharmaceutical composition, a food composition or a cosmetic composition, but the present invention is not limited thereto.

According to another embodiment of the present invention, the food composition may be a health functional food composition, but the present invention is not limited thereto.

According to still another embodiment of the present invention, the melanin-deficient disease may be one or more selected from the group consisting of leukoderma, vitiligo, quadrichrome vitiligo, vitiligo ponctue, syndromic albinism [e.g., Alezzandrini syndrome, Hermansky-Pudlak syndrome, Chediak-Higashi syndrome, Griscelli syndrome (Elejalde syndrome), Griscelli syndrome type 2 and Griscelli syndrome type 3, Waardenburg syndrome, Tietz syndrome, CrossMuKusick-Breen syndrome, ABCD syndrome, Albinism-deafness syndrome and Vogt-Koyanagi-Harada syndrome], oculocutaneous albinism, canities, hypomelanosis [idiopathic guttate hypomelanosis, phylloid hypomelanosis, and progressive macular hypomelanosis], piebaldism, nevus depigmentosus, postinflammatory hypopigmentation, pityriasis alba, Vagabond's leukomelanoderma, Yemenite deaf-blind hypopigmentation syndrome, Wende-Bauckus syndrome, Woronoff's ring, amelanism, leucism and a skin depigmentation-associated disease, and preferably vitiligo or canities, but the present invention is not limited thereto.

According to yet another embodiment of the present invention, the composition may promote melanin synthesis or secretion.

According to yet another embodiment of the present invention, the inhibitor may be an FAM86A activity or expression inhibitor.

According to yet another embodiment of the present invention, the activity inhibitor may be one or more selected from the group consisting of a compound, peptide, peptide mimetic, substrate analog, aptamer and antibody, which specifically bind to protein FAM86A.

According to yet another embodiment of the present invention, the expression inhibitor may be one or more selected from the group consisting of an antisense nucleotide, RNAi, siRNA, miRNA, shRNA and a ribozyme, which complementarily bind to mRNA of the FAM86A gene.

According to yet another embodiment of the present invention, the shRNA may be represented by one or more base sequences selected from SEQ ID NO: 11 to SEQ ID NO: 20.

According to yet another embodiment of the present invention, the shRNA may target one or more base sequences selected from the group consisting of SEQ ID NO: 21 to SEQ ID NO: 30.

According to yet another embodiment of the present invention, the miRNA may be represented by one or more base sequences selected from the group consisting of SEQ ID NO: 40 to SEQ ID NO: 45.

In addition, the present invention provides a method of screening a drug for preventing or treating a melanin-deficient disease, which includes the following steps:

(A) treating cells expressing protein FAM86A or mRNA thereof with a test material;

(B) measuring an expression level of the protein FAM86A or mRNA thereof in the cells treated with the test material and untreated cells; and (C) selecting a material reducing the expression level of the protein FAM86A or mRNA thereof, in comparison with control cells, as a drug for preventing or treating a melanin-deficient disease.

In addition, the present invention provides a composition for promoting melanogenesis, which includes an FAM86A inhibitor as an active ingredient; a method of promoting melanogenesis, which includes administering a composition including an FAM86A inhibitor as an active ingredient; a use of a composition including an FAM86A inhibitor as an active ingredient for promoting melanogenesis; and a use of an FAM86A inhibitor for preparing a melanogenesis promoting agent.

In one embodiment of the present invention, the promotion of melanogenesis may be for one or more selected from the group consisting of preventing white hair, promoting the induction of black hair, and controlling the color of a subject, but the present invention is not limited thereto.

In addition, the present invention provides a composition for promoting black hair, which includes an FAM86A inhibitor as an active ingredient; a method of preventing white hair or promoting the induction of black hair by administering a composition including an FAM86A inhibitor as an active ingredient; a use of a composition including an FAM86A inhibitor as an active ingredient for preventing white hair or promoting the induction of black hair; and a use of an FAM86A inhibitor for preparing a white hair preventing agent or a black hair induction-promoting agent.

In addition, the present invention provides a composition for controlling the color of a subject, which includes an FAM86A inhibitor as an active ingredient; a method of controlling the color of a subject by administering a composition including an FAM86A inhibitor as an active ingredient; a use of a composition including an FAM86A inhibitor as an active ingredient for controlling the color of a subject; and a use of an FAM86A inhibitor for preparing a subject's color controlling agent.

Advantageous Effects

Since the level of FAM86A of the present invention decreases with an increase in secretion or production amount of melanin, it is possible to achieve skin whitening using protein FAM86A or an agonist thereof, and FAM86A suppression promotes melanin production and secretion, enabling the prevention, treatment or alleviation of a melanin-deficient disease such as vitiligo. Therefore, it is expected that the present invention can be used in various aspects including a composition for skin whitening using protein FAM86A or an agonist thereof, and a composition for preventing and treating melanin-deficient diseases including vitiligo, canities, etc., which includes an FAM86A inhibitor.

MODES OF THE INVENTION

Figure 1:
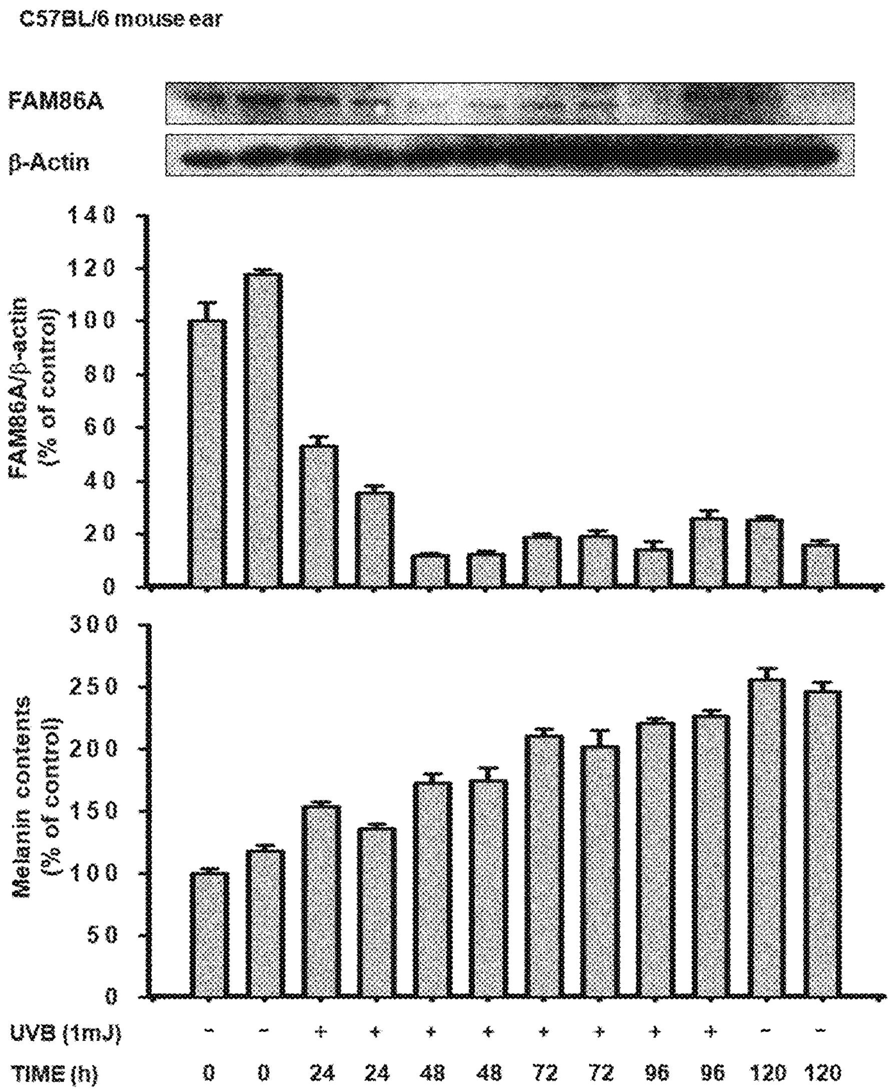
FIG. 1 shows a result of confirming an expression level of protein FAM86A over time through western blotting analysis, after C57BL/6 mice are treated with UVB (1 mJ) (top), and a result of confirming a melanin production amount using the same sample through a melanin content assay (bottom).

Hereinafter, the present invention will be described in detail.

The inventors had conducted research on a FAM86A-melanin relationship according to examples, thereby confirming that FAM86A expression rather decreases when melanogenesis is promoted by α-MSH induction, and During research on a novel therapeutic target associated with melanin in order to treat a melanin-deficient disease, it was confirmed that an FAM86A inhibitor has an effect of treating and alleviating melanin-deficient diseases including canities and vitiligo, and thus the present invention was completed (see examples of the present invention).

The term "protein" used herein is used interchangeably with a 'polypeptide' or 'peptide', and refers to, for example, a polymer of amino acid residues as generally found in a natural protein.

The "polynucleotide" or "nucleic acid" used herein refers to single- or double-stranded deoxyribonucleic acid (DNA) or ribonucleic acid (RNA). Unless otherwise limited, the "polynucleotide" or "nucleic acid" also includes known analogues of a natural nucleotide hybridized with a nucleic acid in the same manner as a naturally-occurring nucleotide. Generally, DNA consists of four bases such as adenine (A), guanine (G), cytosine (C) and thymine (T), and RNA has uracil (U) instead of thymine. In the double-stranded nucleic acid, A forms a hydrogen bond with T or U, and C forms a hydrogen bond with G. Such base relationships are called "complementary."

In addition, the "messenger RNA (mRNA)" is RNA serving as the blueprint of polypeptide synthesis (protein translation) by delivering the genetic information of the base sequence of a specific gene to a ribosome in protein synthesis. Single-stranded mRNA is synthesized through transcription using the gene as a template.

The "FAM86" used herein is a protein belonging to the protein MTase family, and it is known that a single FAM86 gene is present in the genomes of most mammals, primate FAM86 is contained in the replication region of a part in which a tumor easily occurs and is spread over several genomic positions (Identification and Characterization of a Novel Evolutionarily Conserved Lysine-specific Methyltransferase Targeting Eukaryotic Translation Elongation Factor 2 (eEF2), JOURNAL OF BIOLOGICAL CHEMISTRY, VOLUME 289, NUMBER 44, Oct. 31, 2014).

In the present specification, the FAM86 may be FAM86A, but the present invention is not limited thereto.

The protein FAM86A used herein may be derived from a mammal, and preferably, a human. Most preferably, the protein FAM86A of the present invention is characterized by including an amino acid sequence represented as human FAM86A (NP_958802.1) of SEQ ID NO: 1 (in parentheses, NCBI GenBank accession number).

The FAM86 mRNA preferably includes a base sequence represented as human FAM86A mRNA (NM_201400.4) of SEQ ID NO: 6 (in parentheses, NCBI GenBank accession number). Features of coding regions (exons) of the human FAM86A mRNA transcript variants are identified from sequence information obtained by searching the NCBI database by the GenBank accession number described in the parentheses.

The term "complementary" used herein means that a targeting moiety in a nucleic acid molecule under a predetermined hybridization or annealing condition, particularly, a physiological condition (in cells), is sufficiently complementary to be selectively hybridized with a target (e.g., FAM86A gene), and may have one or more mismatched base sequences, and includes both substantially complementary and perfectly complementary, and more specifically, means perfectly complementary.

Therefore, the present invention provides a composition for detecting melanogenesis or composition for diagnosing a pigmentation-associated skin condition, which includes an agent for measuring an expression level of protein FAM86A or an expression level of mRNA thereof.

In addition, the present invention provides a composition for detecting excessive melanogenesis, which includes an agent for measuring an expression level of protein FAM86A or an expression level of mRNA thereof.

The term "detecting" used herein refers to all of measuring and confirming the presence of a targeted material (FAM86A, which is a marker protein of the present invention), and measuring and confirming a change in level (expression level) of an existing targeted material. In the same context, the measuring the expression level of the protein in the present invention means measuring whether expression occurs, or measuring a qualitative or quantitative change level of the protein. The measurement may be performed without limitation by both qualitative and quantitative methods (analyses). In the measurement of a protein level, types of the qualitative and quantitative methods are well known in the art, and include the experimental methods described in the present specification. A specific protein level comparison method for each method is well known in the art. Therefore, the protein FAM86A detection means detection of the presence of protein FAM86A, or confirmation of an increase (upregulation) or decrease (downregulation) in expression level of the protein.

The "increase in expression (or high expression)" of a protein in the present specification means expression of a protein which has not been expressed (that is, detection of a protein which has not been detected) or relative overexpression compared to a normal level (that is, increase in detection amount). The meaning of the opposite terms can be understood, by those of ordinary skill in the art, to have opposite meanings according to the above definition.

In the present specification, the agent for measuring an mRNA expression level may be a probe or primer specifically binding to the mRNA of FAM86A, but the present invention is not limited thereto.

In the present invention, the agent for measuring a protein expression level may be an antibody or aptamer specific for the protein FAM86A, but the present invention is not limited thereto.

According to another embodiment of the present invention, the mRNA of FAM86A may comprise a base sequence represented by SEQ ID NO: 6, but the present invention is not limited thereto.

In the present specification, the protein FAM86A may comprise an amino acid sequence represented by SEQ ID NO: 1, but the present invention is not limited thereto.

The "primer" is a single-stranded oligonucleotide acting as a starting point of DNA synthesis. The primer specifically binds to a polynucleotide, which is a template, with a suitable buffer and under a suitable temperature, and the DNA polymerase synthesizes DNA by additionally linking a nucleoside triphosphate having a base complementary to the template DNA to the primer. The primer generally consists of a 15 to 30-base sequence, and a melting temperature (Tm) at which binding to a template strand is achieved varies depending on a base composition and a sequence length. The primer sequence does not need to have a perfectly complementary sequence to a partial base sequence of the template, but it is enough to have sufficient complementarity within a range exhibiting an inherent action of the primer by hybridization with the template. Accordingly, in the present invention, a primer for measuring the expression level of FAM86A mRNA does not need to have a perfectly complementary sequence to each gene sequence, and it is sufficient if it has a length and complementarity suitable for the purpose of measuring the amount of mRNA by amplifying a specific region of mRNA or complementary DNA (cDNA) through DNA synthesis. Primers for the amplification process consist of a set (pair) that which complementarily binds to a template (or sense) and an opposite side (antisense) at each end of a specific region of mRNA to be amplified. The primer may be easily designed with reference to the base sequence of mRNA or cDNA of KRS or AIMP1 by those of ordinary skill in the art. In the present invention, the primer is preferably one set or pair or a combination thereof, which specifically binds to mRNA of FAM86A represented by SEQ ID NO: 6.

The "probe" refers to a fragment of polynucleotide such as RNA or DNA with a length of several to several hundred base pairs, which can specifically bind to mRNA or cDNA of a specific gene, and is labeled so it is possible to check the presence or absence or expression level of target mRNA or cDNA to be bound. For the purpose of the present invention, as an expression level of FAM86A mRNA is measured by the hybridization of a probe complementary to FAM86A mRNA with a subject's sample, the probe can be used in diagnosis of a pigmentation-associated skin condition or detection of the overproduction of melanin. Conditions for probe selection and hybridization may be appropriately selected according to techniques known in the art. In the present invention, the primer or probe may be chemically synthesized using a phosphoramidite solid support synthesis method or other widely known methods. In addition, the primer or probe may be modified in various ways according to a method known in the art in a range that does not interfere with hybridization with FAM86A mRNA. Examples of such modifications include methylation, capping, substitution with one or more homologues of natural nucleotides, modification between nucleotides such as an uncharged linkage (e.g., methyl phosphonate, phosphotriester, phosphoroamidate or carbamate) or a charged linkage (e.g., phosphorothioate or phosphorodithioate), and binding of a labeling material using fluorescence or an enzyme.

The antibody refers to a specific protein molecule directed against an antigenic region. The antibody used in the present invention may be a monoclonal or polyclonal antibody, an immunologically active fragment (e.g., a Fab or (Fab)2 fragment), an antibody heavy chain, a humanized antibody, an antibody light chain, a genetically manipulated single-chain Fv molecule, or a chimeric antibody.

The "aptamer" refers to a material capable of specifically binding to an analyte to be detected in a sample, and a single-stranded nucleic acid having a stable tertiary structure by itself (DNA, RNA, or a modified nucleic acid), and may specifically confirm the presence of a target protein in a sample. By a general method of preparing an aptamer, an aptamer may be synthesized by determining the sequence of an oligonucleotide with selective and high binding ability to a target protein to be confirmed, and by modifying it with —SH, —COOH, —OH or $NH_2$ to make the 5' or 3' end of the oligonucleotide bind to a functional group of an aptamer chip, but the present invention is not limited thereto.

The protein FAM86A is a known protein, and thus may be prepared using the antibody used in the present invention as an antigen according to a common method widely known in the immunology field. The protein FAM86A used as an antigen of the antibody according to the present invention may be naturally extracted or synthesized, and may be prepared by a recombinant method based on a DNA sequence. According to the genetic recombination technique, a nucleic acid encoding the protein FAM86A may be inserted into an appropriate expression vector, host cells may be cultured to express the protein FAM86A in a transformant transformed with a recombinant expression vector, and then the protein FAM86A may be recovered from the transformant.

For example, a polyclonal antibody may be produced by a method of injecting an antigen of the protein FAM86A into an animal, collecting blood from the animal, and obtaining serum containing an antibody. The antibody may be prepared using several warm-blooded animals such as a horse, a cow, a goat, sheep, a dog, a chicken, a turkey, a rabbit, a mouse or a rat.

Also, a monoclonal antibody may be prepared using a known fusion method (Kohler and Milstein, European J. Immunol. 6:511-519, 1976), a recombinant DNA method (U.S. Pat. No. 4,816,567) and a phage antibody library technique (Clackson et al., Nature, 352, 624-628, 1991; Marks et al., J. Mol. Biol. 222, 58:1-597, 1991).

Meanwhile, the present invention provides a kit for detecting melanogenesis or kit for diagnosing a pigmentation-associated skin condition, which includes an agent for measuring an expression level of protein FAM86A or mRNA thereof.

The kit may further include a tool and/or reagent known in the art, which is used in immunological analysis in addition to an FAM86A protein antibody.

In the above, the immunological analysis may include any method capable of measuring the binding of an antibody to an antigen. Such a method is known in the art, and may be, for example, immunocytochemistry and immunohistochemistry, radioimmunoassay, enzyme linked immunoabsorbent assay (ELISA), immunoblotting, Farr assay, immunoprecipitation, latex aggregation, hemagglutination, nephrocytometry, immunodiffusion, counter-current electrophoresis, single radical immunodiffusion, protein chip assay, or immunofluorescence.

As tools and/or reagents used in immunological assays, suitable carriers or supports, labels capable of producing detectable signals, solubilizing agents and detergents are included. In addition, when the labeling material is an enzyme, it may include a substrate capable of measuring enzyme activity and a reaction terminator.

The FAM86A included in the detection or diagnosis kit of the present invention is preferably fixed to a suitable carrier or support using various methods as disclosed in the literature (Antibodies: A Laboratory Manual, Harlow & Lane; Cold Spring Harbor, 1988), and examples of suitable carriers or supports include agarose, cellulose, nitrocellulose, dextran, Sephadex, Sepharose, a liposome, carboxymethyl cellulose, polyacrylamide, polysterine, gabbro, a filter paper, an ion exchange resin, a plastic film, a plastic tube, glass, a polyamine-methyl vinyl-ether-maleic acid copolymer, an amino acid copolymer, an ethylene-maleic acid copolymer, nylon, cups, and flat packs. In addition, other solid substrates include a cell culture plate, an ELISA plate, a tube and a polymeric membrane. The support may have any possible shape, for example, a spherical (bead), cylindrical (test tube or inside of well), or flat (sheet or test strip).

Labels capable of generating a detectable signal enables qualitative or quantitative measurement of the formation of an antigen-antibody complex, and examples of labels may include an enzyme, a fluorescent material, a ligand, a light emitting material, a microparticle, a redox material and a radioactive material. As an enzyme, β-glucuronidase, β-D-glucosidase, urase, peroxidase, alkaline phosphatase, acetylcholinesterase, glucose oxidase, hexokinase, malate dehydrogenase, glucose-6-phosphonate dehydrogenase or invertase may be used. As a fluorescent material, fluorescein, isothiocyanate, rhodamine, phycoerythrin, phycocyanin, allophycocyanin, or fluorescein isothiocyanate may be used. As a ligand, a biotin derivative may be used, and as a light emitting material, acridinium ester, luciferin or luciferase may be used. Examples of microparticles include colloidal gold and colored latex, and examples of redox molecules include ferrocene, a ruthenium complex compound, a viologen, a quinone, a Ti ion, a Cs ion, diimide, 1,4- benzoquinone, and hydroquinone. However, in addition to the above examples, any one that can be used in an immunological assay may be used.

In addition, the present invention provides a method of screening a skin whitening material, which includes the following steps:

(a) treating cells expressing protein FAM86A or mRNA thereof with a test material;

(b) measuring an expression level of the protein FAM86A or mRNA thereof in the cells treated with the test material and untreated cells; and (c) selecting a material increasing the expression level of the protein FAM86A or mRNA thereof, in comparison with control cells, as a skin whitening material.

In addition, the present invention provides a method of preventing or screening a melanin-deficient disease, which includes the following steps:

(A) treating cells expressing protein FAM86A or mRNA thereof with a test material;

(B) measuring an expression level of the protein FAM86A or mRNA thereof in the cells treated with the test material and untreated cells; and (C) selecting a material reducing the expression level of the protein FAM86A or mRNA thereof, in comparison with cells which are not treated with the test material, as a drug for preventing or treating a melanin-deficient disease.

In the present specification, the cells expressing the protein FAM86A or mRNA thereof include cells in which the protein FAM86A or mRNA thereof is endogenously expressed or temporarily highly-expressed, or may be transformed by introduction of a nucleic acid encoding FAM86A into the cells to highly express FAM86A, but the present invention is not particularly limited.

In the present specification, the cells expressing the protein FAM86A or mRNA thereof may excessively produce melanin, but the present invention is not particularly limited thereto.

The "expression" used herein refers to production of a protein or nucleic acid in cells. The cells expressing FAM86A may be cells endogenously expressing FAM86A, or cells which are transformed with a recombinant expression vector including a polynucleotide encoding FAM86A to highly express FAM86A. Preferably, the cells expressing the FAM86A gene may be cells derived from melanocytes. The inventors have used a B6F10 cell line as cells endogenously expressing FAM86A.

The term "test material" used to describe the screening method of the present invention refers to an unknown material used in screening to test whether or not it affects the expression of FAM86A of the present invention. The test material may be small interference RNA (siRNA), short hairpin RNA (shRNA), microRNA (miRNA), a ribozyme, a DNAzyme, a peptide nucleic acid (PNA), an antisense oligonucleotide, an antibody, an aptamer, a natural extract or a chemical material, but the present invention is not limited thereto.

In addition, the cells used in step (a) or (A) may be provided in the form of an experimental animal, and in this case, the screening method of the present invention may further include a step of inducing melanogenesis in the experimental animal, and the contact with the test material includes parenteral or oral administration and stereotaxic injection, but the present invention is not limited thereto, and a suitable method for testing an experimental material in an animal may be selected by those of ordinary skill in the art.

The treatment of an experimental material means culturing an experimental material for a certain time after adding it to a cell or tissue culture medium. When the cells are provided in the form of an experimental animal, the contact with an experimental animal includes parenteral or oral administration or stereotaxic injection, but the present invention is not limited thereto, and a suitable method for testing an experimental material in an animal may be selected by those of ordinary skill in the art.

In the step (b) or (B) of the present invention, an expression level of mRNA may be measured using one or more methods selected from the group consisting of RT-PCR, quantitative or semi-quantitative RT-PCR, quantitative or semi-quantitative real-time RT-PCR, Northern blotting and a DNA or RNA chip assay, but the present invention is not limited thereto.

In the step (b) or (B) of the present invention, an expression level of the protein may be measured using one or more methods selected from the group consisting of Western blotting, ELISA, radioimmunoassay, radioimmunodiffusion, Ouchterlony immunodiffusion, rocket immunoelectrophoresis, immunohistochemical staining, an immunoprecipitation assay, a complement fixation assay, FACS and a protein chip assay, but the present invention is not limited thereto.

The step (c) or (C) is for selecting a material increasing an expression level of the protein FAM86A or mRNA thereof as a skin whitening material, in comparison with control cells.

The step (c) or (C) is for selecting a material reducing an expression level of the protein FAM86A or mRNA thereof as a drug for preventing or treating a melanin-deficient disease, in comparison with control cells.

The control cells may be cells not treated with an experimental material, but the present invention is not limited thereto.

In the present specification, when the expression level of the FAM86 gene or protein in a melanin overproduction sample which is in contact with a candidate material increases more than that of the corresponding gene or protein, a step of determining the candidate material as a melanin production inhibitor and/or a pigmented skin disease-treating agent and/or a skin whitening agent may be included.

In the present specification, when the expression level of the FAM86 gene or protein in a melanin overproduction sample which is in contact with a candidate material decreases less than that of the corresponding gene or protein, a step of determining the candidate material as a melanin production promoter and/or a pigmentation disorder-treating agent may be included.

In addition, the present invention provides a method for providing information required for diagnosis of a pigmentation-associated skin condition, including the following steps:

(i) measuring an expression level of protein FAM86A or mRNA thereof in a sample obtained from a subject; and (ii) comparing the expression level of the protein FAM86A or mRNA thereof with a normal control and predicting that melanin is excessively produced in the subject in which the expression level of the protein FAM86A or mRNA thereof decreases.

The pigmentation-associated skin condition in the present invention means information on skin showing a skin type or condition associated with the melanin pigment. In the present invention, information associated with various skin characteristics, and particularly, pigmentation is targeted for diagnosis.

In the present invention, the biological sample may be anything, without limitation, that is collected from a subject to be used to diagnose a pigmentation-associated skin condition, for example, cells or tissue obtained by biopsy, blood, whole blood serum, plasma, saliva, cerebrospinal fluid, various secretions, urine or feces. Preferably, the biological sample may be selected from the group consisting of blood, plasma, serum, saliva, nasal discharge, sputum, ascites, vaginal discharge and urine, and preferably, tissue or cells.

In comparison with a normal control in which an expression level of the protein FAM86A or mRNA thereof is measured in a subject measured by the method of Step (i), when the expression level of the protein FAM86A or mRNA thereof decreases, the subject may be determined as a case in which melanin is excessively formed.

The subject and various samples used herein may be any animal, and preferably, a mammal, more preferably, a human, or a sample or biopsy sample obtained therefrom may be any tissue, body fluid or cell, for example, skin tissue or skin cells or fibroblasts. In addition, a normal individual has no symptoms and signs of overproduction of melanin and a pigmented skin disease caused thereby, and refers to an individual which has no personal or familial history of melanin overproduction and a history of a pigmented skin disease resulting therefrom.

The melanin overproduction sample may be obtained naturally from an animal, for example, a mammal, preferably a human, or obtained by an artificial method, and the artificial method includes over-expressing tyrosinase in non-pigmented cells.

In addition, the present invention provides a composition for skin whitening, which includes protein FAM86A, or an agonist or activator as an active ingredient.

In addition, the present invention provides a skin whitening method, which includes administering protein FAM86A, or an agonist or activator thereof into a subject.

In addition, the present invention provides a use of protein FAM86A, or an agonist or activator thereof for preparing an agent for skin whitening.

The composition may be provided in the form of a pharmaceutical composition, a food composition or a cosmetic composition, but the present invention is not limited thereto.

In the present invention, the agonist or activator may be one or more selected from the group consisting of an expression vector including a FAM86A gene, and a cell which includes the vector, a compound and a peptide, but the present invention is not limited thereto.

In the present invention, the expression vector includes a FAM86A gene, and as long as it is an FAM86A recombinant expression vector, the present invention is not limited. For example, the expression vector may be linear DNA, plasmid DNA or a recombinant viral vector.

In the present invention, the FAM86A gene included in the expression vector may include or consist of a base sequence represented by SEQ ID NO: 47.

In the present invention, the recombinant virus may be one or more selected from the group consisting of a retrovirus, an adenovirus, an adeno-associated virus, a herpes simplex virus and a lentivirus, but the present invention is not limited thereto.

The "whitening" used herein refers to not only brightening skin tone, but also improving skin hyperpigmentation such as melasma or freckles caused by UV rays, hormones or heredity by inhibiting the synthesis of the melanin pigment.

In addition, the "whitening" used herein includes whitening of black or yellow skin, and also includes converting black or yellow skin into white skin.

The pharmaceutical composition according to the present invention may be used to improve and alleviate pigmentation, melasma, freckles, spots, macules, Nevus of Ota, cyanic melasma, gravidic chloasma, melasma shown in a woman taking an oral contraceptive, age spots, senile lentigines, wounds, hyperpigmentation after dermatitis-mediated inflammation and melanin dermatosis, caused by a pathological condition of excessive melanin pigmentation, for example, aging/photoaging, rapid hormonal changes such as pregnancy, skin damage caused by wounds, inflammation and burns or skin regeneration therefrom.

In addition, the present invention provides a composition for preventing, treating or alleviating a melanin-deficient disease, which includes a FAM86A inhibitor as an active ingredient.

In addition, the present invention provides a composition for skin darkening, which includes an FAM86A inhibitor as an active ingredient. When applied to rat melanoma cells, the FAM86A inhibitor of the present invention may exhibit a very potent melanogenesis-promoting effect, confirming that it can be used as a skin darkening agent or a sun tanning product.

Accordingly, the FAM86A inhibitor of the present invention may be used as a composition for promoting melanogenesis, and by promoting melanogenesis, the FAM86A inhibitor may adjust the skin or hair color of animals including a human, and particularly, exhibit an effect of darkening hair color.

In the present specification, the inhibitor may be an FAM86A activity inhibitor or expression inhibitor, but the present invention is not limited thereto.

In the present specification, the activity inhibitor may be one or more selected from the group consisting of a compound, peptide, peptide mimetic, substrate analog, aptamer and antibody, which specifically bind to the protein FAM86A, but the present invention is not limited thereto.

In the present specification, the expression inhibitor may be one or more selected from the group consisting of an antisense nucleotide complementarily binding to mRNA of the FAM86A gene, RNAi, siRNA, miRNA, shRNA and a ribozyme, but the present invention is not limited thereto.

The term "siRNA" used herein may have a structure forming a double chain since a sense strand (e.g., a sequence corresponding to mRNA sequence of the FAM86A gene) is located opposite to an antisense strand (e.g., a sequence complementary to the mRNA sequence of the FAM86A gene). In addition, the siRNA molecule that can be used in the present invention may have a single chain structure with self-complementary sense and antisense strands. siRNA is not limited to complete pairing of double-stranded RNA parts that pair with each other and may include a non-pairing part by a mismatch (a corresponding base is not complementary) or a bulge (no base corresponding to one-direction sequence). Specifically, the total length is 10 to 100 bases, more specifically, 15 to 80 bases, and still more specifically, 20 to 70 bases. In the present invention, the siRNA may specifically target one or more base sequences selected from the group consisting of SEQ ID NO: 31 to SEQ ID NO: 39.

The term "small hairpin RNA or short hairpin RNA (shRNA)" used herein may indicate an RNA sequence forming a strong hairpin turn, which may be used to silence gene expression through RNA interference. shRNA may be introduced into cells using any promoter capable of functioning in eukaryotic cells, but in the present invention, a pLKO.1 vector was used. Such a vector may always be delivered to daughter cells such that gene silencing is inherited. The hairpin structure of shRNA is degraded into intracellular machinery siRNA to bind to an RNA-induced silencing complex. The above-described complex binds to mRNA matched to the bound siRNA for degradation. shRNA may be transcribed by RNA polymerase III, and shRNA production in mammal cells may allow cell recognition of shRNA as viral attack, causing an interferon reaction by finding a protection means. In the present invention, the shRNA may specifically comprise one or more base sequences selected from the group consisting of SEQ ID NO: 11 to SEQ ID NO: 20, and preferably, consists of one or more base sequences selected from the group consisting of SEQ ID NO: 11 to SEQ ID NO: 20. In the present invention, the shRNA may specifically target one or more base sequences selected from the group consisting of SEQ ID NO: 21 to SEQ ID NO: 30.

The term "microRNA (miRNA)" is a single-stranded RNA molecule of 21 to 25 nucleotides, and a material that controls eukaryotic gene expression by binding to the 3'-UTR of messenger RNA (mRNA) (Bartel D P, et al., Cell, 23; 116(2): 281-297(2004)). The miRNA is made of pre-miRNA having a stem-loop structure by Drosha (RNase III type enzyme), moves to the cytoplasm, and formed into mature miRNA by cleavage by a dicer. In the present invention, the miRNA may specifically include one or more base sequences selected from the group consisting of SEQ ID NO: 40 to SEQ ID NO: 45, and preferably may consist of one or more base sequences selected from the group consisting of SEQ ID NO: 40 to SEQ ID NO: 45.

The term "antisense oligonucleotide" used herein refers to DNA or RNA containing a nucleic acid sequence complementary to the sequence of specific mRNA, or a derivative thereof, and serves to suppress translation of mRNA into a protein by binding to a complementary sequence in mRNA. For example, the antisense sequence of the present invention refers to a DNA or RNA sequence complementary to FAM86A and capable of binding to FAM86A mRNA, and may suppress activity necessary for translation of FAM86A mRNA, translocation into the cytoplasm, maturation or all overall biological functions. The length of the antisense nucleic acid may be 6 to 100 bases, specifically, 8 to 60 bases, and more specifically, 10 to 40 bases.

The term "ribozyme" used herein is RNA having the same function as an enzyme which recognizes the base sequence of specific RNA and cleaves it by itself. The ribozyme consists of a region having specificity to a complementary base sequence of a target mRNA strand and a region cleaving target RNA. The term "aptamer" used herein refers to an oligonucleotide (in general, an RNA molecule) binding to a specific target. Specifically, the "aptamer" used herein refers to an oligonucleotide aptamer (e.g., an RNA aptamer).

In the present specification, siRNA or shRNA may have various modifications for improvement of in vivo stability of an oligonucleotide, provision of resistance to a nuclease and reduction in non-specific immune responses. The modifications of an oligonucleotide may include a combination of one or more modifications selected from modification by substitution of OH group(s) at the 2' carbon position of the sugar structure in one or more nucleotides with —$CH_3$ (methyl), —$OCH_3$ (methoxy), —$NH_2$, —F, —O-2-methoxyethyl, —O-propyl, —O-2-methylthioethyl, —O-3-aminopropyl, —O-3-dimethylaminopropyl, —O—N-methylacetamido or —O-dimethylamidooxyethyl; modification by substitution of oxygen in the sugar structure in a nucleotide with sulfur; and modification of a nucleotide bond to a phosphorothioate, boranophosphate or methyl phosphonate bond, and modification to a peptide nucleic acid (PNA), a locked nucleic acid (LNA) or an unlocked nucleic acid (UNA) can be used.

The term "complementary" used herein means being sufficiently complementary for a targeting moiety in a nucleic acid molecule under a predetermined hybridization or annealing condition, specifically, a physiological condition (in cells), can be selectively hybridized to a target (e.g., FAM86A gene), and includes substantially complementary and perfectly complementary, and more specifically perfectly complementary, while having a base sequence with one or more mismatches.

In the present specification, melanin-deficient diseases to which the composition of the present invention can be applied may include leukoderma, vitiligo, quadrichrome vitiligo, vitiligo ponctue, syndromic albinism [e.g., Alezzandrini syndrome, Hermansky-Pudlak syndrome, Chediak-Higashi syndrome, Griscelli syndrome (Elejaide syndrome), Griscelli syndrome type 2, Griscelli syndrome type 3, Waardenburg syndrome, Tietz syndrome, CrossMuKusick-Breen syndrome, ABCD syndrome, Albinism-deafness syndrome, Vogt-Koyanagi-Harada syndrome], oculocutaneous albinism, canities, hypomelanosis (idiopathic guttate hypomelanosis, phylloid hypomelanosis, and progressive macular hypomelanosis), piebaldism, nevus depigmentosus, postinflammatory hypopigmentation, pityriasis alba, Vagabond's leukomelanoderma, Yemenite deaf-blind hypopigmentation syndrome, Wende-Bauckus syndrome, Woronoff's ring, amelanism, leucism and skin discoloration-associated diseases, but the present invention is not limited thereto.

The "vitiligo," which is a subject of alleviation, treatment or prevention of the present invention, is pigmentation deficiency characterized by localized depigmented spots as a result of loss of melanin and functional melanocytes from the epidermis of the skin. In addition, the "canities" refers to a symptom called "hair graying or whitening," and a symptom in which the shade of individual hair fades, resulting in mixing various shades of hair including normal to white colors. The canities is known to be caused by a decrease in tyrosinase activity in hair bulbar melanocytes due to toxic oxidative damage to melanocytes, which are melanin biosynthesis cells.

The composition of the present invention may be provided in the form of a pharmaceutical composition, a food composition, or a cosmetic composition, but the present invention is not limited thereto.

In addition, the present invention provides a method of preventing or treating a melanin-deficient disease by administering a composition including an FAM86A inhibitor as an active ingredient into a subject.

In addition, the present invention provides a use of an FAM86A inhibitor for preparing a drug for preventing or treating a melanin-deficient disease.

In addition, the present invention provides a composition for preventing canities, which includes an FAM86A inhibitor as an active ingredient.

In addition, the present invention provides a method of treating canities by administering a composition including an FAM86A inhibitor as an active ingredient into a subject.

In addition, the present invention provides a use of an FAM86A inhibitor for preparing a drug for preventing or treating canities.

In the present specification, the composition may promote the synthesis or secretion of melanin, but the present invention is not limited thereto.

In addition, the present invention provides a composition for promoting black hair induction, which includes an FAM86A inhibitor as an active ingredient. Moreover, the present invention provides a method of promoting black hair induction by administering a composition including an FAM86A inhibitor as an active ingredient into a subject and a use of an FAM86A inhibitor for promoting black hair induction.

In addition, the present invention provides a composition for adjusting the color of a subject, which includes an FAM86A inhibitor as an active ingredient, and specifically, a composition for adjusting a fur color or skin color of a pet. Moreover, the present invention provides a use of a method of adjusting the color of a subject by administering a composition including an FAM86A inhibitor as an active ingredient into a subject, and a use of an FAM86A inhibitor for adjusting the color of a subject.

Since the FAM86A inhibitor of the present invention has an effect of promoting melanogenesis, when including the FAM86A inhibitor, it may prevent the generation of white hair and promote the induction and generation of black hair.

The present invention may also include a pharmaceutically acceptable salt of target material as an active ingredient. The term "pharmaceutically acceptable salt" used herein includes a salt derived from a pharmaceutically acceptable inorganic acid, organic acid or base. The term "sitologically acceptable salt" used herein includes a salt derived from a sitologically acceptable organic acid, inorganic acid or base. The term "veterinary acceptable salt" includes a salt derived from a veterinary acceptable inorganic acid, organic acid or base.

Examples of suitable acids may include hydrochloric acid, hydrobromic acid, sulfuric acid, nitric acid, perchloric acid, fumaric acid, maleic acid, phosphoric acid, glycolic acid, lactic acid, salicylic acid, succinic acid, p-toluene sulfonic acid, tartaric acid, acetic acid, citric acid, methane sulfonic acid, formic acid, benzoic acid, malonic acid, gluconic acid, naphthalene-2-sulfonic acid, and benzenesulfonic acid. The acid addition salt may be prepared by a conventional method, for example, by dissolving a compound in an excess acidic solution, and precipitating the salt using a water-miscible organic solvent such as methanol, ethanol, acetone or acetonitrile. Alternatively, the acid addition salt may be prepared by heating equimolar amounts of compound and an acid or alcohol in water, and evaporating or drying the mixture, or suction-filtering the precipitated salt.

Salts induced from suitable bases may include alkali metals such as sodium and potassium, alkaline earth metals such as magnesium, and ammonium, but the present invention is not limited thereto. The alkali metals or alkaline earth metals may be obtained by, for example, dissolving a compound in an excess alkali metal hydroxide or alkaline earth metal hydroxide solution, filtering an undissolved compound salt, and evaporating and drying the filtrate. Here, it is pharmaceutically suitable that a metal salt, particularly, a sodium, potassium or calcium salt is prepared, and in addition, a silver salt corresponding thereto may be obtained by reacting an alkali metal or alkaline earth metal salt with a suitable silver salt (e.g., silver nitrate).

The content of the protein FAM86A, agonist, activator or inhibitor thereof in the composition of the present invention can suitably adjusted according to symptoms of a disease, the degree of progression of the symptoms, and the condition of a patient, and for example, may be 0.0001 to 99.9 wt %, or 0.001 to 50 wt % based on the total weight of the composition, but the present invention is not limited thereto. The content ratio is a value based on a dry weight from which a solvent is removed.

Suitable carriers, excipients and diluents conventionally used in the preparation of the pharmaceutical composition according to the present invention may be further included. The excipients may include, for example, one or more selected from the group consisting of a diluent, a binder, a disintegrant, a lubricant, an adsorbent, a humectant, a film-coating material, and a controlled-release additive.

The pharmaceutical composition according to the present invention may be formulated in the form of a powder, a granule, a suspended-release granule, an enteric granule, a liquid, an ophthalmic solution, an elixir, an emulsion, a suspension, a spirit, a troche, aromatic water, lemonade, a tablet, a suspended-release tablet, an enteric tablet, a sublingual tablet, a hard capsule, a soft capsule, a suspended-release capsule, an enteric capsule, a pill, a tincture, a concentrate extract, a dry extract, a fluid extract, an injection, a capsule, a capsule, a perfusate, a plaster, a lotion, a paste, a spray, an inhalant, a patch, a sterile injection, or an external preparation such as an aerosol according to a conventional method, and the external preparation may have a formulation such as a cream, a gel, a patch, a spray, an ointment, a plaster, a lotion, a liniment, a liniment, a paste or a cataplasma.

The carrier, excipient and diluent which may be included in the pharmaceutical composition according to the present invention may include lactose, dextrose, sucrose, an oligosaccharide, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil.

The composition may be formulated with a diluent or an excipient such as a filler, a thickening agent, a binder, a wetting agent, a disintegrant, a surfactant, which are conventionally used.

As additives for tablets, powders, granules, capsules, pills, and troches according to the present invention, excipients such as corn starch, potato starch, wheat starch, lactose, white sugar, glucose, fructose, di-mannitol, precipitated calcium carbonate, synthetic aluminum silicate, phosphoric acid calcium monohydrogen, calcium sulfate, sodium chloride, sodium hydrogen carbonate, purified lanolin, microcrystalline cellulose, dextrin, sodium alginate, methylcellulose, sodium carboxymethylcellulose, kaolin, urea, colloidal silica gel, hydroxypropyl starch, hydroxypropyl methyl cellulose (HPMC), HPMC 1928, HPMC 2208, HPMC 2906 and HPMC 2910, propylene glycol, casein, calcium lactate, and Primojel; binders such as gelatin, gum arabic, ethanol, agar powder, phthalate acetate, carboxymethylcellulose, calcium carboxymethylcellulose, glucose, purified water, sodium caseinate, glycerin, stearic acid, sodium carboxymethylcellulose, sodium methylcellulose, methylcellulose, microcrystalline cellulose, dextrin, hydroxycellulose, hydroxypropyl starch, hydroxymethylcellulose, refined shellac, starch paste, hydroxypropylcellulose, hydroxypropylmethylcellulose, polyvinyl alcohol, polyvinylpyrrolidone, disintegrants such as hydroxypropyl methylcellulose, corn starch, agar powder, methylcellulose, bentonite, hydroxypropyl starch, sodium carboxymethylcellulose, sodium alginate, calcium carboxymethylcellulose, calcium citrate, sodium lauryl sulfate, silicic anhydride, 1-hydroxy propyl cellulose, dextran, ion exchange resins, polyvinyl acetate, formaldehyde-treated casein and gelatin, alginic acid, amylose, guar gum, sodium bicarbonate, polyvinylpyrrolidone, calcium phosphate, gelled starch, arabic rubber; disintegrants such as amylopectin, pectin, sodium polyphosphate, ethyl cellulose, sucrose, magnesium aluminum silicate, di-sorbitol liquid, and light anhydrous silicic acid; calcium stearate, magnesium stearate, stearic acid, hydrogenated vegetable oil, talc, lychee, kaolin, petrolatum, sodium stearate, cacao butter, sodium salicylate, magnesium salicylate, polyethylene glycol 4000, PEG 6000, liquid paraffin, hydrogenated soybean oil wax), aluminum stearate, zinc stearate, sodium lauryl sulfate, magnesium oxide, macrogol, synthetic aluminum silicate, silicic anhydride, higher fatty acids, higher alcohols, silicone oil, paraffin oil, polyethylene glycol fatty acid ether, starch, sodium chloride; lubricants such as sodium acetate, sodium oleate, dl-leucine, and light anhydrous silicic acid, may be used.

As an additive for the liquid according to the present invention, water, diluted hydrochloric acid, diluted sulfuric acid, sodium citrate, sucrose monostearate, polyoxyethylene sorbitol fatty acid ester (Tween ester), polyoxyethylene monoalkyl ether, lanolin ether, lanolin ester, acetic acid, hydrochloric acid, aqueous ammonia, ammonium carbonate, potassium hydroxide, sodium hydroxide, prolamine, polyvinylpyrrolidone, ethyl cellulose, or sodium carboxymethylcellulose may be used.

A syrup according to the present invention may use a solution of white sugar, other sugars or sweeteners, and if necessary, an aromatic substance, a colorant, a preservative, a stabilizer, a suspending agent, an emulsifier or a viscous agent may be used.

The emulsion according to the present invention may use purified water, and if necessary, an emulsifier, a preservative, a stabilizer or an aromatic substance may be used.

A suspension according to the present invention may use a suspending agent such as acacia, tragacanth, methyl cellulose, carboxymethylcellulose, sodium carboxymethylcellulose, microcrystalline cellulose, sodium alginate HPMC, such as HPMC 1828, HPMC 2906 or HPMC 2910, and if necessary, a surfactant, a preservative, a stabilizer, a colorant or an aromatic substance may be used.

The injection according to the present invention may include a solvent such as distilled water for injection, 0.9% sodium chloride injection, Ringer's solution, dextrose injectable solution, dextrose+sodium chloride injectable solution, PEG, lactated Ringer's solution, ethanol, propylene glycol, non-volatile oil-sesame oil, cottonseed oil, peanut oil, soybean oil, corn oil, ethyl oleic acid, isopropyl myristate or benzene benzoate; a solubilizer such as sodium benzoate, sodium salicylate, sodium acetate, urea, urethane, monoethyl acetamide, butazolidine, propylene glycol, Tween, nicotinic amide, hexamine or dimethylacetamide; a buffer such as weak acids and salts thereof (acetic acid and sodium acetate), weak bases and salts thereof (ammonia and ammonium acetate), an organic compound, a protein, albumin, peptone or gum; an isotonic agent such as sodium chloride; a stabilizer such as sodium disulfide ($NaHSO_3$) carbon dioxide gas, sodium metabisulfite ($Na_2S_2O_3$), sodium sulfite ($Na_2SO_3$), nitrogen gas ($N_2$), or ethylenediamine tetraacetic acid; an antioxidant such as 0.1% sodium bisulfide, sodium formaldehyde sulfoxylate, thiourea, disodium ethylenediamine tetraacetate or acetone sodium bisulfite; a pain-relieving agent such as benzyl alcohol, chlorobutanol, procaine hydrochloride, glucose or calcium gluconate; and a suspending agent such as CMC Na, sodium alginate, Tween 80 or aluminum monostearate.

As the suppository according to the present invention, a base such as cacao butter, lanolin, Witepsol, polyethylene glycol, glycerogelatin, methylcellulose, carboxymethylcellulose, a mixture of stearic acid and oleic acid, Subanal, cottonseed oil, peanut oil, palm oil, cacao butter+cholesterol, lecithin, Lanet wax, glycerol monostearate, Tween or Span, Imhausen, Monolen (propylene glycol monostearate), glycerin, Adeps solidus, Buytyrum Tego-G, Cebes Pharma 16, Hexalide Base 95, Cotomar, Hydrokote SP, S-70-XXA, S-70-XX75 (S-70-XX95), Hydro Hydrokote 25, Hydrokote 711, Idropostal, Massa estrarium (A, AS, B, C, D, E, I, T), Massa-MF, Masupol, Masupol-15, Neosupostal-ene, Paramound-B, Suposhiro (OSI, OSIX, A, B, C, D, H, L), suppository type IV (AB, B, A, BC, BBG, E, BGF, C, D, 299), Supostal (N, Es), Wecobee (W, R, S, M or Fs), or Tester triglyceride base (TG-95, MA, 57) may be used.

A solid formulation for oral administration is a tablet, a pill, a powder, a granule or a capsule, and such a solid formulation may be prepared by mixing at least one or more of excipients, for example, starch, calcium carbonate, sucrose, lactose or gelatin with the extract. In addition to a simple excipient, a lubricant such as magnesium stearate or talc may also be used.

As a liquid formulation for oral administration, a suspension, a liquid for internal use, an emulsion, or a syrup may be used, and a generally-used simple diluent such as water or liquid paraffin, as well as various types of excipients, for example, a wetting agent, a sweetener, an aromatic substance and a preservative may be included. A formulation for parenteral administration may be a sterilized aqueous solution, a non-aqueous solvent, a suspension, an emulsion, a lyophilized formulation or a suppository. As a non-aqueous solvent or suspension, propylene glycol, polyethylene glycol, a vegetable oil such as olive oil, or an injectable ester such as ethyl oleate may be used.

The pharmaceutical composition according to the present invention is administered at a pharmaceutically effective amount. In the present invention, the "pharmaceutically effective amount" used herein refers to an amount sufficient for treating a disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in the medical field.

The pharmaceutical composition of the present invention may be administered separately or in combination with other therapeutic agents, and may be sequentially or simultaneously administered with a conventional therapeutic agent, or administered in a single or multiple dose(s). In consideration of all of the above-mentioned parameters, it is important to achieve the maximum effect with the minimum dose without a side effect, and such a dose may be easily determined by one of ordinary skill in the art.

The pharmaceutical composition of the present invention may be administered into a subject via various routes. All administration routes may be expected, and the pharmaceutical composition of the present invention may be administered by, for example, oral administration, subcutaneous injection, intraperitoneal administration, intravenous, intramuscular or intrathecal injection, sublingual administration, buccal administration, rectal insertion, vaginal insertion, ocular administration, ear administration, nasal administration, inhalation, spraying through the mouth or nose, skin administration, or transdermal administration.

The pharmaceutical composition of the present invention is determined according to the type of a drug which is an active ingredient, as well as various parameters such as a disease to be treated, an administration route, a patient's age, gender and weight and the severity of a disease.

The "subject" used herein refers to a target requiring treatment of a disease, and is not limited as long as it is any vertebrate, but specifically, it may be applied to a human, a mouse, a rat, a guinea pig, a rabbit, a monkey, a pig, a horse, cattle, sheep, an antelope, a dog, a cat, fish and a reptile, preferably, a mammal with hair, and more preferably, a human.

The "administration" used herein refers to the provision of the composition of the present invention to a subject by a suitable method.

The "prevention" used herein refers to all actions of inhibiting or delaying the onset of a desired disease, the "treatment" used herein refers to all actions involved in improving or beneficially changing symptoms of a target disease or metabolic abnormalities thereby by the administration of the pharmaceutical composition according to the present invention, and the "alleviation" used herein refers to all actions of reducing parameters associated with a target disease, for example, the severity of a symptom.

In addition, the composition including the protein FAM86A, or an agonist or activator thereof may be contained in food for whitening.

In addition, the composition including the FAM86A inhibitor may be contained in food for alleviation of a melanin-deficient disease.

The food in the present invention includes functional food and health functional food.

Preferably, the health functional food has the advantage of a more excellent effect when ingested in the form of an inner beauty food. The inner beauty food is called an "edible cosmetic or beauty food," and makes the skin healthier due to various ingredients good for skin absorbed into the body, and when choosing cosmetics for skin type, each person can select and ingest inner beauty food suitable for each skin condition and lifestyle. More preferably, when a cosmetic product including the cosmetic composition and inner beauty food including the protein FAM86A, or an agonist or activator thereof are used together, compared with the use of only a cosmetic or drug, an exceptionally high whitening effect is exhibited, and thus a more effective skin whitening effect may be exhibited. More preferably, when a cosmetic product including the cosmetic composition and inner beauty food including the protein FAM86A are used together, compared with the use of only a cosmetic or drug, an effect of treating or alleviating melanin-deficient diseases including vitiligo and canities exceptionally increases, thereby exhibiting a more effective effect of treating or alleviating melanin-associated skin diseases.

When the protein FAM86A, or an agonist, activator or inhibitor thereof is used as a food additive, it may be used alone or in combination with another food or food ingredient and appropriately used according to a conventional method. A mixing ratio of the active ingredient may be suitably determined according to the purpose of use (prevention, health or therapeutic treatment). Generally, in the production of food or beverages, the protein FAM86A, or an agonist, activator or inhibitor thereof may be added at an amount of 15 wt % or less, and preferably 10 wt % or less, with respect to the raw materials. However, in the case of long-term intake for health and hygiene or health control, the above amount may be less than the above range, and since it has no problem in terms of safety, the active ingredient may be used in an amount more than the above range.

There are no specific limitations on the type of food. Examples of food to which the material is added may include meat, sausage, bread, chocolate, candy, snacks, confectioneries, pizza, ramen, other noodles, gum, dairy products including ice cream, various soups, beverages, tea, drinks, alcoholic beverages and vitamin complexes, and in a broad sense, all health functional foods are included.

The health drink composition according to the present invention may contain various flavoring agents or natural carbohydrates as additional ingredients like conventional beverages. Examples of the above-mentioned natural carbohydrates include conventional sugars, for example, monosaccharides such as glucose, fructose, etc.; disaccharides such as maltose, sucrose, etc.; and polysaccharides such as dextrin, cyclodextrin, etc., and sugar alcohols such as xylitol, sorbitol, erythritol, etc. As the sweetener, a natural sweetener such as thaumatin or stevia extract, or a synthetic sweetener such as saccharin or aspartame may be used. The proportion of the natural carbohydrate may be generally about 0.01 to 0.20 g, and preferably, about 0.04 to 0.10 g per 100 mL of the composition of the present invention.

In addition, the composition of the present invention may contain various nutrients, vitamins, electrolytes, flavoring agents, pectic acid and a salt thereof, alginic acid and a salt thereof, organic acids, protective colloidal thickening agents, pH adjusters, stabilizers, preservatives, glycerin, alcohol, or carbonizing agents used in soda. Other than these, the composition of the present invention may contain fruit pulp for producing natural fruit juices, fruit drinks and vegetable drinks. Such components may be used independently or in combination thereof. The proportions of these additives are not critical, but may be generally selected in the range of 0.01 to 0.20 parts by weight with respect to 100 parts by weight of the composition of the present invention.

The protein FAM86A, or agonist, activator or inhibitor thereof may be provided in the form of a cosmetic composition.

The cosmetic composition according to the present invention may be prepared in the formulation of a skin lotion, skin softener, skin toner, astringent, lotion, milk lotion, moisture lotion, nourishing lotion, massage cream, nourishing cream, moisture cream, hand cream, foundation, essence, nourishing essence, pack, soap, cleansing foam, cleansing lotion, cleansing cream, body lotion or body cleanser.

The cosmetic composition of the present invention may further include a component selected from the group consisting of a water-soluble vitamin, oil-soluble vitamin, a high-molecular weight peptide, a high-molecular weight polysaccharide and a sphingolipid.

As the water-soluble vitamin, anything that can be blended in a cosmetic product may be used, and preferably, vitamin B1, vitamin B2, vitamin B6, pyridoxine, pyridoxine hydrochloride, vitamin B12, pantothenic acid, nicotinic acid, nicotinic acid amide, folic acid, vitamin C or vitamin H may be used, and a salt thereof (thiamine hydrochloride salt or sodium ascorbate) or a derivative thereof (ascorbic acid-2-sodium phosphate, ascorbic acid-2-magnesium phosphate) is also included in the water-soluble vitamins that can be used in the present invention. The water-soluble vitamin may be obtained by a conventional method such as microbial transformation, purification of a microorganism from a cell culture, an enzymatic method, or a chemical synthesis method.

As the oil-soluble vitamin, anything that can be blended in a cosmetic product may be used, and preferably, vitamin A, carotene, vitamin D2, vitamin D3 or vitamin E (dl-alpha tocopherol, d-alpha tocopherol, d-alpha tocopherol) may be used. Derivatives thereof (ascorbyl palmitate, ascorbyl stearate, ascorbiyl dipalmitate, DL-alpha tocopherol acetate, DL-alpha tocopherol nicotinate, vitamin E, DL-pantothenyl alcohol, D-pantothenyl alcohol, pantothenyl ethylether) are also included in oil-soluble vitamins used in the present invention. The oil-soluble vitamin may be obtained by a conventional method such as microbial transformation, purification of a microorganism from a cell culture, an enzymatic method, or a chemical synthesis method.

As the high-molecular weight peptide, anything that can be blended in a cosmetic product may be used, and preferably, collagen, hydrolyzed collagen, gelatin, elastin, hydrolyzed elastin or keratin may be used. The high-molecular weight peptide may be obtained by a conventional method such as purification, an enzymatic method or chemical synthesis from a microbial cell culture, or may be generally used by purification from a natural substance such as the dermis of a pig or cattle or a silk fiber of silkworm.

As the high-molecular weight polysaccharide, anything that can be blended in a cosmetic product may be used, and preferably, hydroxyethyl cellulose, xanthan gum, sodium hyaluronate, chondroitin sulfate or a salt thereof (a sodium salt) may be used. For example, chondroitin sulfate or a salt thereof may be generally used by purification from a mammal or fish.

As the sphingolipid, anything that can be blended in a cosmetic product may be used, and preferably, a ceramide, phytosphingosine or a glycosphingolipid may be used. The sphingolipid may be generally obtained by purification from a mammal, fish, shellfish, yeast or plants according to a common method or by chemical synthesis.

In the cosmetic composition of the present invention, other components generally blended in a cosmetic product may also be added if needed, in addition to the essential component.

Other than the above components, an oil and fat component, a moisturizer, an emollient, a surfactant, organic and inorganic pigments, an organic powder, a UV absorber, a preservative, a disinfectant, an antioxidant, a plant extract, a pH adjuster, an alcohol, a pigment, an aromatic substance, a blood circulation promoter, a cooling agent, an antisudorific agent or purified water may be used.

As the oil and fat component, ester oil, hydrocarbon oil, silicone oil, fluorine oil, animal oil or vegetable oil may be added.

As the ester-type oil or fat, esters such as glyceryl tri-2-ethylhexanoate, cetyl 2-ethylhexanoate, isopropyl myristate, butyl myristate, isopropyl palmitate, ethyl stearate, octyl palmitate, isocetyl isostearate, butyl stearate, glyceryl monostearate, ethyl linoleate, isopropyl linoleate, ethyl oleate, isocetyl myristate, isostearyl myristate, isostearyl palmitate, octyldodecyl myristate, isocetyl isostearate, diethyl sebacate, diisopropyl adipate, glyceryl tri (capryl·caprate), trimethylolpropane tri-2-ethylhexanoate, trimethylolpropane triisostearate, pentaerythritol tetra-2-ethylhexanoate, cetyl caprylate, decyl laurate, hexyl laurate, decyl myristate, myristyl myristate, cetyl myristate, stearyl stearate, decyl oleate, cetyl ricinoleate, isostearyl laurate, isotridecyl myristate, isocetyl palmitate, octyl stearate, isocetyl stearate, isodecyl oleate, octyldodecyl oleate, octyldodecyl linoleate, isopropyl isostearate, stearyl 2-ethylhexanoate, cetostearyl 2-ethylhexanoate (mixture of cetyl 2-ethylhexanoate and stearyl 2-ethylhexanoate), glyceryl di-p-methoxycinnamic acid-mono-2-ethylhexanoate, hexyl isostearate, ethylene glycol dioctanoate, ethylene glycol dioleate, propylene glycol dicaprate, propylene glycol di-(capryl-caprate), propylene glycol dicaprylate, neopentylglycol dicaprate, neopentylglycol dioctanoate, glyceryl tricaprylate, glyceryl triundecylate, glyceryl triisopalmitate, glyceryl triisostearate, octyldodecyl neopentanoate, isostearyl octanoate, octyl isononanoate, hexyldecyl neodecanoate, octyldodecyl neodecanoate, isostearyl isostearate, octyldecyl isostearate, polyglycerol oleate, polyglycerol isostearate, triisocetyl citrate, triisooctyl citrate, lauryl lactate, myristyl lactate, cetyl lactate, octyldecyl lactate, triethyl citrate, acetyltriethyl citrate, acetyltributyl citrate, trioctyl citrate, diisostearyl malate, 2-ethylhexyl hydroxystearate, diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoyloxystearate, stearyl 12-stearoyloxystearate and isostearyl 12-stearoyloxystearate may be used.

As the hydrocarbon-type oil or fat, hydrocarbon-type oils or fats such as squalane, liquid paraffin, α-olefin oligomer, isoparaffin, ceresine, paraffin, liquid isoparaffin, polybutene, microcrystalline wax and Vaseline may be used.

As the silicone-type oil or fat, polymethylsilicone, methylphenylsilicone, methylcyclopolysiloxane, octamethylpolysiloxane, decamethylpolysiloxane, dodecamethylcyclosiloxane, a dimethylsiloxane-methylcetyloxysiloxane copolymer, a dimethylsiloxane-methylstearoyloxysiloxane copolymer, alkyl-modified silicone oil, or amino-modified silicone oil may be used.

As the fluorine-based oil or fat, perfluoropolyether may be used.

As the animal or plant oil or fat, animal and plant oils or fats such as avocado oil, almond oil, olive oil, sesame oil, rice bran oil, safflower oil, soybean oil, corn oil, rapeseed oil, apricot oil, palm kernel oil, palm oil, castor oil, sunflower oil, grape seed oil, cotton seed oil, coconut oil, kukui nut oil, wheat embryo oil, rice embryo oil, shea butter, evening primrose oil, macadamia nut oil, meadow foam oil, yolk oil, tallow, horse oil, mink oil, orange roughy oil, jojoba oil, candelabra wax, carnauba wax, liquid lanolin and hydrogenated castor oil may be used.

As the humectant, a water-soluble low-molecular weight humectant, an oil-soluble low-molecular weight humectant, a water-soluble polymer, or an oil-soluble polymer may be used.

As the water-soluble low-molecular weight humectant, serine, glutamine, sorbitol, mannitol, pyrrolidone-sodium carboxylate, glycerin, propylene glycol, 1,3-butylene glycol, ethylene glycol, polyethylene glycol B (degree of polymerization n=2 or more), polypropylene glycol (degree of polymerization n=2 or more), polyglycerol B (degree of polymerization n=2 or more), lactic acid or lactate may be used.

As the oil-soluble low-molecular weight humectant, cholesterol or a cholesterol ester may be used.

As the water-soluble polymer, a carboxyvinyl polymer, a polyaspartic acid salt, tragacanth, xanthan gum, methylcellulose, hydroxymethylcellulose, hydroxyethylcellulose, hydroxypropylcellulose, carboxymethylcellulose, water-soluble chitin, chitosan or dextrin may be used.

As the oil-soluble polymer, a polyvinylpyrrolidone·eicosene copolymer, a polyvinylpyrrolidone·hexadecene copolymer, nitrocellulose, dextrin fatty acid ester, or polymeric silicone may be used.

As the emollient, cholesteryl long-chain-acylglutamate, cholesteryl hydroxystearate, 12-hydroxystearic acid, stearic acid, rosic acid, lanolin fatty acid cholesteryl ester may be used.

As the surfactant, a nonionic surfactant, an anionic surfactant, a cationic surfactant, and an amphoteric surfactant may be used.

As the non-ionic surfactant, self-emulsifying glycerin monostearate, a propylene glycol fatty acid ester, a glycerol fatty acid ester, a polyglycerol fatty acid ester, a sorbitan fatty acid ester, a polyoxyethylene (POE) sorbitan fatty acid ester, a POE sorbitol fatty acid ester, a POE glycerol fatty acid ester, a POE alkyl ether, a POE fatty acid ester, POE hardened castor oil, POE castor oil, a POE·POP (polyoxypropylene) copolymer, a POE·POP alkyl ether, a polyether-modified silicone, an alkanolamide laurate, an alkylamine oxide or hydrogenated soybean phospholipid may be used.

As the anionic surfactant, a fatty acid soap, an α-acyl sulfonate, an alkyl sulfonate, an alkylallyl sulfonate, an alkylnaphthalene sulfonate, an alkyl sulfate, a POE alkyl ether sulfate, an alkylamide sulfate, an alkyl phosphate, a POE alkyl phosphate, an alkylamide phosphate, an acylalkyl taurate, an N-acyl amino acid salt, a POE alkyl ether carboxylate, an alkyl sulfosuccinate, a sodium alkylsulfoacetate, an acylated collagen hydrolyzate peptide salt, or a perfluoroalkyl phosphate may be used.

As the cationic surfactant, an alkyltrimethylammonium chloride, a stearyltrimethylammonium chloride, stearyltrimethylammonium bromide, cetostearyltrimethylammonium chloride, distearyldimethylammonium chloride, stearyldimethylbenzylammonium chloride, behenyltrimethylammonium bromide, benzalkonium chloride, diethylaminoethylamide stearate, dimethylaminopropylamide stearate or lanolin derivative quaternary ammonium salt may be used.

As the amphoteric surfactant, an amphoteric surfactant such as a carboxybetaine-type, amidobetaine-type, sulfobetaine-type, hydroxysulfobetaine-type, amidosulfobetaine-type, phosphobetaine-type, aminocarboxylic acid salt-type, imidazoline derivative-type or amidoamine-type may be used.

As the organic and inorganic pigments, inorganic pigments such as silicic acid, silicic anhydride, magnesium silicate, talc, sericite, mica, kaolin, Bengala, clay, bentonite, titanium-coated mica, bismuth oxychloride, zirconium oxide, magnesium oxide, zinc oxide, titanium oxide, aluminum oxide, calcium sulfate, barium sulfate, magnesium sulfate, calcium carbonate, magnesium carbonate, iron oxide, ultramarine, chromium oxide, chromium hydroxide, calamine and a combination thereof; organic pigments such as a polyamide, a polyester, polypropylene, polystyrene, polyurethane, a vinyl resin, a urea resin, a phenolic resin, a fluororesin, a silicon resin, an acrylic resin, a melamine resin, an epoxy resin, a polycarbonate resin, a divinylbenzene-styrene copolymer, a silk powder, cellulose, CI pigment yellow and CI pigment orange; and a composite pigment of inorganic and organic pigments may be used.

As the organic powder, metallic soap such as calcium stearate; alkylphosphate polyvalent metallic salts such as zinc sodiumcetylphosphate, zinc laurylphosphate and calcium laurylphosphate; acylamino acid polyvalent metal salts such as N-lauroyl-β-alanine calcium salt, N-lauroyl-β-alanine zinc salt and N-lauroylglycine calcium salt; amidosulfonic acid polyvalent metal salts such as N-lauroyltauline calcium salt and N-palmitoyltaurine calcium salt; N-acyl basic amino acids such as Nε-lauroyllysine, Nε-palmitoyllysine, Nα-palmitoylornitine, Nα-lauroylarginine and Nα-hardened tallow fatty acid acylarginine; N-acyl polypeptides such as N-lauroylglycylglycine; α-amino fatty acids such as α-aminocaprylic acid and α-aminolauric acid; and polyethylene, polypropylene, nylon, polymethyl methacrylate, polystyrene, a divinylbenzene-styrene copolymer and ethylene tetrafluoride may be used.

As the UV absorber, p-aminobenzoic acid, ethyl p-aminobenzoate, amyl p-aminobenzoate, octyl p-aminobenzoate, ethylene glycol salicylate, phenyl salicylate, octyl salicylate, benzyl salicylate, butylphenyl salicylate, homomenthyl salicylate, benzyl cinnamate, 2-ethoxyethyl p-methoxycinnamate, octyl p-methoxycinnamate, glyceryl di-p-methoxycinnamic acid mono-2-ethylhexanoate, isopropyl p-methoxycinnamate, a diisopropyl·diisopropyl cinnamate mixture, urocanic acid, ethyl urocanate, hydroxymethoxybenzophenone, hydroxymethoxybenzophenone sulfonate and a salt thereof, dihydroxymethoxybenzophenone, sodium dihydroxymethoxybenzophenone disulfonate, dihydroxybenzophenone, tetrahydroxybenzophenone, 4-tert-butyl-4'-methoxydibenzoylmethane, 2,4,6-trianilino-p-(carbo-2'-ethylhexyl-1'-oxy)-1,3,5-triazine, or 2-(2-hydroxy-5-methylphenyl)benzotriazole may be used.

As the disinfectant, hinokithiol, triclosan, trichlorohydroxydiphenyl ether, chlorhexidine gluconate, phenoxyethanol, resorcin, isopropylmethylphenol, azulene, salicylic acid, zinc pyrithione, benzalkonium chloride, light-sensitive pigment No. 301, mononitroguaiacol sodium or undecylenic acid may be used.

As the antioxidant, butylhydroxyanisol, propyl gallate or erythorbic acid may be used.

As the pH adjuster, citric acid, sodium citrate, malic acid, sodium malate, fumaric acid, sodium fumarate, succinic acid, sodium succinate, sodium hydroxide or disodium hydrogen phosphate may be used.

As the alcohol, a higher alcohol such as cetyl alcohol may be used.

Other than the above components, a component that can be added is not limited thereto, and any of the above-described components can be added within a range that does not damage the purpose and effect of the present invention, but is added at preferably 0.1 to 5 wt %, and more preferably 0.01 to 3 wt % with respect to the total weight.

When the formulation of the present invention is a lotion, a paste, a cream or a gel, as a carrier component, animal fiber, plant fiber, wax, paraffin, starch, tragacanth, a cellulose derivative, polyethylene glycol, silicone, bentonite, silica, talc or zinc oxide may be used.

When the formulation of the present invention is a powder or a spray, as a carrier component, lactose, talc, silica, aluminum hydroxide, calcium silicate or polyamide powder may be used, and particularly, for a spray, additionally, a propellant such as chlorofluorohydrocarbon, propane/butane or dimethyl ether may be included.

When the formulation of the present invention is a solution or an emulsion, as a carrier component, a solvent, a solubilizing agent or an emulsifier may be used, for example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or fatty acid esters of sorbitan may be used.

When the formulation of the present invention is a suspension, as a carrier component, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar or tragacanth may be used.

When the formulation of the present invention is a surfactant-contained cleanser, as a carrier component, aliphatic alcohol sulfate, aliphatic alcohol ether sulfate, sulfosuccinic acid monoester, isethionate, an imidazolinium derivative, methyltaurate, sarcosinate, fatty acid amide ether sulfate, alkyl amidobetaine, an aliphatic alcohol, fatty acid glyceride, fatty acid diethanolamide, a vegetable oil, a lanolin derivative or ethoxylated glycerol fatty acid ester may be used.

In the present specification, the composition may be prepared in one or more formulations selected from the group consisting of a shampoo, a rinse, a hair tonic, a hair nourishing toner, a hair essence, a hair serum, a scalp treatment, a hair treatment, a hair conditioner, a hair shampoo, and a hair lotion, but the present invention is not limited thereto.

The composition according to the present invention may further contain an appropriate component according to the formulation, which will be described in detail as follows.

In the present specification, any one or more selected from the group consisting of a surfactant, a preservative, a viscosity modifier, a pH adjuster, an aromatic substance, a dye, a hair conditioning agent and water may be further contained.

In the present specification, the surfactant may be any one or more selected from an anionic surfactant, an amphoteric surfactant and a non-ionic surfactant.

In the present specification, the anionic surfactant may be alkyl sulfate or alkyl ether sulfate, and specific examples of the anionic surfactants may include sodium lauryl sulfate, ammonium lauryl sulfate, triethanolamine lauryl sulfate, polyoxyethylene sodium lauryl sulfate, and polyoxyethylene ammonium lauryl sulfate.

In the present specification, the amphoteric surfactant may be alkyl betaine or alkyl amidopropyl betaine, and specific examples of the amphoteric surfactants may include cocodimethyl carboxymethyl betaine, lauryldimethyl carboxymethyl betaine, lauryldimethyl alpha-carboxyethyl betaine, cetyldimethyl carboxymethyl betaine, and cocamido propyl betaine.

In the present specification, the non-ionic surfactant may be an alkanol amide or an amine oxide, and specific examples of the non-ionic surfactants may include lauryl diethyl amine oxide, palm oil alkyl dimethyl amine oxide, lauric diethanolamide, palm oil fatty acid diethanolamide, and palm oil fatty acid monoethanolamide.

In the present specification, the preservative may be any one or more selected from the group consisting of methyl paraoxybenzoate, propyl paraoxybenzoate, sodium benzoate, methylchloroisothiazolinone, methylisothiazolinone and sodium benzoate.

In the present specification, the viscosity adjuster is any one or more selected from the group consisting of cocamide ME (CME), cocamide DEA (CDE) and sodium chloride.

In the present specification, the pH adjuster is any one or more selected from the group consisting of sodium phosphate, disodium phosphate, citric acid and sodium citrate.

In the present specification, the hair conditioning agent contains a dimethicone base, a cationic polymer or a combination thereof.

In the present specification, the hair conditioning agent may further include one or more of tertiary amidoamine, a quaternary ammonium compound, a high-melting-point compound and a silicone compound.

Specific examples of the tertiary amidoamines may include cocamidopropyl dimethylamine, stearamidopropyl dimethylamine, beheniramidopropyl dimethylamine, oleamidopropyl dimethylamine, isostearamidopropyl dimethylamine.

Specific examples of the quaternary ammonium compounds may include alkyl (C14 to C22) trimethyl ammonium chloride, dialkyl (C14 to C22) dimethyl ammonium chloride, hydrogenated tallow alkyl trimethyl ammonium chloride, and ditallow alkyl dimethyl ammonium chloride.

Specific examples of the high-melting-point compounds may include fatty alcohols, fatty acids, fatty alcohol derivatives and hydrocarbons, and more specifically, cetyl alcohol, stearyl alcohol and cetostearyl alcohol.

Specific examples of the silicone compounds may include polyalkyl siloxanes, polyacetyloxanes, polyalkyl arylsiloxanes, and polyethersiloxane copolymers.

The terms used in the present invention have been selected as currently widely used general terms in consideration of functions in the present invention, and may vary depending on the intention or practices of one of ordinary skill in the art, and the advent of new technology. In addition, in specific cases, the applicant may arbitrarily select terms, which will be defined in detail in the description of the relevant invention. Therefore, the term used in the present invention should be defined based on the meaning of the term and the overall content of the present invention, not simply based on its name.

Throughout the present specification, when one part "includes" a component, it means that it may also include other components rather than excluding components unless particularly stated otherwise. In the present specification, when one component "includes" another component, this means that, unless specifically stated otherwise, other components may be further included rather than excluded. The term "approximately" or "substantially" used herein are used at, or in proximity to, numerical values when allowable manufacturing and material tolerances, which are inherent in the stated meanings, are provided. This term is used to prevent the unfair use of the disclosures in which correct or absolute values are cited to help in understanding the present invention by unscrupulous infringers.

Throughout the present specification, the term "combination thereof" included in the Markush-type expression refers to a mixture or combination of one or more selected from the group consisting of constituents described in the Markush-type expression, that is, one or more selected from the group consisting of the components.

Hereinafter, to help in understanding the present invention, exemplary examples will be suggested. However, the following examples are merely provided to more easily understand the present invention, and not to limit the present invention.

EXAMPLES

Example 1. Cell Culture

A murine melanoma cell line, that is, B16F10 cells, was cultured in Dulbecco's modified Eagle's medium (DMEM) containing 10% fetal bovine serum (FBS) and penicillin-streptomycin in an incubator under conditions of 37° C. and 5% $CO_2$.

Example 2. Confirmation of Detection of Melanogenesis

Example 2-1. Western Blotting for Confirming UVB-Induced Melanogenesis and Protein FAM86A After C57BL/6 mice were treated with UVB (1 mJ), skin tissue was collected over time, and washed twice with PBS. And then, after completely removing PBS, 200 μL of RIPA buffer, which is a tissue lysis and staining reagent, was treated. Afterward, a protein was quantified using a BCA assay, electrophoresis was performed using 10% SDS-PAGE, the protein in the resulting PAGE gel was transferred onto a PVDF membrane, and the resulting PVDF membrane onto which the protein transfer had been completed was blocked in TBS-T (in 100 mM NaCl, 10 mM Tris, 0.1% (v/v) Tween-20, pH 7.4 PBST containing 3% BSA) at room temperature. Then, after washing three times for 10 minutes using TBS-T, a primary antibody in 3% BSA dissolved in TBS-T was treated for 1 hour, and sufficiently washed with TBS-T. In addition, a secondary antibody was treated for 1 hour, and washed three times with PBS-T for 10 minutes each. Subsequently, the amount and location of a specific protein were confirmed using an ECL detection system. The correction of the protein amount was performed by checking the amount of an actin protein by stripping the PVDF membrane, and confirming it to have the same amount as that of the protein of interest. The primary and secondary antibodies were purchased from Cell Signaling and Santa Cruz.

As shown in FIG. 1, it was confirmed that the expression level of the protein FAM86A decreased while melanogenesis proceeded by UVB. In addition, using the same sample, it was confirmed that the FAM86A expression level is inversely proportional to the amount of melanin production through Example 2-2.

Accordingly, it was confirmed that FAM86A affects melanogenesis.

Example 2-2. Confirmation of Increase in Melanogenesis Induced by UVB

After C57BL/6 mice were treated with UVB (1 mJ), skin tissue was collected over time. The obtained tissue was treated with 200 uL of cell lysis buffer to lyse the tissue, centrifuged at 4° C. and 12,000 rpm for 5 minutes, followed by removing a supernatant. The resulting pellet was treated with 100 μL of a 10% sodium dodecyl sulfate-1M NaOH solution, and heated for 30 minutes at 60° C. Afterward, the heated solution was maintained at room temperature to cool to 25° C., followed by measuring absorbance at 405 nm. Here, the amount of melanin was calculated based on 100% of the amount of melanin production in cells which had not be treated with UVB.

As shown in FIG. 1, it was confirmed that the melanin content gradually increased over time by UVB.

Example 2-3. Western Blotting for Confirming FAM86A Expression Level According to Color of Mouse Skin tissues were collected from C57BL/6 and ICR mice, and washed with PBS twice. Subsequently, PBS was completely removed, and then 200 μL of RIPA buffer, which is a tissue lysis and staining reagent, was treated. Afterward, a BCA assay was conducted to quantify proteins, and electrophoresis was performed using 10% SDS-PAGE. The protein in the resulting SDS-PAGE gel was transferred onto a PVDF membrane, and the resulting PVDF membrane onto which the protein transfer had been completed was blocked in TBS-T (in 100 mM NaCl, 10 mM Tris, 0.1% (v/v) Tween-20, pH 7.4 (PBST) containing 3% BSA) at room temperature. Then, after washing three times for 10 minutes using TBS-T, a primary antibody in 3% BSA dissolved in TBS-T was treated for 1 hour, and sufficiently washed with TBS-T. In addition, a secondary antibody was treated for 1 hour, and washed three times with PBS-T for 10 minutes each. Subsequently, the amount and location of a specific protein were determined using an ECL detection system. The correction of the protein amount was performed by checking the amount of an actin protein by stripping the PVDF membrane, and confirming it to have the same amount as that of the protein of interest. The primary and secondary antibodies were purchased from Cell Signaling and Santa Cruz.

Figure 2:
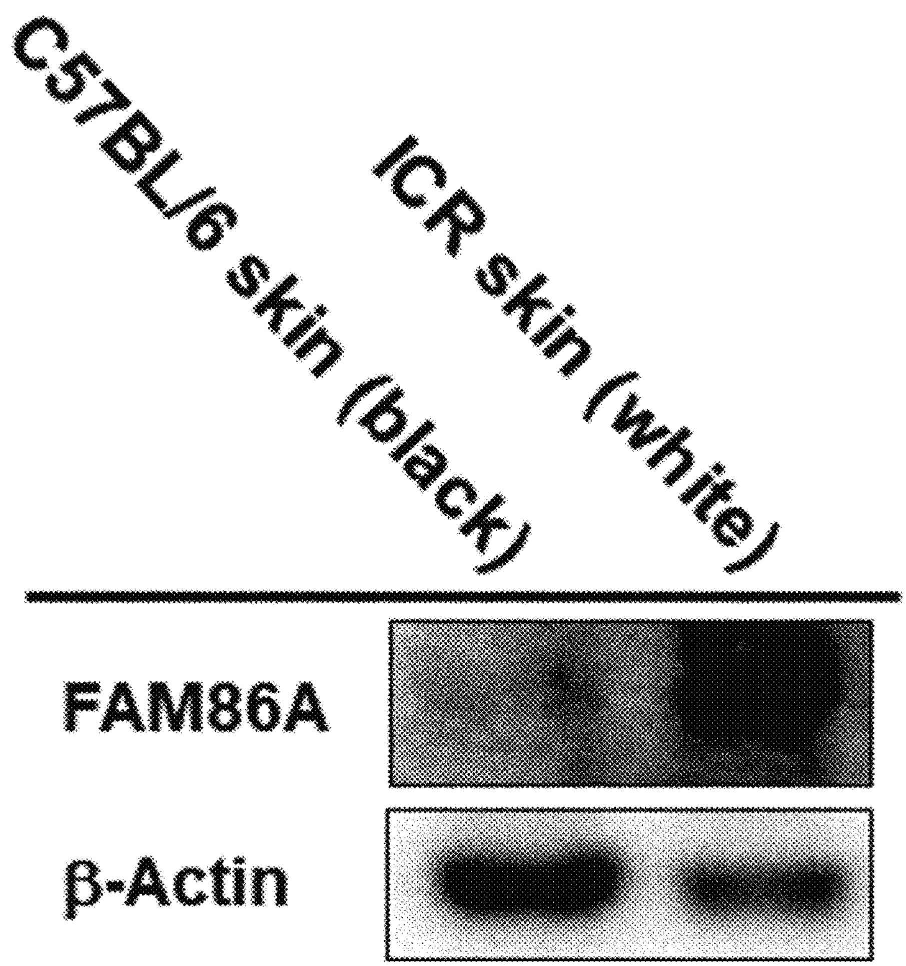
FIG. 2 shows a result of confirming FAM86A expression levels in dorsal tissue of an ICR (white-albino) rat and a C57BL/6 (black) mouse through western blotting analysis.

As shown in FIG. 2, it was confirmed that the expression level of the protein FAM86A was changed according to a skin color. Specifically, it was confirmed that FAM86A was hardly expressed in the skin of a black mouse, whereas FAM86A was highly expressed in the skin of a white mouse. These results show that FAM86A has an effect on melanogenesis.

Figure 3:
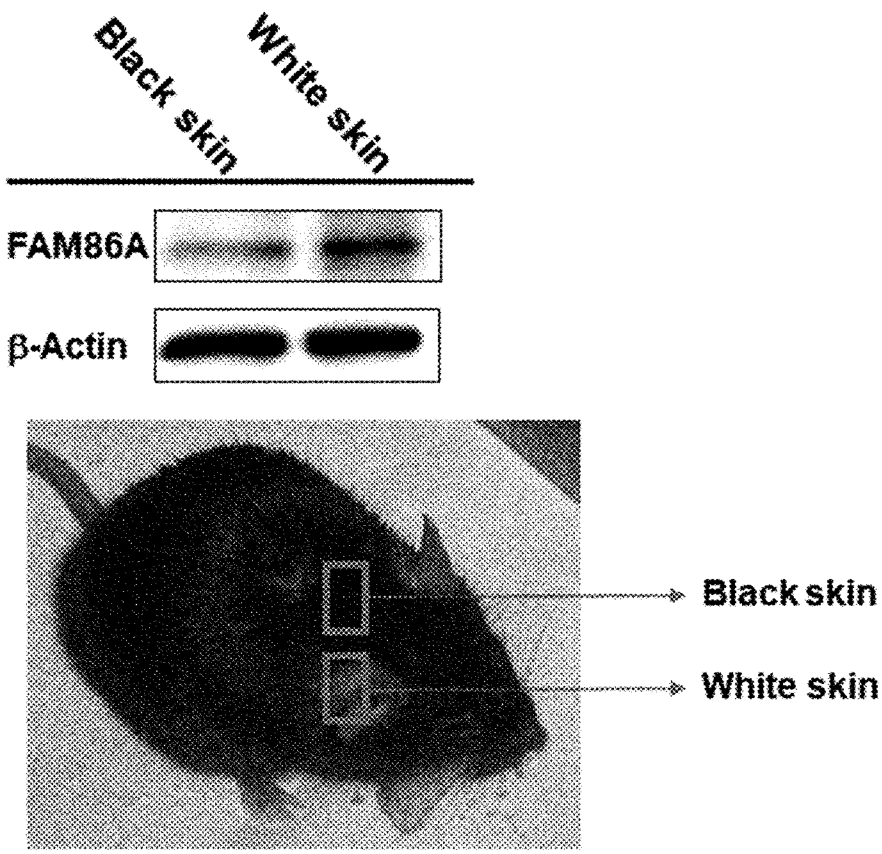
FIG. 3 shows a result of confirming FAM86A expression levels in tissues of black hairy skin (between ears) and white hairy skin (behind ears) of C57BL/6 mice through western blotting analysis.

Example 2-4. Western Blotting for Confirming FAM86A Expression Level According to Color of Site on Mouse Skin The skin tissues behind the ear (white skin) and between ears (black skin) of C57BL/6 mice were collected, and washed with PBS twice. Subsequently, PBS was completely removed, and then 200 μL of RIPA buffer, which is a tissue lysis and staining reagent, was treated. Afterward, a BCA assay was conducted to quantify proteins, and electrophoresis was performed using 10% SDS-PAGE. The protein in the resulting SDS-PAGE gel was transferred onto a PVDF membrane, and the resulting PVDF membrane onto which the protein transfer had been completed was blocked in TBS-T (in 100 mM NaCl, 10 mM Tris, 0.1% (v/v) Tween-20, pH 7.4 (PBST) containing 3% BSA) at room temperature. After washing three times with TBS-T for 10 minutes, a primary antibody in 3% BSA dissolved in TBS-T was treated for 1 hour, and then sufficiently washed with TBS-T. In addition, a secondary antibody was treated for 1 hour, and washed three times with PBS-T for 10 minutes each. Subsequently, the amount and location of a specific protein were confirmed using an ECL detection system. The result is shown in FIG. 3. The correction of the protein amount was performed by checking the amount of an actin protein by stripping the PVDF membrane, and confirming it to have the same amount as that of the protein of interest. The primary and secondary antibodies were purchased from Cell Signaling and Santa Cruz.

As shown in FIG. 3, it was confirmed that the expression level of the protein FAM86A was changed according to a skin color. Specifically, it was confirmed that FAM86A was hardly expressed in the skin tissue between ears corresponding to the black skin, whereas FAM86A was highly expressed in the white skin behind ears. These results show that FAM86A has an effect on melanogenesis.

Example 2-5. Western Blotting for Confirming Induction of Melanogenesis Induced by α-MSH and Expression Level of Protein FAM86A The B16F10 cells cultured in Example 1 were seeded in 6-well plates at a density of $5\times10^4$ cells per well, grown for 24 hours, and then treated with α-MSH at 100 nM. The cells were incubated in an incubator under conditions of 37° C. and 5% $CO_2$ for 48 hours, and washed with PBS twice. Subsequently, PBS was completely removed, and then 200 μL of RIPA buffer, which is a tissue lysis and staining reagent, was added to each plate, followed by harvesting cells with a scraper. Afterward, a BCA assay was conducted to quantify proteins, and electrophoresis was performed using 10% SDS-PAGE. The protein in the resulting SDS- PAGE gel was transferred onto a PVDF membrane, and the resulting PVDF membrane onto which the protein transfer had been completed was blocked in TBS-T (in 100 mM NaCl, 10 mM Tris, 0.1% (v/v) Tween-20, pH 7.4 (PBST) containing 3% BSA) at room temperature. After washing three times with TBS-T for 10 minutes, a primary antibody in 3% BSA dissolved in TBS-T was treated for 1 hour, and then sufficiently washed with TBS-T. In addition, a secondary antibody for 1 hour, and washed three times with PBS-T for 10 minutes each. Subsequently, the amount and location of a specific protein were confirmed using an ECL detection system. The correction of the protein amount was performed by checking the amount of an actin protein by stripping the PVDF membrane, and confirming it to have the same amount as that of the protein of interest. The primary and secondary antibodies were purchased from Cell Signaling and Santa Cruz.

Figure 4:
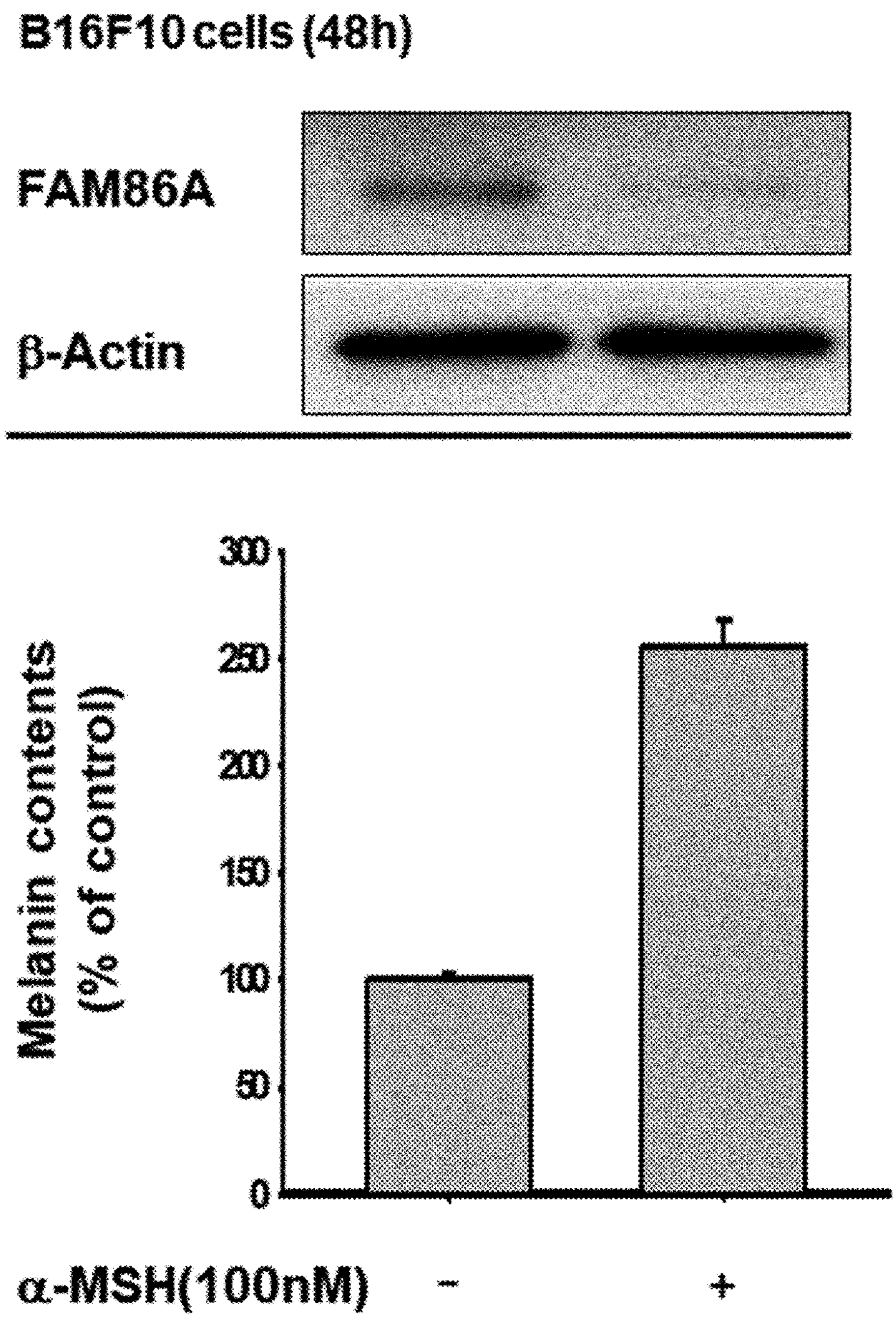
FIG. 4 shows a result of confirming a protein FAM86A expression level through western blotting analysis, after mouse melanoma cells are treated with α-MSH inducing melanogenesis (top), and a result of confirming a melanin production amount through a melanin content assay (bottom).

As shown in FIG. 4, it was confirmed that melanogenesis increased due to α-MSH, which is a melanogenesis-inducing material, and thus the expression level of the protein FAM86A decreases. Accordingly, it was confirmed that FAM86A affects melanogenesis.

Example 2-6. Confirmation of Expression Level of Melanogenesis-Associated Gene (Real-Time PCR)

The B16F10 cells cultured in Example 1 were seeded in 6-well plates at a density of $5\times10^4$ cells per well, grown for 24 hours, and then treated with α-MSH at 100 nM. The cells were incubated in an incubator under conditions of 37° C. and 5% $CO_2$ for 48 hours. After 48 hours of incubation, the medium was completely removed, the cells were decomposed with TRIzol and neutralized using BCP. The neutralized liquid was treated with isopropanol to precipitate mRNA. Subsequently, only the precipitated mRNA was collected using a centrifuge, and used for the experiment. Intracellular mRNA was synthesized into cDNA using a cDNA kit, and the expression levels of tyrosinase, TYRP-1, TYRP-2, MITF and FAM86A genes, which are important for melanogenesis, were determined by PCR.

Figure 5:
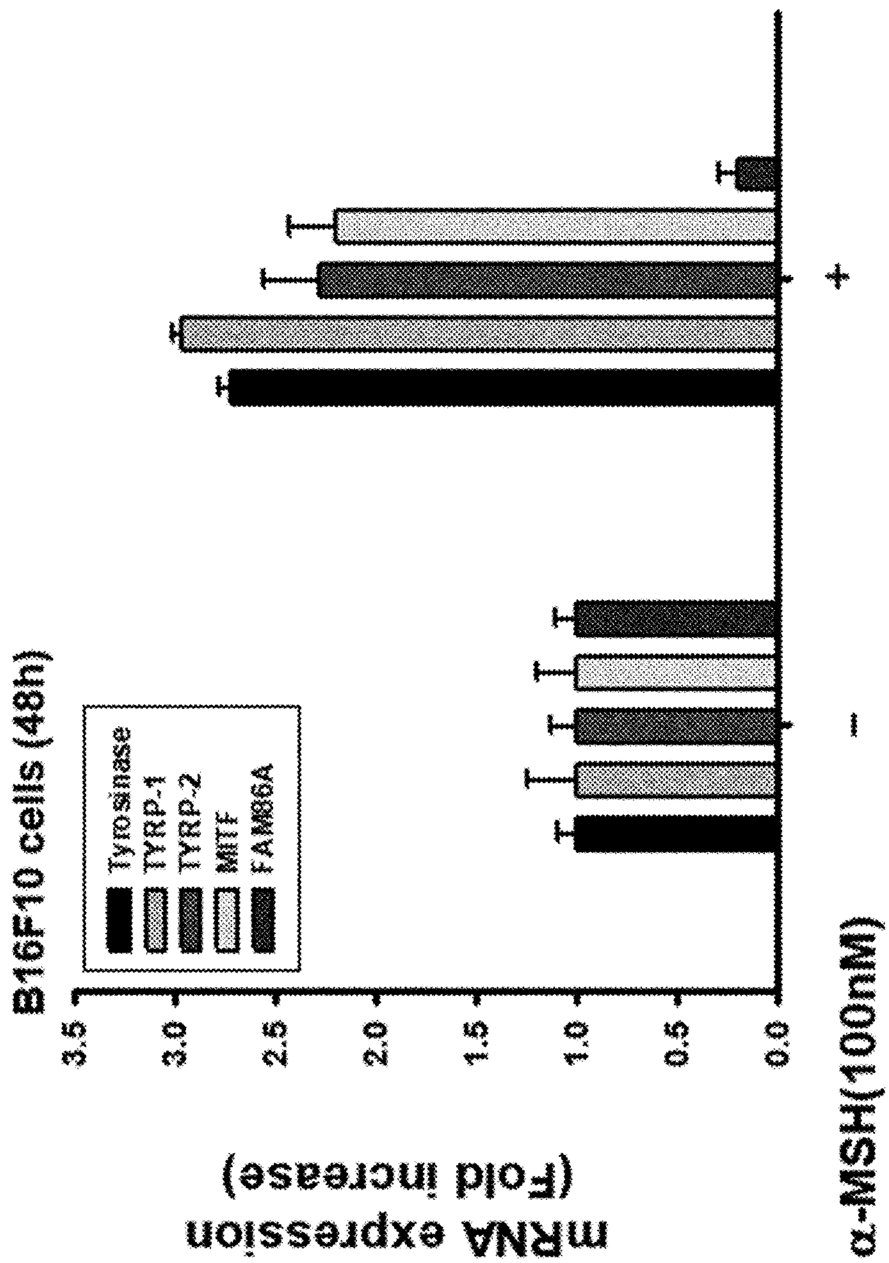
FIG. 5 shows a result of confirming expression levels of genes (tyrosinase, TYRP-1, TYRP-2 and MITF) involved in melanogenesis and a FAM86A gene through real-time PCR, after mouse melanoma cells are treated with a-MSH inducing melanogenesis.

As shown in FIG. 5, it was confirmed that the expression levels of the tyrosinase, TYRP-1, TYRP-2 and MITF genes, which are important for melanogenesis, were significantly increased by α-MSH, whereas FAM86A was decreased. Accordingly, it was seen that expression level of the FAM86A gene decreases during melanogenesis.

Example 3. Confirmation of Decrease in Melanogenesis According to FAM86A Overexpression

Example 3-1. Confirmation of cAMP Expression Level (ELISA)

For overexpression of the protein FAM86A in murine melanoma B16F10 cells, each of a vector having FAM86A represented by SEQ ID NO: 47 (pCMV Myc mFAM86A; SEQ ID NO: 46) and an empty vector (pCMV Myc; SEQ ID NO: 48) was transfected into the cells using Lipofectamine, and incubated in an incubator under conditions of 37° C. and 5% $CO_2$ for 48 hours. Afterward, the resulting cells were washed twice with PBS. Subsequently, after removing PBS completely, 200 uL of RIPA buffer, which is a cell lysis and staining reagent, was added to a plate and harvested with a scraper. And then, a BCA assay was used to quantify proteins, and cAMP protein expression was measured using a cAMP ELISA kit (ab65355).

Figure 6:
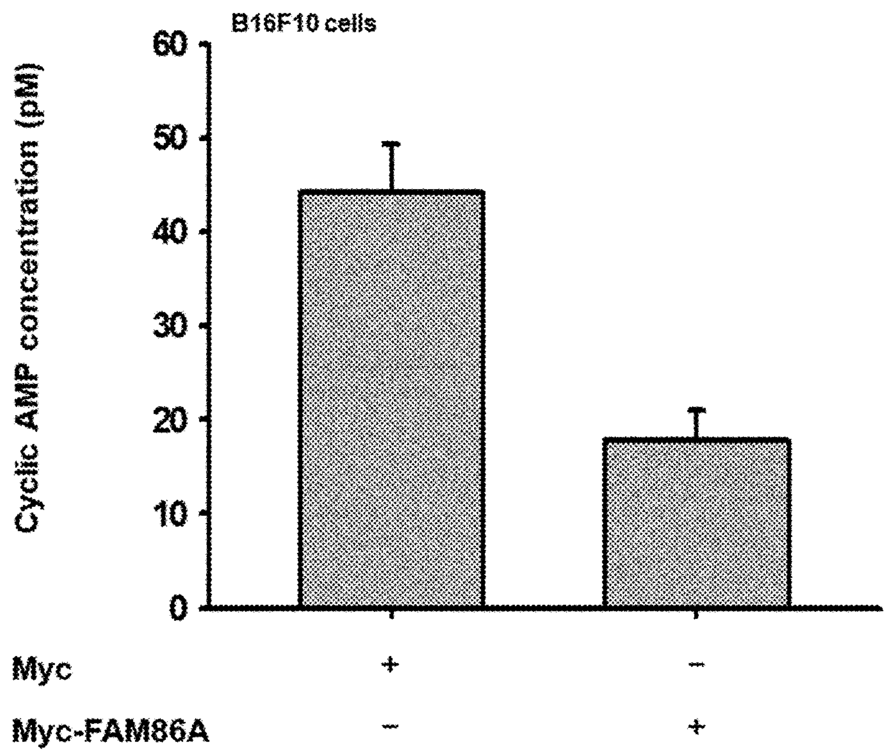
FIG. 6 shows a result of measuring an expression level of cAMP, which is a protein important for melanogenesis after FAM86A is overexpressed in mouse melanoma cells.

As a result, as shown in FIG. 6, it was confirmed that FAM86A overexpression leads to a decrease in cAMP expression.

Example 3-2. Confirmation of Effect of Reducing Melanogenesis by FAM86A Overexpression Using Fontana-Masson Staining As described in Example 3-1, Myc-FAM86A was transfected into murine melanoma B16F10 cells to overexpress FAM86A, and the degree of melanogenesis was then observed under a microscope using Fontana-Masson staining for melanin.

Specifically, the cells were cultured in an incubator under conditions of 37° C. and 5% $CO_2$ for 48 hours, and washed twice with PBS, and 1 mL of a 1% ammoniacal silver nitrate solution was added to each well, followed by heating a plate in a 60° C. dryer for 1 hour. Subsequently, the plate was washed three times with running water, and treated with 1 mL of a 0.2% gold chloride solution per well for 30 seconds. Afterward, the plate was washed twice with running water, treated with 1 mL of a 5% sodium thiosulfate solution per well, washed twice with running water, treated with 1 mL of a 0.5% neutral red solution per well for 2 minutes, and then washed with running water. The reaction result was confirmed under a microscope.

Figure 7:
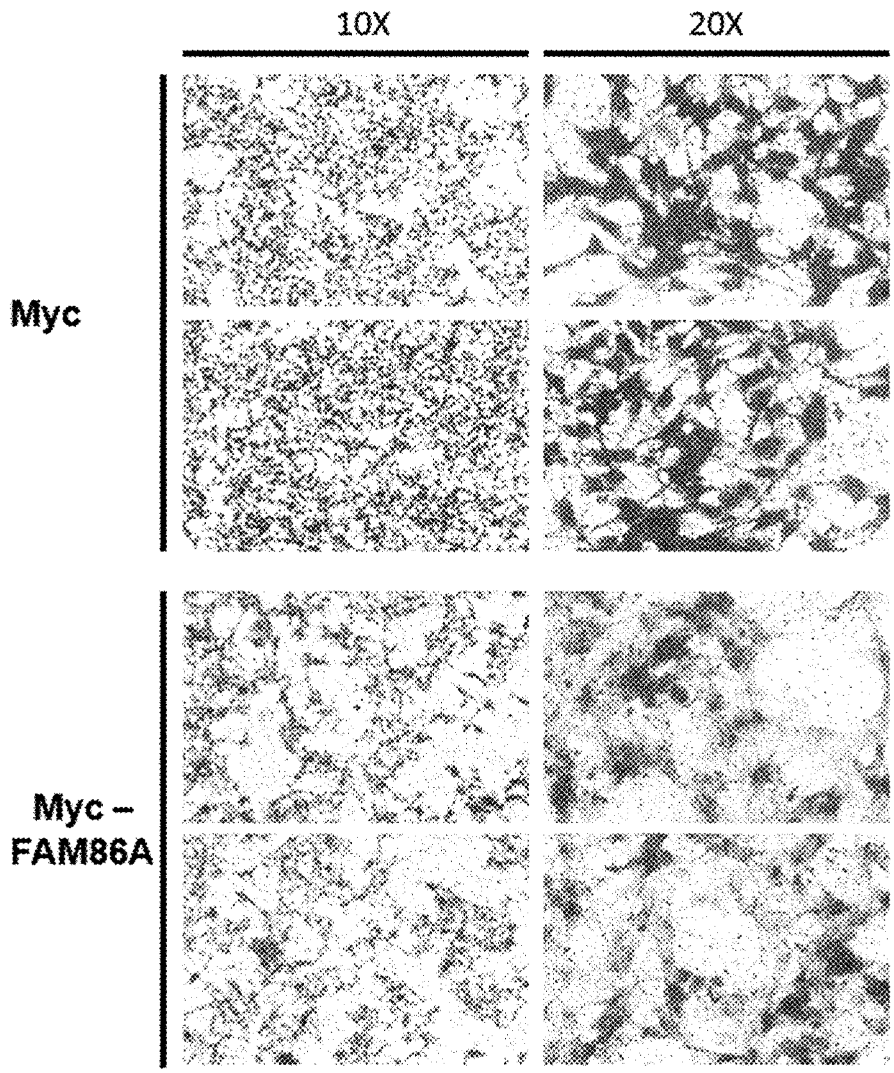
FIG. 7 shows a result of confirming melanin expression through Fontana-Masson staining after FAM86A is overexpressed in mouse melanoma cells.

As shown in FIG. 7, as a result of FAM86A overexpression, a melanin decrease was observed, compared to the control. This result showed that FAM86A overexpression leads to a decrease in intracellular and extracellular melanin.

Example 3-3. Confirmation of Decrease in Melanin Secretion by FAM86A Overexpression As described in Example 3-1, Myc-FAM86A was transfected into murine melanoma B16F10 cells to overexpress FAM86A, and the amount of melanin secretion was then confirmed by a melanin secretion assay. The cells were cultured in an incubator under conditions of 37° C. and 5% $CO_2$ for 48 hours, and then 800 μL of the cell culture fluid was transferred to a fresh tube and centrifuged at 4° C. and 12,000 rpm for 5 minutes to obtain a supernatant. 100 μL of the resulting supernatant was dispensed into a 96-well plate, and subjected to absorbance measurement at 475 nm. Here, an amount of melanin production was calculated based on 100% of the amount of melanin in cells not overexpressing the FAM86A gene.

Figure 8:
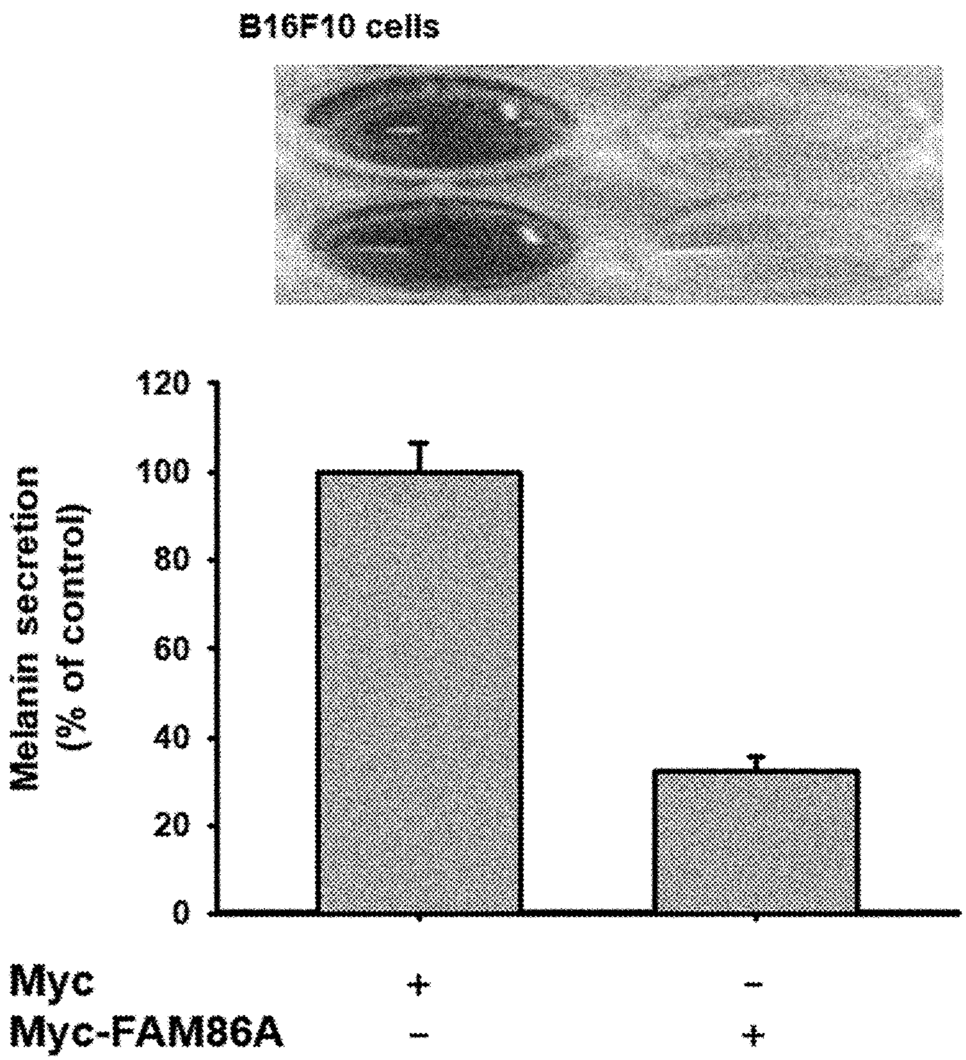
FIG. 8 shows a result of confirming a melanin secretion amount through a melanin secretion assay after FAM86A is overexpressed in mouse melanoma cells.

As shown in FIG. 8, it was confirmed that, due to FAM86A overexpression, the amount of melanin secretion was highly reduced, compared to the control. Therefore, it was confirmed that when FAM86A increased, melanin secretion decreased.

Example 3-4. Confirmation of Amount of Melanin Production by FAM86A Overexpression As described in Example 3-1, Myc-FAM86A was transfected into murine melanoma B16F10 cells to overexpress FAM86A, and the amount of melanin production was then confirmed by a melanin secretion assay. The cells were cultured in an incubator under conditions of 37° C. and 5% $CO_2$ for 48 hours, the medium was removed, and then 200 μL per well of a cell lysis buffer was added to lyse the cells, followed by centrifugation at 4° C. and 12,000 rpm for 5 minutes and removal of a supernatant. The resulting pellet was treated with 100 μL of a 10% sodium dodecyl sulfate-1M NaOH solution and heated for 30 minutes at 60° C. Afterward, the heated solution was maintained at room temperature to cool to 25° C., and absorbance at 405 nm was measured. Here, an amount of melanin production was calculated based on 100% of the amount of melanin in cells not overexpressing the FAM86A gene.

Figure 9:
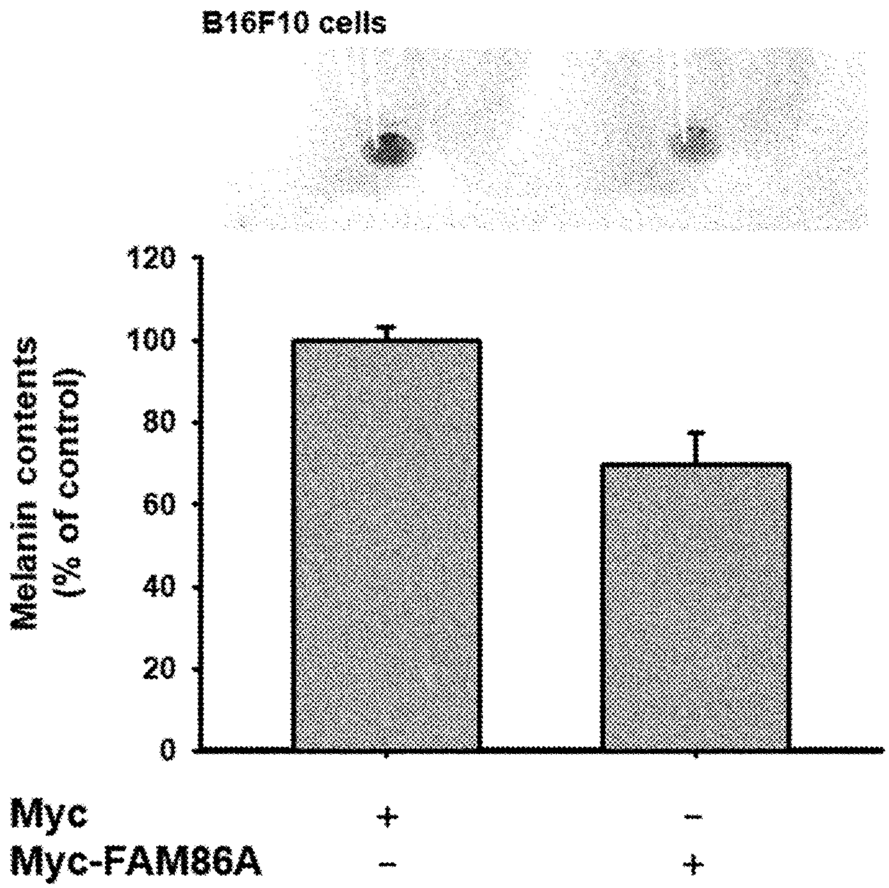
FIG. 9 shows a result of confirming a melanin production amount through a melanin secretion assay after FAM86A is overexpressed in mouse melanoma cells.

As shown in FIG. 9, it was confirmed that, due to FAM86A overexpression, the amount of melanin production was highly reduced, compared to the control. Therefore, it was confirmed that an increase in FAM86A results in a decrease in melanin secretion.

Example 3-5. Confirmation of Expression Level of Melanogenesis-Associated Gene by FAM86A Overexpression (Real Time PCR)

As shown in FIG. 3-1, Myc-FAM86A was transfected into murine melanoma B16F10 cells to overexpress FAM86A, and expression levels of genes (tyrosinase, TYRP-1, TYRP-2 and MITF) playing a pivotal role in melanogenesis were measured using real-time PCR described in Example 2-6.

Specifically, the cells were cultured in an incubator under conditions of 37° C. and 5% $CO_2$ for 48 hours. After 48 hours, the medium was completely removed, and the cells were digested with TRIzol, and neutralized with BCP. The neutralized liquid was treated with isopropanol to precipitate mRNA. Subsequently, the resulting product was centrifuged to collect only the precipitated mRNA for the experiment. Intracellular mRNA was synthesized into cDNA using a cDNA kit, and the expression levels of tyrosinase, TYRP-1, TYRP-2, MITF and FAM86A genes, which are important for melanogenesis, were determined by PCR.

Figure 10:
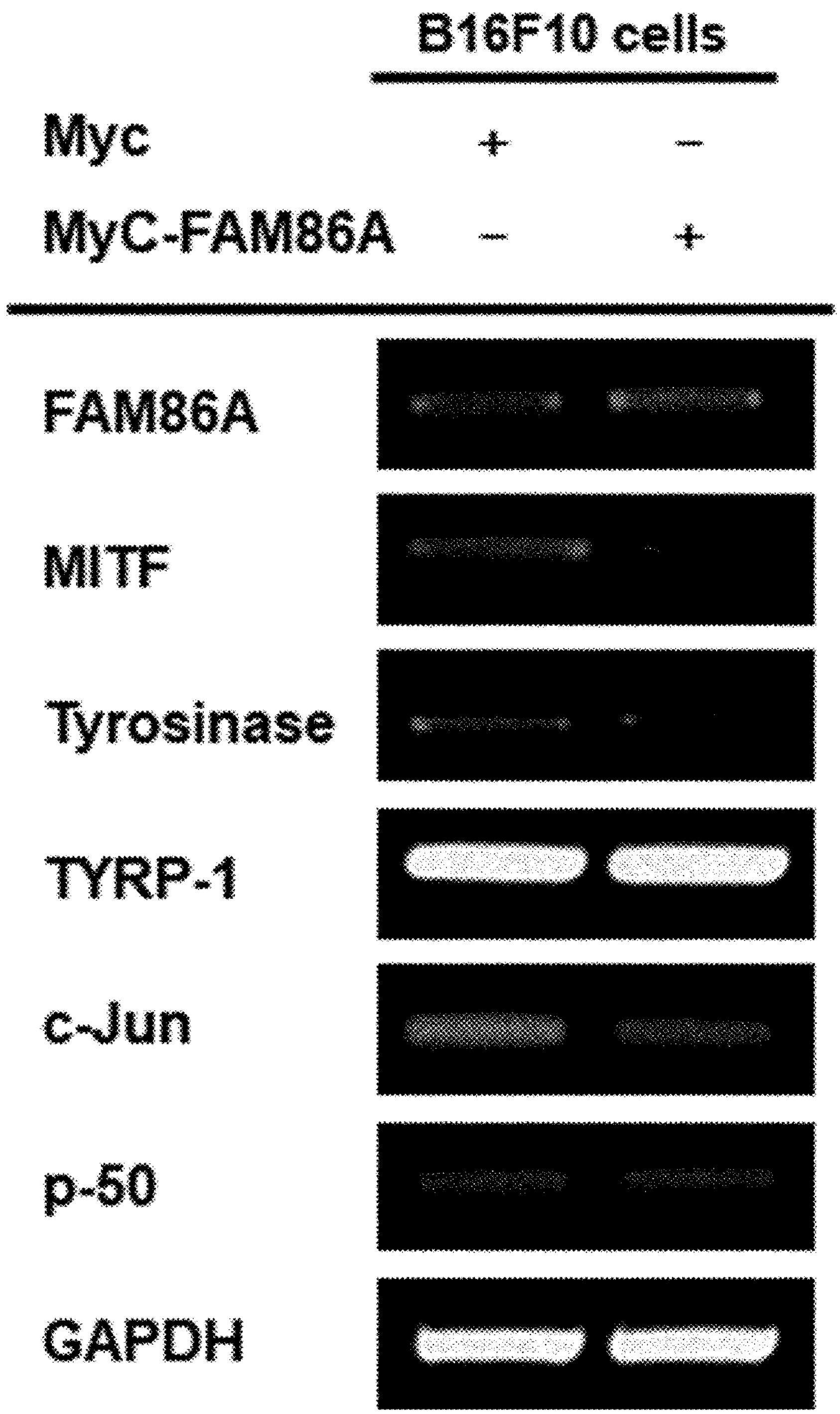
FIG. 10 shows a result of measuring expression levels of tyrosinase, TYRP-1 and MITF, which are genes important for melanogenesis, using RT-PCR, after FAM86A is overexpressed in mouse melanoma cells.

As shown in FIG. 10, it was confirmed that, by FAM86A overexpression, the melanogenesis-associated genes were downregulated. Therefore, it was confirmed that the FAM86A overexpression reduces melanogenesis not only at the protein level but also at the gene level.

Example 3-6. Confirmation of Expression Level of Melanogenesis-Associated Protein by FAM86A Overexpression (Western Blotting)

As described in Example 3-1, Myc-FAM86A was transfected into murine melanoma B16F10 cells to overexpress FAM86A, and FAM86A KID level and the expression levels of proteins of the melanogenesis-associated MAPK & MC1R signaling pathway were confirmed through western blotting described in Example 2-5.

Specifically, the cells were cultured in an incubator under conditions of 37° C. and 5% $CO_2$ for 48 hours. Afterward, the cells were washed twice with PBS. PBS was then completely removed, and 200 μL of RIPA buffer, which is a cell lysis and staining reagent, was added to each plate, and the cells were collected using a scraper. Afterward, a BCA assay was conducted to quantify proteins, and electrophoresis was performed using 10% SDS-PAGE. The protein in the resulting SDS-PAGE gel was transferred onto a PVDF membrane, and the resulting PVDF membrane onto which the protein transfer had been completed was blocked in TBS-T (in 100 mM NaCl, 10 mM Tris, 0.1% (v/v) Tween-20, pH 7.4 (PBST) containing 3% BSA) at room temperature. After washing three times with TBS-T for 10 minutes, a primary antibody in 3% BSA dissolved in TBS-T was treated for 1 hour, and then sufficiently washed with TBS-T. In addition, a secondary antibody was treated for 1 hour, and washed three times with PBS-T for 10 minutes each. Subsequently, the amount and location of a specific protein were confirmed using an ECL detection system. The correction of the protein amount was performed by checking the amount of an actin protein by stripping the PVDF membrane, and confirming it to have the same amount as that of the protein of interest. The primary and secondary antibodies were purchased from Cell Signaling and Santa Cruz.

Figure 11:
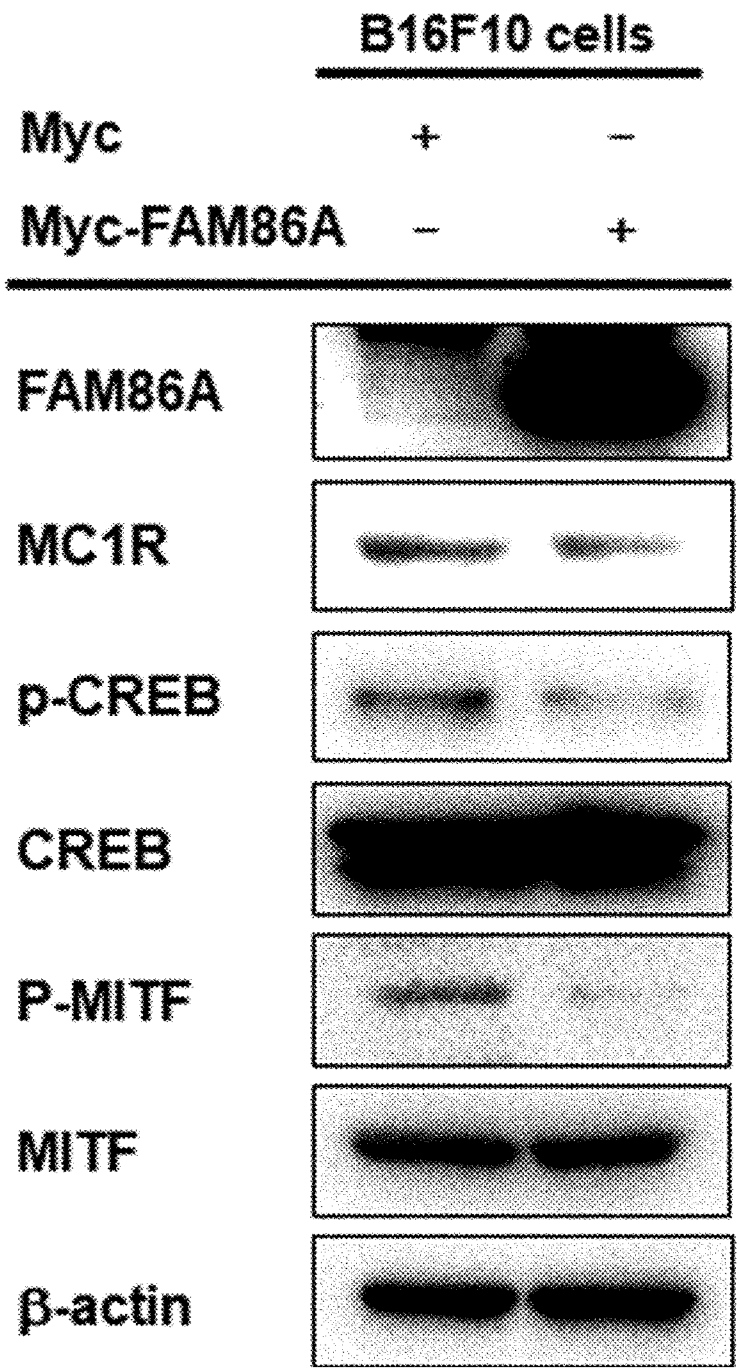
FIG. 11 shows a result of measuring expression levels of MC1R, p-CREB and MITF, which are proteins of a MAPK and MC1R signaling pathway, through western blotting, after FAM86A is overexpressed in mouse melanoma cells.

As shown in FIG. 11, it was confirmed that the expression levels of MC1R, p-CREB and MITF proteins, which are proteins of the MC1R signaling pathway, were significantly reduced by the FAM86A overexpression. From the above result, it was confirmed that the higher the FAM86A expression, the lower the activity of MC1R, which is a melanogenesis signaling pathway, confirming that increased FAM86A reduces melanogenesis.

Example 4. Confirmation of Increase in Melanogenesis According to FAM86A Knockdown

Example 4-1. Confirmation of Increase in Melanogenesis in α-MSH-Induced Melanocytes A melanocyte stimulating hormone (α-MSH), which is a melanin synthesis promoting hormone, was used to induce melanogenesis in melanocytes.

Figure 12:
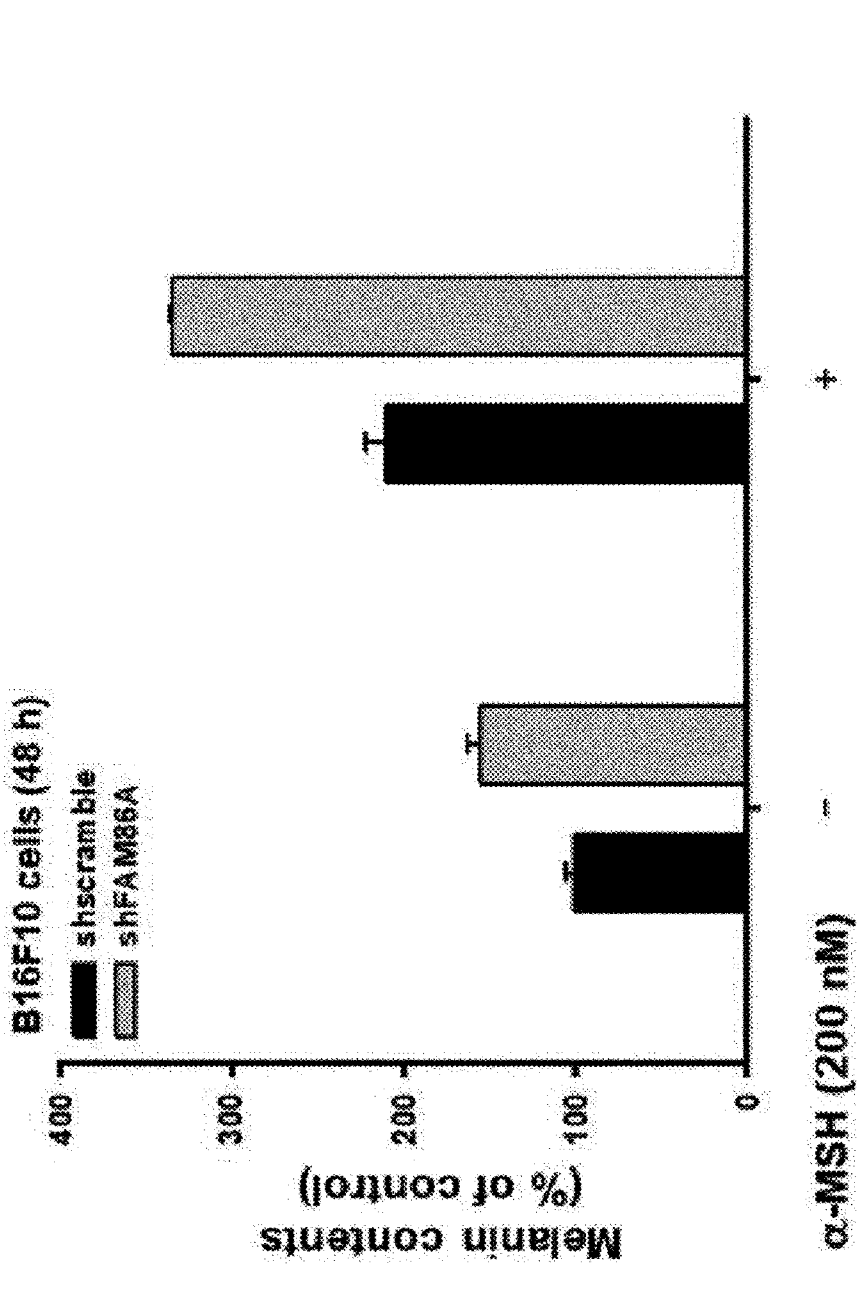
FIG. 12 shows a result of confirming a melanin production amount through a melanin content assay by subjecting mouse melanoma cells to knockdown of FAM86A using shRNA and then treating them with α-MSH promoting melanogenesis.

The B16F10 cells cultured in Example 1 were seeded in 6-well plates at a density of $5\times10^4$ cells per well, grown for 24 hours, and FAM86A shRNA represented by SEQ ID NO: 17 in Table 1 was used for knockdown of the FAM86A gene. The cells were treated with α-MSH to be 100 nM. The resulting cells were cultured in an incubator under conditions of 37° C. and 5% $CO_2$ for 48 hours, the medium was removed, and a cell lysis buffer was treated at 200 μL per well to lyse the cells, followed by centrifugation at 4° C. and 12,000 rpm for 5 minutes and removal of a supernatant. The resulting pellet was treated with 100 μL of a 10% sodium dodecyl sulfate-1M NaOH solution and heated for 30 minutes at 60° C. Afterward, the heated solution was maintained at room temperature to cool to 25° C., absorbance at 405 nm was measured, and the results are shown in FIG. 12. Here, an amount of melanin production was calculated based on 100% of the amount of melanin in cells not treated with α-MSH.

As shown in FIG. 12, it was confirmed that, the increased amount of melanin by the treatment with α-MSH, which is a melanin synthesis promoting enzyme, is increased in a FAM86A-knockdown group. Therefore, it was seen that melanogenesis can be increased by FAM86A suppression.

TABLE 1 shRNA (*Homo sapiens*, *Mus musculus*) sequences and target sequences of FAM86A (the shRNA sequences used in the examples are shown in bold)

| Species | shRNA No. | Gene | NCBI accession No. | shRNA sequence | Target sequence | Vector | Mean Knock down level |
|---|---|---|---|---|---|---|---|
| *Homo sapiens* | 1 | FAM86A | NM_201400.4 | CCGGGCAGAAACTGTTTCCCTACGACTC GAGTCGTAGGGAAACAGTTTCTGCTTTT TG (SEQ ID NO: 11) | GCAGAAACTGTT TCCCTACGA (SEQ ID NO: 21) | pLKO.1 | 0.93 |
| | 2 | FAM86A | NM_201400.4 | CCGGCGAGGGAATGTCCTTCTCAATCTC GAGATTGAGAAGGACATTCCCTCGTTTT TG (SEQ ID NO: 12) | CGAGGGAATGT CCTTCTCAAT (SEQ ID NO: 22) | pLKO.1 | 0.84 |
| | 3 | FAM86A | NM_201400.4 | CCGGGATGTTGTCATTGCAGCAGATCTC GAGATCTGCTGCAATGACAACATCTTTT TG (SEQ ID NO: 13) | GATGTTGTCATT GCAGCAGAT (SEQ ID NO: 23) | pLKO.1 | 0.79 |
| | 4 | FAM86A | NM_201400.4 | CCGGGCCAGCAGTTCTGGTTCTTAACTC GAGTTAAGAACCAGAACTGCTGGCTTTT TG (SEQ ID NO: 14) | GCCAGCAGTTCT GGTTCTTAA (SEQ ID NO: 24) | pLKO.1 | 0.77 |
| | 5 | FAM86A | NM_201400.4 | CCGGGCAGACATCACTGCCAAGTTACTC GAGTAACTTGGCAGTGATGTCTGCTTTT TG (SEQ ID NO: 15) | GCAGACATCACT GCCAAGTTA (SEQ ID NO: 25) | pLKO.1 | 0.6 |
| *Mus musculus* | 1 | FAM86 | NM_027446.2 | CCGGGAGCATTCAGCCATCGTAATCCTC GAGGATTACGATGGCTGAATGCTCTTTT TG (SEQ ID NO: 16) | GAGCATTCAGCC ATCGTAATC (SEQ ID NO: 26) | pLKO.1 | 0.56 |
| | **2** | **FAM86** | **NM_027446.2** | **CCGGGTCTATGTAGCCTATACTATCCTC GAGGATAGTATAGGCTACATAGACTTTT TG** (SEQ ID NO: 17) | **GTCTATGTAGC CTATACTATC** (SEQ ID NO: 27) | **pLKO.1** | **0.87** |
| | 3 | FAM86 | NM_027446.2 | CCGGGCCTTACAGGCCTGGCAATTTCTC GAGAAATTGCCAGGCCTGTAAGGCTTTT TG (SEQ ID NO: 18) | GCCTTACAGGCC TGGCAATTT (SEQ ID NO: 28) | pLKO.1 | unverified |
| | 4 | FAM86 | NM_027446.2 | CCGGACGGACCTTCTGTGAAGTATGCTC GAGCATACTTCACAGAAGGTCCGTTTTT G (SEQ ID NO: 19) | ACGGACCTTCTG TGAAGTATG (SEQ ID NO: 29) | pLKO.1 | unverified |
| | 5 | FAM86 | NM_027446.2 | CCGGGTTGTCATTGCAGCAGATGTACTC GAGTACATCTGCTGCAATGACAACTTTT TG (SEQ ID NO: 20) | GTTGTCATTGCA GCAGATGTA (SEQ ID NO: 30) | pLKO.1 | unverified |

TABLE 2 siRNA (*Homo sapiens*) target sequences of FAM86A

| Species | siRNA No. | Gene | NCBI accession No. | siRNA target sequence |
|---|---|---|---|---|
| *Homo sapiens* | 1 | FAM86A | NM_201400.4 | aactcttgctgcagagttt (SEQ ID NO: 31) |
| | 2 | FAM86A | NM_201400.4 | cttagaagcaaagttaaga (SEQ ID NO: 32) |
| | 3 | FAM86A | NM_201400.4 | ttaagagactcatcagatt (SEQ ID NO: 33) |
| | 4 | FAM86A | NM_201400.4 | tctcaatggcctctcatta (SEQ ID NO: 34) |
| | 5 | FAM86A | NM_201400.4 | gaatgtttggagaatgtta (SEQ ID NO: 35) |
| *Mus musculus* | 1 | FAM86A | NM_027446 | AAGAGCATTCAGCCATCGTAA (SEQ ID NO: 36) |
| | 2 | FAM86A | NM_027446 | AAGATGCTCGAGGACTGCCAG (SEQ ID NO: 37) |

TABLE 2-continued

| siRNA (*Homo sapiens*) target sequences of FAM86A | | | | |
|---|---|---|---|---|
| Species | siRNA No. | Gene | NCBI accession No. | siRNA target sequence |
| | 3 | FAM86A | NM_027446 | AACTCAGTTACACTCTCTGAG (SEQ ID NO: 38) |
| | 4 | FAM86A | NM_027446 | AAACTCAGTTACACTCTCTGA (SEQ ID NO: 39) |

TABLE 3

| miRNA (*Homo sapiens*, *Mus musculus*) sequences and target sequences of FAM86A | | | | | | |
|---|---|---|---|---|---|---|
| Species | miRNA | miRNA target gene | miRNA target region | miRNA sequence | miRNA target sequence | Reference |
| *Homo sapiens* | miR-145 | FAM86A | 397-404 of 3' UTR | caccttgtcctcacggtccagtatcccaggaatcccttagaggaatc atgctaagatggggattcctggaaatactgacttgaggtc atggtttggaaatactgttcttgagg tcatggtt (SEQ ID NO: 40) | | Integrated MicroRNA-mRNA profiling identifies oncostatin M as a marker of mesenchymal-like Er-negative/HER2-negative breast cancer, Target scan human_prediction of microRNA targets |
| | miR-204 | FAM86A | 767-773 of 3' UTR | ggctacagtattcttcatgtgactcgtggacttccattgtaaaggga catcctatgcctgagaatatatgaaggaggctgggaaggc aaagggacgttcaattgtcatcactggc (SEQ ID NO: 41) | | Target scan human_prediction of microRNA targets |
| | miR-211 | FAM86A | 767-773 of 3' UTR | tcacctggccatgtgacttgtgggcttccattgtcatcctaaaggga tcgcctagggctctgagcagggcagggacagcaaagggg tgctcagttgtcacttcccacagcacggag (SEQ ID NO: 42) | | Target scan human_prediction of microRNA targets |
| *Mus musculus* | miR-370 | FAM86 | 796-802 of 3' UTR | agacggagagaccaggtcacgtctctgcagttacacagc cagcagg tcatgagtgcctgctggggtggaacctggtttgtctgtct (SEQ ID NO: 43) | | Target scan mouse_prediction of microRNA targets |
| | miR-290 | FAM86 | 813-819 of 3' UTR | ctcatcttgcggtactcaaactatgggggcactttttttttttgaga ttctttaaaaagtgccgcctagttnaagccccgccggttg ag (SEQ ID NO: 44) | | Target scan mouse_prediction of microRNA targets |
| | miR-292 | FAM86 | 813-819 of 3' UTR | cagcctgtgatactcaaactgggggctcattggattttcatttgaga tcggaagaaaagtgccgccaggttttgagtgtcaccggtt g (SEQ ID NO: 45) | | Target scan mouse_prediction of microRNA targets |

TABLE 4

| Sequences (*Homo sapiens*, *Mus musculus*) of FAM86 family | | | |
|---|---|---|---|
| Species | Gene | *NCBI* accession No. | Sequence |
| *Homo sapiens* | FAM86A | NM_201400.4 (SEQ ID NO: 6) | atggcgcccgaggagaacgcggggaccgaactcttgctgcagagtttcgagcgccgcttcctggcggcacgcaca ctgcgctccttcccctggcagagcttagaagcaaagttaagagactcatcagattctgagctgctgcgggatatt ttgcacaagactgtgaagcatcctgtgtgtgtgaagcacccgccgtccgtcaaatatgcccggtgctUctctcag aactcatcaaaaagcacgaggctgtccacacagagcctttggacgagctgtatgaagcgctggcggagaccctga tggccaaggagtccacccagggccaccggagctatttgctgccctcgggaggctcggtcacactctccgagagca cggccatcatctcctacggtaccacaggcctggtcacatgggacgccgccctctaccttgcagaatgggccatcg agaacccggcagtcttcactaacaggactgtcctagagcttggcagtggtgctggcctcacaggcctggccatct gcaagatgtgccgcccccgggcatacatcttcagcgactgtcacagccgggtccttgagcagctccgagggaatg tccttctcaatggcctctcattagaggcagacatcactgccaagttagacagccccagggtgacagtggcccagc tggactgggacgtcgcgacggtccatcagctctctgccttccagccagatgttgtcattgcagcagatgtgctgt |

TABLE 4-continued

| Sequences (*Homo sapiens, Mus musculus*) of FAM86 family | | | |
|---|---|---|---|
| Species | Gene | *NCBI* accession No. | Sequence |
| | | | attgcccagaagccatcatgtcgctggtcggcgtcctgcggaggctggctgcctgccgggagcaccagcgggctc ctgaggtctacgtggcctttaccgtccgcaacccagagacgtgccagctgttcaccaccgagctaggccgggccg ggatcagatgggaagtggaacctcgtcatgagcagaaactgtttccctacgaagagcacttggagatggcaatgc tgaatctcaccctgtag |

TABLE 5

| | Amino acid Sequence |
|---|---|
| FAM86A (NP_958802.1) | mapeenagtelllqsferrflaardrsfpwqsleaklrdssdsellrdilhktvkhpvcvkhppsvkyarcflseli kkheavhtepldelyealaetlmakestqghrsyllpsggsvtlsestaiisygttglvtwdaalylaewaienpa vftnrtvlelgsgagltglaickmcrprayifsdchsrvleqlrgnvllnglsleaditakldsprvivaqldwdvat vhqlsafqpdvviaadvlycpeaimslvgvlrrlaacrehqrapevyvaftvrnpetcqlfttelgragirweve prheqklfpyeehlemamlnltl (SEQ ID NO: 1) |
| FAM86B1 (NP_001077006.1) | mapeenagtelllqgferrflavrtlrsfpwqsleaklrdssdsellrdilqktvrhpvcvkhppsykyawcflse likkssggsvdskstaiishgttglvtwdaalylaewaienpaafinrtvlelgsgagltgla ickmcrprayifsdphsrvleqlrgnyllnglsleaditgnldsprvivaqldwdvamvhqlsafqpdvviaad vlycpeaivslvgvlq rlaacrehkrapevyvaftvmpetcqlfttelgrdgirweaeahhdqklfpygehlemamlntl (SEQ ID NO: 2) |
| FAM86B2 (NP_001131082.1) | mapeenagtelllqgferrflavrtlrsfpwqsleaklrdssdsellrdilqktvrhpvcvkhppsykyawcflse likkheavhtepldklyevlaetlmakestqghrsyllssggsvtlskstaiishgttglvtwdaalylaewaienp aafinrtvlelgsgagltglaickmcrprayifsdphsrileqlrgnvllnglsleaditgnldsprvtvaqldwdva mvhqlsafqpdvviaadvlycpeaivslvgvlqrlaacrehkrapevyvaftvmpetcqlfttelgrdgirwea eahhdqklfpygehlemamlnltl (SEQ ID NO: 3) |
| FAM86C1 (NP_060642.2) | mapeenagselllqsfkrrflaaralrsfrwqsleaklrdssdsellrdilqkheavhtepldelyevlvetlmake stqghrsylltcciaqkpscrwsgscggwlpagstsgllnstwplpsatqrcascsppsyaglgsdgkrklimtr ncfptestwrwqs (SEQ ID NO: 4) |
| FAM86 (NP_081722.1) | mapedhegatsllqsferrflaaralpsfpwqsleeklkdpsgselllailqrtvkhpvcvqhgpsvkyarcflsk likkheavptepldalyealaevlmtqestqchrsyllpsgnsvtlsestaivshgttglvtwdaalylaewaien paaftdrtilelgsgagltglaickaccprayifsdchaqvleqlrgnvllngfslephtpidagsskvtvaqldwd evtasqlsafqadvviaadvlycwemtlslvrvlkmledcqrksapdvyvaytirsqdtgklfieeldragiyw eevpphtgklfpyeehsaivilklvltsrhgv (SEQ ID NO: 5) |

Example 4-2. Confirmation of Increased Melanin Secretion in α-MSH-Induced Melanocytes The melanin synthesis promoting hormone α-MSH was used to induce melanogenesis in melanocytes.

The B16F10 cells cultured in Example 1 were seeded in a 6-well plate at $5\times10^4$ cells/well and cultured for 24 hours, FAM86A (family with sequence similarity 86, member A) shRNA represented by SEQ ID NO: 17 was used for knockdown of the FAM86A gene, and then the cells were treated with α-MSH at 100 nM. The resulting cells were cultured in an incubator under conditions of 37° C. and 5% $CO_2$ for 48 hours, and 800 μL of the cell culture fluid was transferred to a fresh tube, and centrifuged at 4° C. and 12,000 rpm for 5 minutes to obtain a supernatant. 100 μL of the resulting supernatant was dispensed into a 96-well plate, and subjected to absorbance measurement at 475 nm. Here, an amount of melanin production was calculated based on 100% of the amount of melanin in cells not treated with α-MSH.

Figure 13:
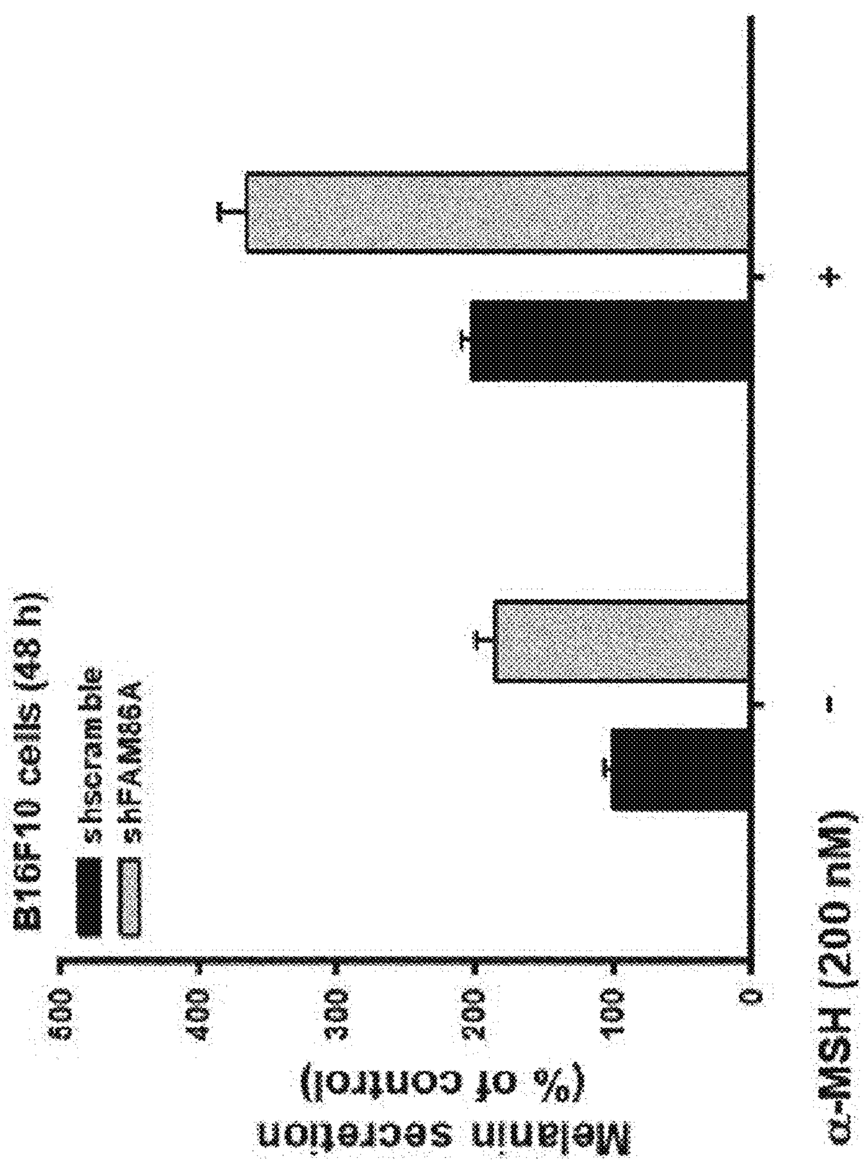
FIG. 13 shows a result of confirming a melanin secretion amount through a melanin secretion assay by subjecting mouse melanoma cells to knockdown of FAM86A using shRNA and then treating them with α-MSH promoting melanogenesis.

As shown in FIG. 13, it was confirmed that the secretion amount of melanin whose production is increased by treatment with the melanin synthesis promoting enzyme α-MSH is increased in a FAM86A-knockdown group. Therefore, it was seen that melanin secretion is increased by FAM86A suppression.

Example 4-3. Confirmation of Increase in Melanogenesis According to FAM86A Knockdown The B16F10 cells cultured in Example 1 were seeded in a 6-well plate at $5\times10^4$ cells/well and cultured for 24 hours, and the knockdown of the FAM86A gene was induced using FAM86A shRNA represented by SEQ ID NO: 17. The cells were cultured in an incubator under conditions of 37° C. and 5% $CO_2$ for 48 hours, the medium was removed, and then a cell lysis buffer was added at 200 μL per well to lyse the cells, followed by centrifugation at 4° C. and 12,000 rpm for 5 minutes and removal of a supernatant. The resulting pellet was treated with 100 μL of a 10% sodium dodecyl sulfate-1M NaOH solution, and heated for 30 minutes at 60° C. Afterward, the heated solution was maintained at room temperature to cool to 25° C., and absorbance at 405 nm was measured. Here, an amount of melanin production was calculated based on 100% of the amount of melanin in cells in which the FAM86A gene was not knocked down.

Figure 14:
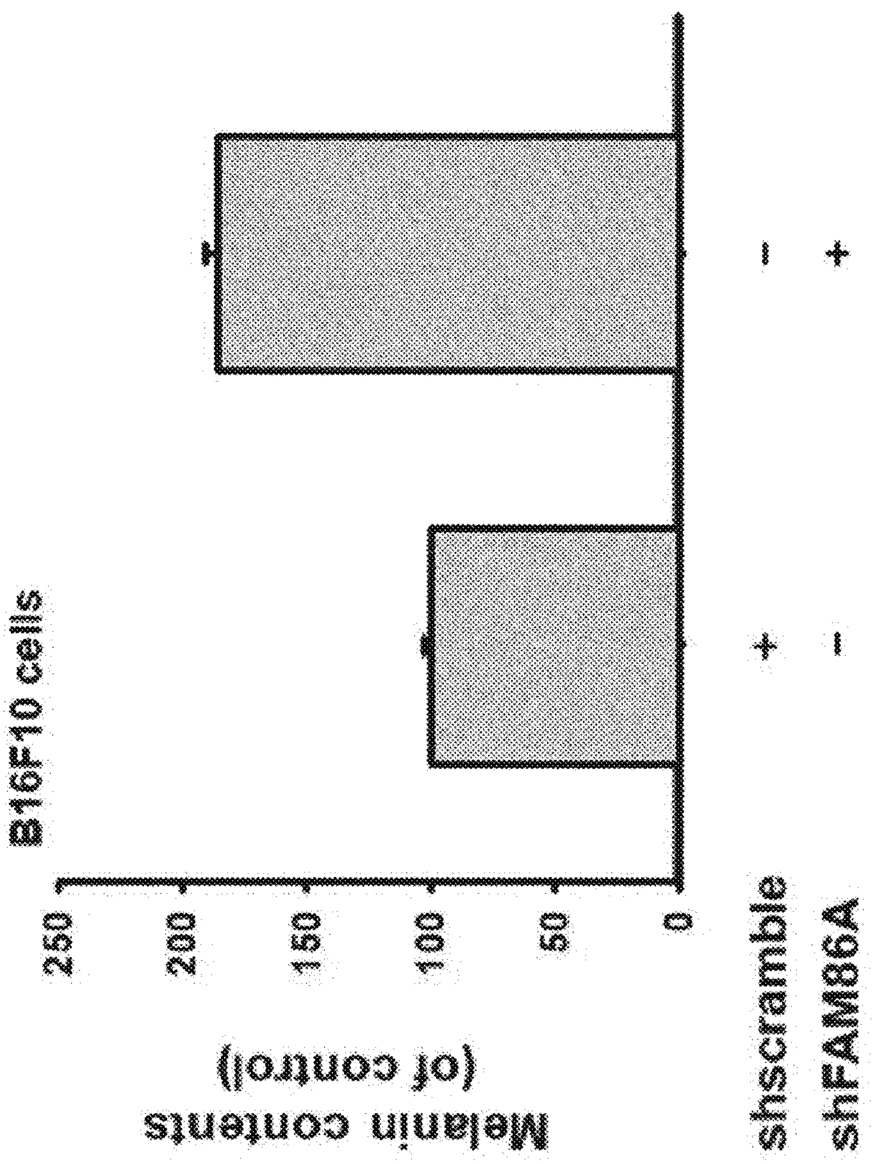
FIG. 14 shows a result of confirming a melanin production amount through a melanin content assay after mouse melanoma cells are subjected to knockdown of FAM86A using shRNA.

As shown in FIG. 14, it was confirmed that the amount of melanin was increased in the FAM86A-knockdown group. Therefore, it was seen that melanogenesis was increased by FAM86A suppression.

Example 4-4. Confirmation of Increased Melanin Secretion According to FAM86A Knockdown The B16F10 cells cultured in Example 1 were seeded in a 6-well plate at $5\times10^4$ cells/well and cultured for 24 hours, and the knockdown of the FAM86A gene was induced using FAM86A shRNA represented by SEQ ID NO: 17. The cells were cultured in an incubator under conditions of 37° C. and 5% $CO_2$ for 48 hours, the medium was removed, and then a cell lysis buffer was added at 200 μL per well to lyse the cells, followed by centrifugation at 4° C. and 12,000 rpm for 5 minutes and removal of a supernatant. 100 μL of the resulting supernatant was dispensed into a 96-well plate, and subjected to absorbance measurement at 475 nm. Here, an amount of melanin secretion was calculated based on 100% of the amount of melanin in cells in which the FAM86A gene was not knocked down.

Figure 15:
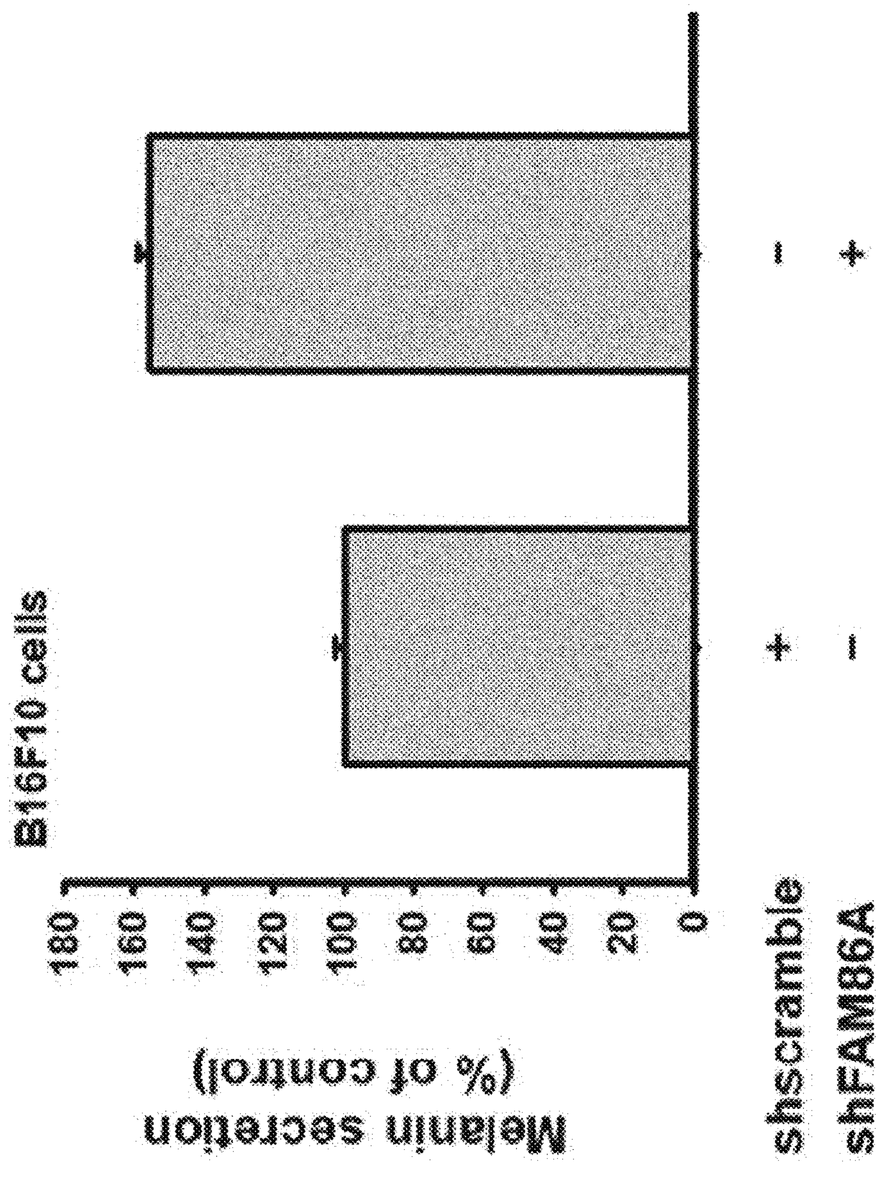
FIG. 15 shows a result of confirming a melanin secretion amount through a melanin secretion assay after mouse melanoma cells are subjected to knockdown of FAM86A using shRNA.

As shown in FIG. 15, it was confirmed that the amount of melanin secretion was increased in the FAM86A-knockdown group. Therefore, it was seen that melanin secretion is increased by FAM86A suppression.

Example 4-5. Western Blotting for Confirming Expression of Proteins of Melanogenesis Signaling Pathway The B16F10 cells cultured in Example 1 were seeded in 6-well plates at a density of $5\times10^4$ cells per well, grown for 24 hours, and FAM86A shRNA represented by SEQ ID NO: 17 was used to induce the knockdown of FAM86A gene. The cells were cultured in an incubator under conditions of 37° C. and 5% $CO_2$ for 48 hours. Afterward, the cells were washed twice with PBS. After completely removing the PBS, 200 μL of RIPA buffer, which is a cell lysis and staining reagent, was added to the plate, and the cells were collected using a scraper. Afterward, a protein was quantified using a BCA assay, and electrophoresis was performed using 10% SDS-PAGE. The protein in the resulting PAGE gel was transferred onto a PVDF membrane, and the resulting PVDF membrane onto which the protein transfer had been completed was blocked in TBS-T (in 100 mM NaCl, 10 mM Tris, 0.1% (v/v) Tween-20, pH 7.4 (PBST) containing 3% BSA) at room temperature. Then, after washing three times for 10 minutes using TBS-T, a primary antibody in 3% BSA dissolved in TBS-T was treated for 1 hour, and sufficiently washed with TBS-T. In addition, a secondary antibody was treated for 1 hour, and washed three times with PBS-T for 10 minutes each. Subsequently, the amount and location of a specific protein were confirmed using an ECL detection system. The correction of the protein amount was performed by checking the amount of an actin protein by stripping the PVDF membrane, and confirming it to have the same amount as that of the protein of interest. The primary and secondary antibodies were purchased from Cell Signaling and Santa Cruz.

Figure 16:
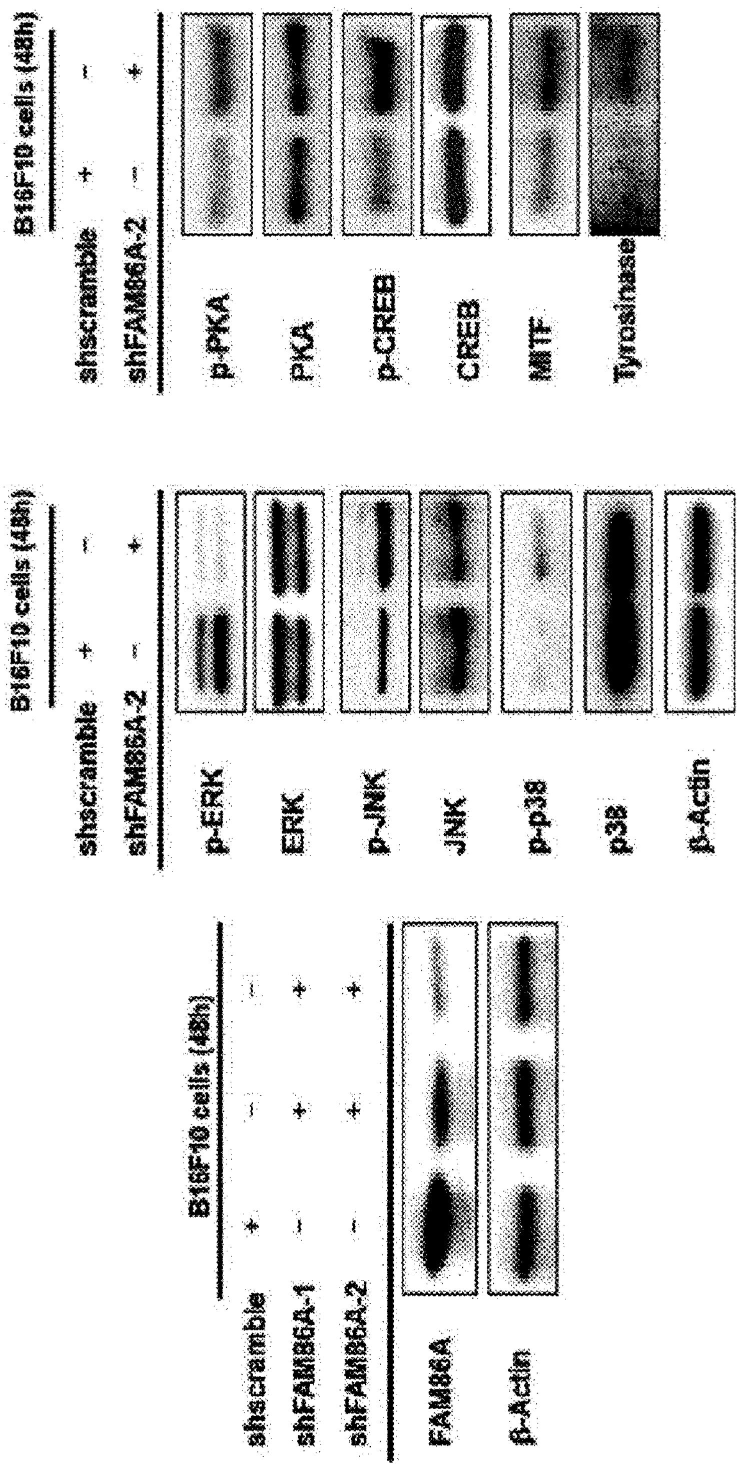
FIG. 16 shows a result of confirming FAM86A KID levels and expression levels of ERK, JNK, p38, PKA, CREB, MITF and tyrosinase, which are MAPK & MC1R signaling pathway proteins associated with melanogenesis, through western blotting analysis after mouse melanoma cells are subjected to knockdown of FAM86A using shRNA.

As shown in FIG. 16, the expression levels of melanogenesis-associated MAPK & MC1R signaling pathway proteins were confirmed. It was confirmed that, in a K/D group, FAM86A increased melanogenesis-associated p-JNK, p-p38, decreased p-ERK, and the expression levels of p-PKA, p-CREB and MITF proteins, which are proteins of the MC1R signaling pathway, were significantly increased. From these results, it was confirmed that the lower the FAM86A expression, the higher the activity of MC1R, which is a melanogenesis signaling pathway, showing that a decrease in FAM86A increases melanogenesis. Through this, it can be seen that melanin secretion is increased by FAM86A.

Example 4-6. Fontana-Masson Staining for Confirming the Presence of Melanin in Cells The B16F10 cells cultured in Example 1 were seeded in 6-well plates at a density of $5\times10^4$ cells per well, grown for 24 hours, and FAM86A shRNA represented by SEQ ID NO: 17 was used for knockdown of the FAM86A gene. The cells were treated with α-MSH at 100 nM. The resulting cells were cultured in an incubator under conditions of 37° C. and 5% $CO_2$ for 48 hours, washed twice with PBS, and 1 mL of a 1% ammoniacal silver nitrate solution was added to each well, followed by heating a plate in a 60° C. dryer for 1 hour. Subsequently, the plate was washed three times with running water, and treated with 1 mL of a 0.2% gold chloride solution per well for 30 seconds. Afterward, the plate was washed twice with running water, treated with 1 mL of a 5% sodium thiosulfate solution per well, washed twice with running water, treated with 1 mL of a 0.5% neutral red solution per well for 2 minutes, and then washed with running water. The reaction result was confirmed under a microscope.

Figure 17:
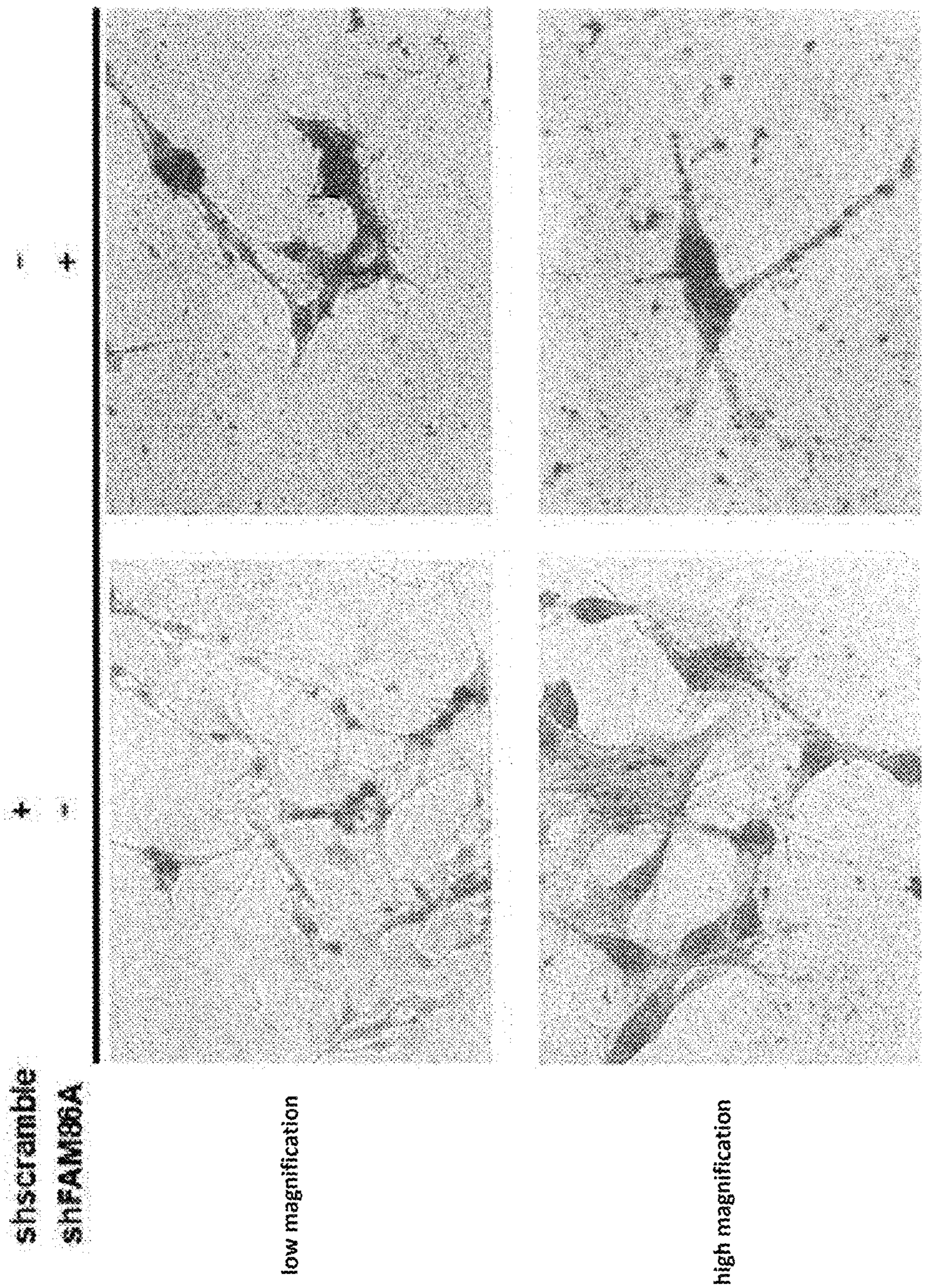
FIG. 17 shows a result of confirming the presence of melanin under a microscope by subjecting mouse melanoma cells to FAM86A knockdown using shRNA and then staining them by Fontana-Masson staining.

As shown in FIG. 17, it was confirmed that melanin was more present in the FAM86A knockdown group. Therefore, it was seen that intracellular and extracellular melanin was increased by FAM86A suppression.

Example 4-7. Confirmation of Expression Level of Melanogenesis-Associated Gene (Real-Time PCR)

The B16F10 cells cultured in Example 1 were seeded in 6-well plates at a density of $5\times10^4$ cells per well, grown for 24 hours, and FAM86A shRNA represented by SEQ ID NO: 17 was used for knockdown of the FAM86A gene. The cells were incubated in an incubator under conditions of 37° C. and 5% $CO_2$ for 48 hours. After 48 hours, the medium was completely removed, the cells were decomposed with TRIzol and neutralized using BCP. The neutralized liquid was treated with isopropanol to precipitate mRNA. Subsequently, only the precipitated mRNA was collected using a centrifuge, and used for the experiment. Intracellular mRNA was synthesized into cDNA using a cDNA kit, and the expression levels of tyrosinase, TYRP-1, TYRP-2 and MITF genes, which are important for melanogenesis, were determined by PCR.

Figure 18:
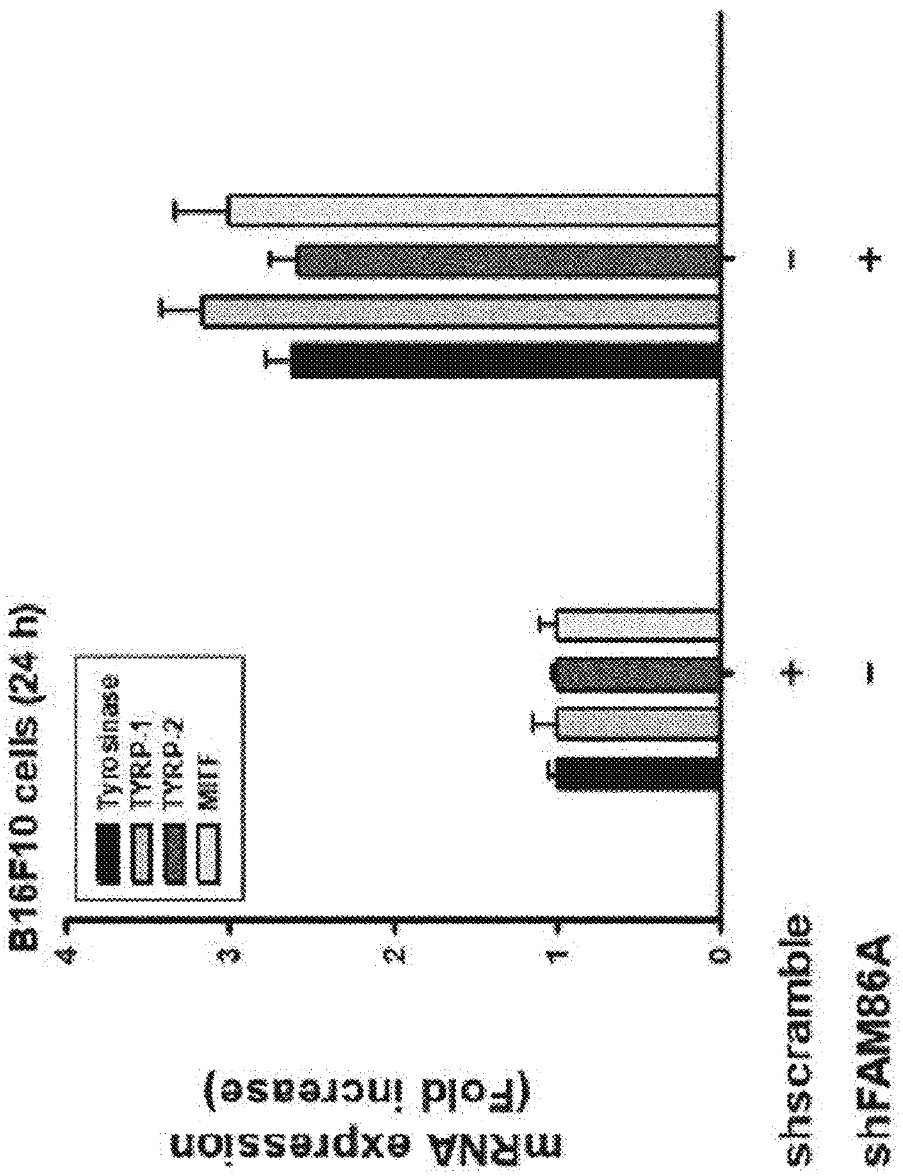
FIG. 18 shows a result of measuring expression levels of genes (tyrosinase, TYRP-1, TYRP-2 and MITF) playing a key role for melanogenesis using real-time PCR after mouse melanoma cells are subjected to FAM86A knockdown using shRNA.

As shown in FIG. 18, it was confirmed that the expression levels of the tyrosinase, TYRP-1, TYRP-2 and MITF genes, which are important for melanogenesis, were significantly increased in the FAM86A knockdown group. Accordingly, it was seen that melanogenesis was increased by FAM86A suppression.

Example 4-8. Confirmation of cAMP Expression Level (ELISA)

The B16F10 cells cultured in Example 1 were seeded in 6-well plates at a density of $5\times10^4$ cells per well, grown for 24 hours, and FAM86A shRNA represented by SEQ ID NO: 17 was used for FAM86A gene knockdown. Afterward, the cells were washed twice with PBS. Subsequently, PBS was completely removed, and then 200 μL of RIPA buffer, which is a tissue lysis and staining reagent, was added to each plate, followed by harvesting cells with a scraper. Afterward, a BCA assay was conducted to quantify proteins, and then the expression of cAMP protein was measured using a cAMP ELISA kit (ab65355).

Figure 19:
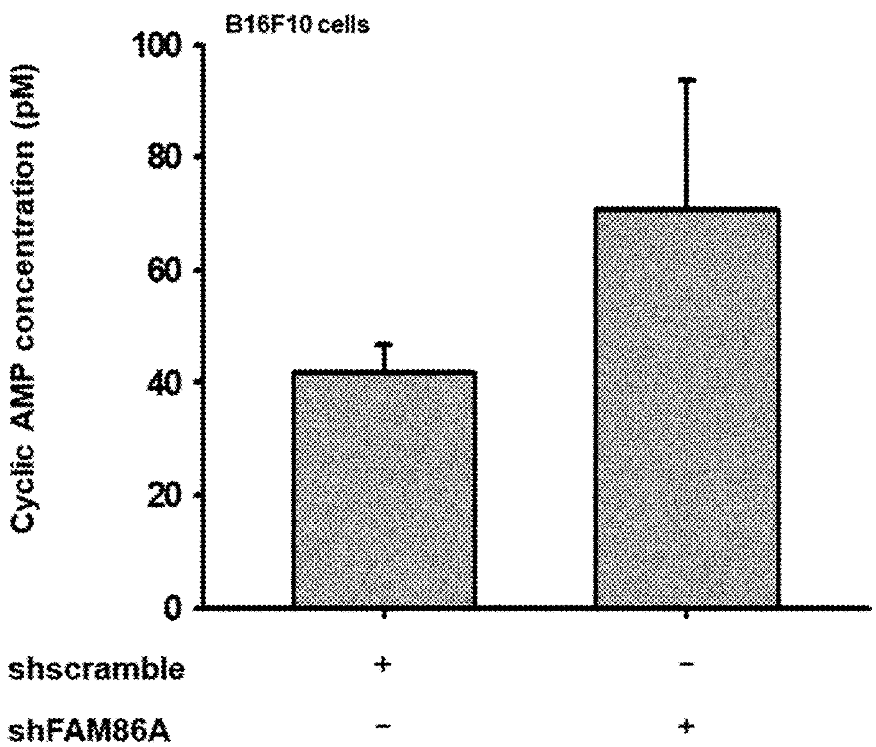
FIG. 19 shows a result of measuring the expression of cAMP, which is a protein important for melanogenesis through ELISA after mouse melanoma cells are subjected to FAM86A knockdown using shRNA.

As shown in FIG. 19, it was confirmed that cAMP expression was increased in the FAM86A knockdown group.

Example 4-9. Confirmation of Protein Binding to MC1R Protein (Immunoprecipitation)

The B16F10 cells cultured in Example 1 were seeded in a 6-well plate at $5\times10^4$ cells/well and cultured for 24 hours, and the knockdown of the FAM86A gene was induced using FAM86A shRNA represented by SEQ ID NO: 17. Afterward, the cells were washed twice with PBS. Subsequently, PBS was completely removed, and then 200 μL of RIPA buffer, which is a tissue lysis and staining reagent, was added to each plate, followed by harvesting cells with a scraper. Afterward, a BCA assay was conducted to quantify proteins, and then to perform immunoprecipitation analysis, the cell lysate solution was treated with an anti-MC1R antibody (3 μg) and reacted in PBS for 1 hour, and then protein A/G-agarose beads were added to allow a reaction at 4° C. for 24 hours. The beads were washed with PBS containing 1 mM DTT three times, and heated with a 2× protein loading dye (25% SDS, 62.5 mM Tris-HCl (pH 6.8), 25% glycerol, and 0.01% bromophenol blue) for 5 minutes at 95° C. The samples were subjected to electrophoresis using SDS-PAGE, thereby confirming proteins binding to the MC1R protein playing a pivotal role in melanogenesis in knockdown cells.

Figure 20:
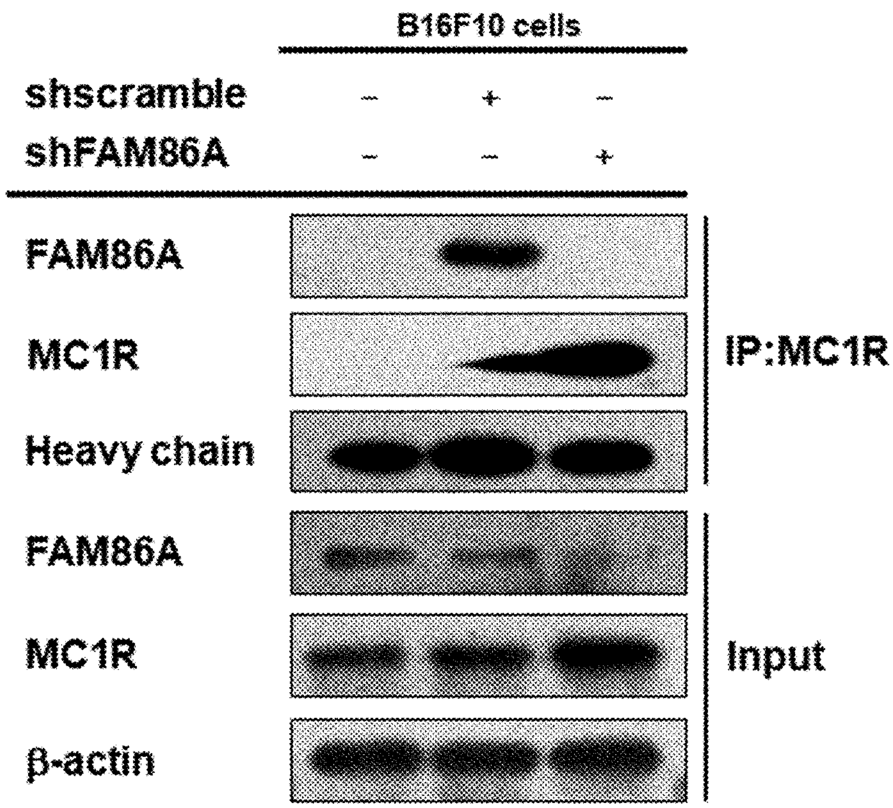
FIG. 20 shows a result of confirming proteins binding to protein MC1R playing a pivotal role in melanogenesis in knockdown cells after mouse melanoma cells are subjected to knockdown of FAM86A using shRNA and then to immunoprecipitation-MC1R.

As shown in FIG. 20, it was confirmed that MC1R binds to FAM86A and serves to form melanin.

By summarizing the above examples, the inventors confirmed that FAM86A can be used as a biomarker for detecting melanin production, and melanogenesis was detected by measuring an FAM86A level, and thus the pigment-associated condition of the skin can be diagnosed.

In addition, it can be seen that FAM86A can be used for a health functional food and a cosmetic composition for whitening, each of which includes the protein FAM86A of the present invention, and a marker for their development.

Further, it can be seen that the protein FAM86A of the present invention or an agonist thereof can be used as a cosmetic composition for use in skin whitening.

In addition, the inventors confirmed that the increase in melanin production and secretion by FAM86A suppression leads to an effect of preventing and treating a melanin-deficient disease. Therefore, it can be seen that an inhibitor for controlling FAM86A expression or activity can be used for a drug, health functional food and cosmetic composition for preventing, treating or alleviating a melanin-deficient disease, and a lead material for their development.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

Since FAM86A of the present invention is reduced with an increase in amount of melanin secretion or production, skin whitening is possible using the protein FAM86A or an agonist thereof, and as the melanin production and secretion are promoted during FAM86A suppression, melanin-deficient diseases such as vitiligo can be prevented, treated or alleviated. Therefore, the FAM86A of the present invention can be used in various fields, for example, a composition for skin whitening using the protein FAM86A or an agonist thereof and a composition for preventing and treating a melanin-deficient disease using the FAM86A inhibitor, indicating that the present invention has industrial applicability.

The invention claimed is:

1. A method of treating a melanin-deficient disease in a subject, comprising administering a pharmaceutically effective amount of composition comprising an FAM86A inhibitor as an active ingredient into the subject, wherein the FAM86A inhibitor is an FAM86A expression inhibitor, wherein the FAM86A expression inhibitor is an shRNA that complementarily binds to a mRNA of the FAM86A gene, and wherein the melanin-deficient disease is selected from the group consisting of: leukoderma; vitiligo; quadrichrome vitiligo; vitiligo ponctue; syndromic albinism; Alezzandrini syndrome; Hermansky-Pudlak syndrome; Chediak-Higashi syndrome; Griscelli syndrome type 1/Elejalde syndrome; Griscelli syndrome type 2; Griscelli syndrome type 3; Waardenburg syndrome; Tietz syndrome; CrossMuKusick-Breen syndrome; ABCD syndrome; Albinism-deafness syndrome; Vogt-Koyanagi-Harada syndrome; oculocutaneous albinism; canities; hypomelanosis; idiopathic guttate hypomelanosis; phylloid hypomelanosis; progressive macular hypomelanosis; piebaldism; nevus depigmentosus; postinflammatory hypopigmentation; pityriasis alba; Vagabond's leukomelanoderma; Yemenite deaf-blind hypopigmentation syndrome; Wende-Bauckus syndrome; Woronoff's ring; amelanism; and leucism.

2. A method of promoting melanogenesis, comprising administering a pharmaceutically effective amount of composition comprising an FAM86A inhibitor as an active ingredient into a subject, wherein the FAM86A inhibitor is an FAM86A expression inhibitor, wherein the FAM86A expression inhibitor is an shRNA that complementarily binds to the mRNA of the FAM86A gene, and wherein the administering increases melanogenesis in the subject.

3. A method of promoting black hair induction, comprising administering a pharmaceutically effective amount of composition comprising an FAM86A inhibitor as an active ingredient into a subject, wherein the FAM86A inhibitor is an FAM86A expression inhibitor, wherein the FAM86A expression inhibitor is an shRNA that complementarily binds to the mRNA of the FAM86A gene, and wherein the administering promotes the generation of black hair in the subject.

* * * * *

SEQUENCE LISTING

```
<160> NUMBER OF SEQ ID NOS: 48

<210> SEQ ID NO 1
<211> LENGTH: 330
<212> TYPE: PRT
<213> ORGANISM: Artificial Sequence
<220> FEATURE:
<223> OTHER INFORMATION: FAM86A(NP_958802.1)

<400> SEQUENCE: 1

Met Ala Pro Glu Glu Asn Ala Gly Thr Glu Leu Leu Leu Gln Ser Phe
1               5                   10                  15

Glu Arg Arg Phe Leu Ala Ala Arg Thr Leu Arg Ser Phe Pro Trp Gln
            20                  25                  30

Ser Leu Glu Ala Lys Leu Arg Asp Ser Ser Asp Ser Glu Leu Leu Arg
        35                  40                  45

Asp Ile Leu His Lys Thr Val Lys His Pro Val Cys Val Lys His Pro
    50                  55                  60

Pro Ser Val Lys Tyr Ala Arg Cys Phe Leu Ser Glu Leu Ile Lys Lys
65                  70                  75                  80

His Glu Ala Val His Thr Glu Pro Leu Asp Glu Leu Tyr Glu Ala Leu
                85                  90                  95
```

```
Ala Glu Thr Leu Met Ala Lys Glu Ser Thr Gln Gly His Arg Ser Tyr
            100                 105                 110

Leu Leu Pro Ser Gly Gly Ser Val Thr Leu Ser Glu Ser Thr Ala Ile
        115                 120                 125

Ile Ser Tyr Gly Thr Thr Gly Leu Val Thr Trp Asp Ala Ala Leu Tyr
    130                 135                 140

Leu Ala Glu Trp Ala Ile Glu Asn Pro Ala Val Phe Thr Asn Arg Thr
145                 150                 155                 160

Val Leu Glu Leu Gly Ser Gly Ala Gly Leu Thr Gly Leu Ala Ile Cys
                165                 170                 175

Lys Met Cys Arg Pro Arg Ala Tyr Ile Phe Ser Asp Cys His Ser Arg
            180                 185                 190

Val Leu Glu Gln Leu Arg Gly Asn Val Leu Leu Asn Gly Leu Ser Leu
        195                 200                 205

Glu Ala Asp Ile Thr Ala Lys Leu Asp Ser Pro Arg Val Thr Val Ala
    210                 215                 220

Gln Leu Asp Trp Asp Val Ala Thr Val His Gln Leu Ser Ala Phe Gln
225                 230                 235                 240

Pro Asp Val Val Ile Ala Ala Asp Val Leu Tyr Cys Pro Glu Ala Ile
                245                 250                 255

Met Ser Leu Val Gly Val Leu Arg Arg Leu Ala Ala Cys Arg Glu His
            260                 265                 270

Gln Arg Ala Pro Glu Val Tyr Val Ala Phe Thr Val Arg Asn Pro Glu
        275                 280                 285

Thr Cys Gln Leu Phe Thr Thr Glu Leu Gly Arg Ala Gly Ile Arg Trp
    290                 295                 300

Glu Val Glu Pro Arg His Glu Gln Lys Leu Phe Pro Tyr Glu Glu His
305                 310                 315                 320

Leu Glu Met Ala Met Leu Asn Leu Thr Leu
                325                 330
```

<210> SEQ ID NO 2
<211> LENGTH: 296
<212> TYPE: PRT
<213> ORGANISM: Artificial Sequence
<220> FEATURE:
<223> OTHER INFORMATION: FAM86B1(NP_001077006.1)

<400> SEQUENCE: 2

```
Met Ala Pro Glu Glu Asn Ala Gly Thr Glu Leu Leu Leu Gln Gly Phe
1               5                   10                  15

Glu Arg Arg Phe Leu Ala Val Arg Thr Leu Arg Ser Phe Pro Trp Gln
            20                  25                  30

Ser Leu Glu Ala Lys Leu Arg Asp Ser Ser Asp Ser Glu Leu Leu Arg
        35                  40                  45

Asp Ile Leu Gln Lys Thr Val Arg His Pro Val Cys Val Lys His Pro
    50                  55                  60

Pro Ser Val Lys Tyr Ala Trp Cys Phe Leu Ser Glu Leu Ile Lys Lys
65                  70                  75                  80

Ser Ser Gly Gly Ser Val Thr Leu Ser Lys Ser Thr Ala Ile Ile Ser
                85                  90                  95

His Gly Thr Thr Gly Leu Val Thr Trp Asp Ala Ala Leu Tyr Leu Ala
            100                 105                 110

Glu Trp Ala Ile Glu Asn Pro Ala Ala Phe Ile Asn Arg Thr Val Leu
        115                 120                 125
```

-continued

```
Glu Leu Gly Ser Gly Ala Gly Leu Thr Gly Leu Ala Ile Cys Lys Met
    130                 135                 140

Cys Arg Pro Arg Ala Tyr Ile Phe Ser Asp Pro His Ser Arg Val Leu
145                 150                 155                 160

Glu Gln Leu Arg Gly Asn Val Leu Leu Asn Gly Leu Ser Leu Glu Ala
                165                 170                 175

Asp Ile Thr Gly Asn Leu Asp Ser Pro Arg Val Thr Val Ala Gln Leu
            180                 185                 190

Asp Trp Asp Val Ala Met Val His Gln Leu Ser Ala Phe Gln Pro Asp
        195                 200                 205

Val Val Ile Ala Ala Asp Val Leu Tyr Cys Pro Glu Ala Ile Val Ser
    210                 215                 220

Leu Val Gly Val Leu Gln Arg Leu Ala Ala Cys Arg Glu His Lys Arg
225                 230                 235                 240

Ala Pro Glu Val Tyr Val Ala Phe Thr Val Arg Asn Pro Glu Thr Cys
                245                 250                 255

Gln Leu Phe Thr Thr Glu Leu Gly Arg Asp Gly Ile Arg Trp Glu Ala
            260                 265                 270

Glu Ala His His Asp Gln Lys Leu Phe Pro Tyr Gly Glu His Leu Glu
        275                 280                 285

Met Ala Met Leu Asn Leu Thr Leu
    290                 295


<210> SEQ ID NO 3
<211> LENGTH: 330
<212> TYPE: PRT
<213> ORGANISM: Artificial Sequence
<220> FEATURE:
<223> OTHER INFORMATION: FAM86B2(NP_NP_001131082.1)

<400> SEQUENCE: 3

Met Ala Pro Glu Glu Asn Ala Gly Thr Glu Leu Leu Leu Gln Gly Phe
1               5                   10                  15

Glu Arg Arg Phe Leu Ala Val Arg Thr Leu Arg Ser Phe Pro Trp Gln
            20                  25                  30

Ser Leu Glu Ala Lys Leu Arg Asp Ser Ser Asp Ser Glu Leu Leu Arg
        35                  40                  45

Asp Ile Leu Gln Lys Thr Val Arg His Pro Val Cys Val Lys His Pro
    50                  55                  60

Pro Ser Val Lys Tyr Ala Trp Cys Phe Leu Ser Glu Leu Ile Lys Lys
65                  70                  75                  80

His Glu Ala Val His Thr Glu Pro Leu Asp Lys Leu Tyr Glu Val Leu
                85                  90                  95

Ala Glu Thr Leu Met Ala Lys Glu Ser Thr Gln Gly His Arg Ser Tyr
            100                 105                 110

Leu Leu Ser Ser Gly Gly Ser Val Thr Leu Ser Lys Ser Thr Ala Ile
        115                 120                 125

Ile Ser His Gly Thr Thr Gly Leu Val Thr Trp Asp Ala Ala Leu Tyr
    130                 135                 140

Leu Ala Glu Trp Ala Ile Glu Asn Pro Ala Ala Phe Ile Asn Arg Thr
145                 150                 155                 160

Val Leu Glu Leu Gly Ser Gly Ala Gly Leu Thr Gly Leu Ala Ile Cys
                165                 170                 175

Lys Met Cys Arg Pro Arg Ala Tyr Ile Phe Ser Asp Pro His Ser Arg
            180                 185                 190
```

```
Ile Leu Glu Gln Leu Arg Gly Asn Val Leu Leu Asn Gly Leu Ser Leu
        195                 200                 205

Glu Ala Asp Ile Thr Gly Asn Leu Asp Ser Pro Arg Val Thr Val Ala
    210                 215                 220

Gln Leu Asp Trp Asp Val Ala Met Val His Gln Leu Ser Ala Phe Gln
225                 230                 235                 240

Pro Asp Val Val Ile Ala Ala Asp Val Leu Tyr Cys Pro Glu Ala Ile
                245                 250                 255

Val Ser Leu Val Gly Val Leu Gln Arg Leu Ala Ala Cys Arg Glu His
            260                 265                 270

Lys Arg Ala Pro Glu Val Tyr Val Ala Phe Thr Val Arg Asn Pro Glu
        275                 280                 285

Thr Cys Gln Leu Phe Thr Thr Glu Leu Gly Arg Asp Gly Ile Arg Trp
    290                 295                 300

Glu Ala Glu Ala His His Asp Gln Lys Leu Phe Pro Tyr Gly Glu His
305                 310                 315                 320

Leu Glu Met Ala Met Leu Asn Leu Thr Leu
                325                 330


<210> SEQ ID NO 4
<211> LENGTH: 165
<212> TYPE: PRT
<213> ORGANISM: Artificial Sequence
<220> FEATURE:
<223> OTHER INFORMATION: FAM86C1(NP_NP_060642.2)

<400> SEQUENCE: 4

Met Ala Pro Glu Glu Asn Ala Gly Ser Glu Leu Leu Leu Gln Ser Phe
1               5                   10                  15

Lys Arg Arg Phe Leu Ala Ala Arg Ala Leu Arg Ser Phe Arg Trp Gln
            20                  25                  30

Ser Leu Glu Ala Lys Leu Arg Asp Ser Ser Asp Ser Glu Leu Leu Arg
        35                  40                  45

Asp Ile Leu Gln Lys His Glu Ala Val His Thr Glu Pro Leu Asp Glu
    50                  55                  60

Leu Tyr Glu Val Leu Val Glu Thr Leu Met Ala Lys Glu Ser Thr Gln
65                  70                  75                  80

Gly His Arg Ser Tyr Leu Leu Thr Cys Cys Ile Ala Gln Lys Pro Ser
                85                  90                  95

Cys Arg Trp Ser Gly Ser Cys Gly Gly Trp Leu Pro Ala Gly Ser Thr
            100                 105                 110

Ser Gly Leu Leu Asn Ser Thr Trp Pro Leu Pro Ser Ala Thr Gln Arg
        115                 120                 125

Cys Ala Ser Cys Ser Pro Pro Ser Tyr Ala Gly Leu Gly Ser Asp Gly
    130                 135                 140

Lys Arg Lys Leu Ile Met Thr Arg Asn Cys Phe Pro Thr Glu Ser Thr
145                 150                 155                 160

Trp Arg Trp Gln Ser
                165


<210> SEQ ID NO 5
<211> LENGTH: 335
<212> TYPE: PRT
<213> ORGANISM: Artificial Sequence
<220> FEATURE:
<223> OTHER INFORMATION: FAM86(NP_081722.1)

<400> SEQUENCE: 5
```

```
Met Ala Pro Glu Asp His Glu Gly Ala Thr Ser Leu Leu Gln Ser Phe
1               5                   10                  15

Glu Arg Arg Phe Leu Ala Ala Arg Ala Leu Pro Ser Phe Pro Trp Gln
            20                  25                  30

Ser Leu Glu Glu Lys Leu Lys Asp Pro Ser Gly Ser Glu Leu Leu Leu
        35                  40                  45

Ala Ile Leu Gln Arg Thr Val Lys His Pro Val Cys Val Gln His Gly
    50                  55                  60

Pro Ser Val Lys Tyr Ala Arg Cys Phe Leu Ser Lys Leu Ile Lys Lys
65                  70                  75                  80

His Glu Ala Val Pro Thr Glu Pro Leu Asp Ala Leu Tyr Glu Ala Leu
                85                  90                  95

Ala Glu Val Leu Met Thr Gln Glu Ser Thr Gln Cys His Arg Ser Tyr
            100                 105                 110

Leu Leu Pro Ser Gly Asn Ser Val Thr Leu Ser Glu Ser Thr Ala Ile
        115                 120                 125

Val Ser His Gly Thr Thr Gly Leu Val Thr Trp Asp Ala Ala Leu Tyr
    130                 135                 140

Leu Ala Glu Trp Ala Ile Glu Asn Pro Ala Ala Phe Thr Asp Arg Thr
145                 150                 155                 160

Ile Leu Glu Leu Gly Ser Gly Ala Gly Leu Thr Gly Leu Ala Ile Cys
                165                 170                 175

Lys Ala Cys Cys Pro Arg Ala Tyr Ile Phe Ser Asp Cys His Ala Gln
            180                 185                 190

Val Leu Glu Gln Leu Arg Gly Asn Val Leu Leu Asn Gly Phe Ser Leu
        195                 200                 205

Glu Pro His Thr Pro Ile Asp Ala Gly Ser Ser Lys Val Thr Val Ala
    210                 215                 220

Gln Leu Asp Trp Asp Glu Val Thr Ala Ser Gln Leu Ser Ala Phe Gln
225                 230                 235                 240

Ala Asp Val Val Ile Ala Ala Asp Val Leu Tyr Cys Trp Glu Met Thr
                245                 250                 255

Leu Ser Leu Val Arg Val Leu Lys Met Leu Glu Asp Cys Gln Arg Lys
            260                 265                 270

Ser Ala Pro Asp Val Tyr Val Ala Tyr Thr Ile Arg Ser Gln Asp Thr
        275                 280                 285

Gly Lys Leu Phe Ile Glu Glu Leu Asp Arg Ala Gly Ile Tyr Trp Glu
    290                 295                 300

Glu Val Pro Pro His Thr Gly Lys Leu Phe Pro Tyr Glu Glu His Ser
305                 310                 315                 320

Ala Ile Val Ile Leu Lys Leu Val Leu Thr Ser Arg His Gly Val
                325                 330                 335
```

<210> SEQ ID NO 6
<211> LENGTH: 993
<212> TYPE: DNA
<213> ORGANISM: Artificial Sequence
<220> FEATURE:
<223> OTHER INFORMATION: FAM86A mRNA(NM_201400.4)

<400> SEQUENCE: 6

```
atggcgcccg aggagaacgc ggggaccgaa ctcttgctgc agagtttcga gcgccgcttc     60

ctggcggcac gcacactgcg ctccttcccc tggcagagct tagaagcaaa gttaagagac    120

tcatcagatt ctgagctgct gcgggatatt ttgcacaaga ctgtgaagca tcctgtgtgt    180
```

-continued

```
gtgaagcacc cgccgtccgt caaatatgcc cggtgctttc tctcagaact catcaaaaag    240

cacgaggctg tccacacaga gcctttggac gagctgtatg aagcgctggc ggagaccctg    300

atggccaagg agtccaccca gggccaccgg agctatttgc tgccctcggg aggctcggtc    360

acactctccg agagcacggc catcatctcc tacggtacca caggcctggt cacatgggac    420

gccgccctct accttgcaga atgggccatc gagaacccgg cagtcttcac taacaggact    480

gtcctagagc ttggcagtgg tgctggcctc acaggcctgg ccatctgcaa gatgtgccgc    540

ccccgggcat acatcttcag cgactgtcac agccgggtcc ttgagcagct ccgagggaat    600

gtccttctca atggcctctc attagaggca gacatcactg ccaagttaga cagccccagg    660

gtgacagtgg cccagctgga ctgggacgtc gcgacggtcc atcagctctc tgccttccag    720

ccagatgttg tcattgcagc agatgtgctg tattgcccag aagccatcat gtcgctggtc    780

ggcgtcctgc ggaggctggc tgcctgccgg gagcaccagc gggctcctga ggtctacgtg    840

gcctttaccg tccgcaaccc agagacgtgc cagctgttca ccaccgagct aggccgggcc    900

gggatcagat gggaagtgga acctcgtcat gagcagaaac tgtttcccta cgaagagcac    960

ttggagatgg caatgctgaa tctcaccctg tag                                 993
```

<210> SEQ ID NO 7
<211> LENGTH: 891
<212> TYPE: DNA
<213> ORGANISM: Artificial Sequence
<220> FEATURE:
<223> OTHER INFORMATION: FAM86B1 mRNA(NM_001083537.2)

<400> SEQUENCE: 7

```
atggcgcccg aggagaacgc ggggaccgaa ctcttgctgc agggttttga gcgccgcttc     60

ctggcggtgc gcacactgcg ctccttcccc tggcagagct tagaggcaaa gttaagagac    120

tcatcagatt ctgagctgct gcgggatatt ttgcagaaga ctgtgaggca tcctgtgtgt    180

gtgaagcacc cgccgtcagt caagtatgcc tggtgctttc tctcagaact catcaaaaag    240

tcctcaggag gctcagtcac actctccaag agcacagcca tcatctccca cggtaccaca    300

ggcctggtca catgggatgc cgccctctac cttgcagaat gggccatcga gaacccggca    360

gccttcatta acaggactgt cctagagctt ggcagtggtg ccggcctcac aggccttgcc    420

atctgcaaga tgtgccgccc ccgggcatac atcttcagcg accctcacag ccgggtcctc    480

gagcagctcc gagggaatgt ccttctcaat ggcctctcat tagaggcaga catcactggc    540

aacttagaca gccccagggt gacagtggcc cagctggact gggacgtagc aatggtccat    600

cagctctctg ccttccagcc agatgttgtc attgcagcag acgtgctgta ttgcccagaa    660

gccatcgtgt cgctggtcgg ggtcctgcag aggctggctg cctgccggga gcacaagcgg    720

gctcctgagg tctacgtggc ctttaccgtc cgcaacccag agacgtgcca gctgttcacc    780

accgagctag gccgggatgg gatcagatgg gaagcggaag ctcatcatga ccagaaactg    840

tttccctatg gagagcactt ggagatggca atgctgaacc tcacactgta g             891
```

<210> SEQ ID NO 8
<211> LENGTH: 993
<212> TYPE: DNA
<213> ORGANISM: Artificial Sequence
<220> FEATURE:
<223> OTHER INFORMATION: FAM86B2 mRNA(NM_001137610.2)

<400> SEQUENCE: 8

-continued

```
atggcgcccg aggagaacgc ggggaccgaa ctcttgctgc agggttttga gcgccgcttc      60
ctggcggtgc gcacactgcg ctccttcccc tggcagagct tagaggcaaa gttaagagac     120
tcatcagatt ctgagctgct gcgggatatt ttgcagaaga ctgtgaggca tcctgtgtgt     180
gtgaagcacc cgccgtcagt caagtatgcc tggtgctttc tctcagaact catcaaaaag     240
cacgaggctg tccacacgga gcctttggac aaactgtacg aggtgctcgc ggagactctg     300
atggccaagg agtccaccca gggccaccgg agctatttgc tgtcctcagg aggctcagtc     360
acactctcca agagcacagc catcatctcc cacggtacca caggcctggt cacatgggat     420
gccgccctct accttgcaga atgggccatc gagaacccgg cagccttcat taacaggact     480
gtcctagagc ttggcagtgg tgccggcctc acaggccttg ccatctgcaa gatgtgccgc     540
ccccgggcat acatcttcag cgaccctcac agccggatcc tcgagcagct ccgagggaat     600
gtccttctca atggcctctc attagaggca gacatcactg gcaacttaga cagccccagg     660
gtgacagtgg cccagctgga ctgggacgta gcaatggtcc atcagctctc tgccttccag     720
ccagatgttg tcattgcagc agacgtgctg tattgcccag aagccatcgt gtcgctggtc     780
ggggtcctgc agaggctggc tgcctgccgg gagcacaagc gggctcctga ggtctacgtg     840
gcctttaccg tccgcaaccc agagacatgc cagctgttca ccaccgagct aggccgggat     900
gggatcagat gggaagcgga agctcatcat gaccagaaac tgtttcccta tggagagcac     960
ttggagatgg caatgctgaa cctcacactg tag                                  993
```

<210> SEQ ID NO 9
<211> LENGTH: 498
<212> TYPE: DNA
<213> ORGANISM: Artificial Sequence
<220> FEATURE:
<223> OTHER INFORMATION: FAM86C1 mRNA(NM_018172.3)

<400> SEQUENCE: 9

```
atggcgcccg aggagaacgc ggggagcgaa ctcttgctgc agagtttcaa gcgccgcttc      60
ctggcagcgc gcgccctgcg ctccttccgc tggcagagct tagaagcaaa gttaagagac     120
tcatcagatt ctgagctgct gcgggatatt ttgcagaagc acgaggctgt ccacacagag     180
cctttggatg agctgtacga ggtgctggtg gagaccctga tggccaagga gtccacccag     240
ggccaccgga gctatttgct gacgtgctgt attgcccaga agccatcgtg tcgctggtcg     300
gggtcctgcg gaggctggct gcctgccggg agcaccagcg ggctcctcaa ttctacatgg     360
cccttaccgt ctgcaaccca gagatgtgcc agctgttcac caccgagcta tgctggactg     420
ggatcagatg ggaagcggaa gctcatcatg accagaaact gtttccctac agagagcact     480
tggagatggc aaagctga                                                   498
```

<210> SEQ ID NO 10
<211> LENGTH: 1008
<212> TYPE: DNA
<213> ORGANISM: Artificial Sequence
<220> FEATURE:
<223> OTHER INFORMATION: FAM86 mRNA(NM_027446.2)

<400> SEQUENCE: 10

```
atggcgcctg aggaccacga gggggccacg tctctgctgc agagtttcga gcgccgcttc      60
ctggcggctc gcgcgctgcc ctcctttccc tggcagagcc tagaagaaaa actaaaggac     120
ccctcgggtt ctgagctgtt gctggctatt ctgcagagga ctgtgaagca ccctgtgtgt     180
gtgcagcacg gaccttctgt gaagtatgcc cgctgctttc tctcaaagct catcaaaaag     240
```

```
catgaggctg tacccacgga gcctttggat gcactgtatg aggcgttggc agaggttctg    300

atgacccaag agtccaccca gtgccaccgg agctatttgc tgccttcagg aaactcagtt    360

acactctctg agagcactgc catcgtgtcc catggcacca caggcttggt tacatgggac    420

gctgctctct acctggcaga atgggccatt gagaacccag cagccttcac tgacaggact    480

atcctggagc taggcagtgg agctggcctt acaggcctgg caatttgcaa ggcatgctgc    540

cccagagcat acatcttcag cgactgtcat gcccaagtgc ttgagcagct ccgtggaaac    600

gttctcctca acggcttctc cttagagccg cacaccccca ttgacgcagg cagctcgaag    660

gtgacagtgg ctcagctgga ctgggacgag gtgacagcct ctcagctctc tgccttccag    720

gcagatgttg tcattgcagc agatgtactg tactgctggg agatgacact gtcactggtc    780

agggtcctga agatgctcga ggactgccag aggaagagcg ctcctgatgt ctatgtagcc    840

tatactatcc gcagccagga cacaggcaag ctgttcatcg aagagctgga ccgtgctgga    900

atctactggg aagaggtgcc ccctcacact ggcaaactgt tcccttacga agagcattca    960

gccatcgtaa tcctgaagct ggtgctgacc agtcgccatg gtgtttga                1008
```

<210> SEQ ID NO 11
<211> LENGTH: 58
<212> TYPE: RNA
<213> ORGANISM: Artificial Sequence
<220> FEATURE:
<223> OTHER INFORMATION: Homo sapiens FAM86A shRNA

<400> SEQUENCE: 11

```
ccgggcagaa actgtttccc tacgactcga gtcgtaggga aacagtttct gctttttg       58
```

<210> SEQ ID NO 12
<211> LENGTH: 58
<212> TYPE: RNA
<213> ORGANISM: Artificial Sequence
<220> FEATURE:
<223> OTHER INFORMATION: Homo sapiens FAM86A shRNA

<400> SEQUENCE: 12

```
ccggcgaggg aatgtccttc tcaatctcga gattgagaag gacattccct cgtttttg       58
```

<210> SEQ ID NO 13
<211> LENGTH: 58
<212> TYPE: RNA
<213> ORGANISM: Artificial Sequence
<220> FEATURE:
<223> OTHER INFORMATION: Homo sapiens FAM86A shRNA

<400> SEQUENCE: 13

```
ccgggatgtt gtcattgcag cagatctcga gatctgctgc aatgacaaca tctttttg       58
```

<210> SEQ ID NO 14
<211> LENGTH: 58
<212> TYPE: RNA
<213> ORGANISM: Artificial Sequence
<220> FEATURE:
<223> OTHER INFORMATION: Homo sapiens FAM86A shRNA

<400> SEQUENCE: 14

```
ccgggccagc agttctggtt cttaactcga gttaagaacc agaactgctg gctttttg       58
```

<210> SEQ ID NO 15
<211> LENGTH: 58
<212> TYPE: RNA

```
<213> ORGANISM: Artificial Sequence
<220> FEATURE:
<223> OTHER INFORMATION: Homo sapiens FAM86A shRNA

<400> SEQUENCE: 15

ccgggcagac atcactgcca agttactcga gtaacttggc agtgatgtct gctttttg      58


<210> SEQ ID NO 16
<211> LENGTH: 58
<212> TYPE: RNA
<213> ORGANISM: Artificial Sequence
<220> FEATURE:
<223> OTHER INFORMATION: Mus musculus FAM86 shRNA

<400> SEQUENCE: 16

ccgggagcat tcagccatcg taatcctcga ggattacgat ggctgaatgc tctttttg      58


<210> SEQ ID NO 17
<211> LENGTH: 58
<212> TYPE: RNA
<213> ORGANISM: Artificial Sequence
<220> FEATURE:
<223> OTHER INFORMATION: Mus musculus FAM86 shRNA

<400> SEQUENCE: 17

ccgggtctat gtagcctata ctatcctcga ggatagtata ggctacatag actttttg      58


<210> SEQ ID NO 18
<211> LENGTH: 58
<212> TYPE: RNA
<213> ORGANISM: Artificial Sequence
<220> FEATURE:
<223> OTHER INFORMATION: Mus musculus FAM86 shRNA

<400> SEQUENCE: 18

ccgggcctta caggcctggc aatttctcga gaaattgcca ggcctgtaag gctttttg      58


<210> SEQ ID NO 19
<211> LENGTH: 57
<212> TYPE: RNA
<213> ORGANISM: Artificial Sequence
<220> FEATURE:
<223> OTHER INFORMATION: Mus musculus FAM86 shRNA

<400> SEQUENCE: 19

ccggacggac cttctgtgaa gtatgctcga gcatacttca cagaaggtcc gtttttg       57


<210> SEQ ID NO 20
<211> LENGTH: 58
<212> TYPE: RNA
<213> ORGANISM: Artificial Sequence
<220> FEATURE:
<223> OTHER INFORMATION: Mus musculus FAM86 shRNA

<400> SEQUENCE: 20

ccgggttgtc attgcagcag atgtactcga gtacatctgc tgcaatgaca actttttg      58


<210> SEQ ID NO 21
<211> LENGTH: 21
<212> TYPE: DNA
<213> ORGANISM: Artificial Sequence
<220> FEATURE:
<223> OTHER INFORMATION: Homo sapiens FAM86A shRNA Target sequence

<400> SEQUENCE: 21

gcagaaactg tttccctacg a                                              21
```

-continued

<210> SEQ ID NO 22
<211> LENGTH: 21
<212> TYPE: DNA
<213> ORGANISM: Artificial Sequence
<220> FEATURE:
<223> OTHER INFORMATION: Homo sapiens FAM86A shRNA Target sequence

<400> SEQUENCE: 22
cgagggaatg tccttctcaa t 21

<210> SEQ ID NO 23
<211> LENGTH: 21
<212> TYPE: DNA
<213> ORGANISM: Artificial Sequence
<220> FEATURE:
<223> OTHER INFORMATION: Homo sapiens FAM86A shRNA Target sequence

<400> SEQUENCE: 23
gatgttgtca ttgcagcaga t 21

<210> SEQ ID NO 24
<211> LENGTH: 21
<212> TYPE: DNA
<213> ORGANISM: Artificial Sequence
<220> FEATURE:
<223> OTHER INFORMATION: Homo sapiens FAM86A shRNA Target sequence

<400> SEQUENCE: 24
gccagcagtt ctggttctta a 21

<210> SEQ ID NO 25
<211> LENGTH: 21
<212> TYPE: DNA
<213> ORGANISM: Artificial Sequence
<220> FEATURE:
<223> OTHER INFORMATION: Homo sapiens FAM86A shRNA Target sequence

<400> SEQUENCE: 25
gcagacatca ctgccaagtt a 21

<210> SEQ ID NO 26
<211> LENGTH: 21
<212> TYPE: DNA
<213> ORGANISM: Artificial Sequence
<220> FEATURE:
<223> OTHER INFORMATION: Mus musculus FAM86 shRNA Target sequence

<400> SEQUENCE: 26
gagcattcag ccatcgtaat c 21

<210> SEQ ID NO 27
<211> LENGTH: 21
<212> TYPE: DNA
<213> ORGANISM: Artificial Sequence
<220> FEATURE:
<223> OTHER INFORMATION: Mus musculus FAM86 shRNA Target sequence

<400> SEQUENCE: 27
gtctatgtag cctatactat c 21

<210> SEQ ID NO 28
<211> LENGTH: 21
<212> TYPE: DNA
<213> ORGANISM: Artificial Sequence
<220> FEATURE:

<223> OTHER INFORMATION: Mus musculus FAM86 shRNA Target sequence

<400> SEQUENCE: 28
gccttacagg cctggcaatt t 21

<210> SEQ ID NO 29
<211> LENGTH: 21
<212> TYPE: DNA
<213> ORGANISM: Artificial Sequence
<220> FEATURE:
<223> OTHER INFORMATION: Mus musculus FAM86 shRNA Target sequence

<400> SEQUENCE: 29
acggaccttc tgtgaagtat g 21

<210> SEQ ID NO 30
<211> LENGTH: 21
<212> TYPE: DNA
<213> ORGANISM: Artificial Sequence
<220> FEATURE:
<223> OTHER INFORMATION: Mus musculus FAM86 shRNA Target sequence

<400> SEQUENCE: 30
gttgtcattg cagcagatgt a 21

<210> SEQ ID NO 31
<211> LENGTH: 19
<212> TYPE: DNA
<213> ORGANISM: Artificial Sequence
<220> FEATURE:
<223> OTHER INFORMATION: Homo sapiens FAM86A siRNA Target sequence

<400> SEQUENCE: 31
aactcttgct gcagagttt 19

<210> SEQ ID NO 32
<211> LENGTH: 19
<212> TYPE: DNA
<213> ORGANISM: Artificial Sequence
<220> FEATURE:
<223> OTHER INFORMATION: Homo sapiens FAM86A siRNA Target sequence

<400> SEQUENCE: 32
cttagaagca aagttaaga 19

<210> SEQ ID NO 33
<211> LENGTH: 19
<212> TYPE: DNA
<213> ORGANISM: Artificial Sequence
<220> FEATURE:
<223> OTHER INFORMATION: Homo sapiens FAM86A siRNA Target sequence

<400> SEQUENCE: 33
ttaagagact catcagatt 19

<210> SEQ ID NO 34
<211> LENGTH: 19
<212> TYPE: DNA
<213> ORGANISM: Artificial Sequence
<220> FEATURE:
<223> OTHER INFORMATION: Homo sapiens FAM86A siRNA Target sequence

<400> SEQUENCE: 34
tctcaatggc ctctcatta 19

<210> SEQ ID NO 35
<211> LENGTH: 19
<212> TYPE: DNA
<213> ORGANISM: Artificial Sequence
<220> FEATURE:
<223> OTHER INFORMATION: Homo sapiens FAM86A siRNA Target sequence

<400> SEQUENCE: 35
gaatgtttgg agaatgtta 19

<210> SEQ ID NO 36
<211> LENGTH: 21
<212> TYPE: DNA
<213> ORGANISM: Artificial Sequence
<220> FEATURE:
<223> OTHER INFORMATION: Mus musculus FAM86 siRNA Target sequence

<400> SEQUENCE: 36
aagagcattc agccatcgta a 21

<210> SEQ ID NO 37
<211> LENGTH: 21
<212> TYPE: DNA
<213> ORGANISM: Artificial Sequence
<220> FEATURE:
<223> OTHER INFORMATION: Mus musculus FAM86A siRNA Target sequence

<400> SEQUENCE: 37
aagatgctcg aggactgcca g 21

<210> SEQ ID NO 38
<211> LENGTH: 21
<212> TYPE: DNA
<213> ORGANISM: Artificial Sequence
<220> FEATURE:
<223> OTHER INFORMATION: Mus musculus FAM86A siRNA Target sequence

<400> SEQUENCE: 38
aactcagtta cactctctga g 21

<210> SEQ ID NO 39
<211> LENGTH: 21
<212> TYPE: DNA
<213> ORGANISM: Artificial Sequence
<220> FEATURE:
<223> OTHER INFORMATION: Mus musculus FAM86A siRNA Target sequence

<400> SEQUENCE: 39
aaactcagtt acactctctg a 21

<210> SEQ ID NO 40
<211> LENGTH: 116
<212> TYPE: RNA
<213> ORGANISM: Artificial Sequence
<220> FEATURE:
<223> OTHER INFORMATION: Homo sapiens FAM86A miR-145

<400> SEQUENCE: 40
caccttgtcc tcacggtcca gttttcccag gaatccctta gatgctaaga tggggattcc 60
tggaaatact gttcttgagg tcatggtttg gaaatactgt tcttgaggtc atggtt 116

<210> SEQ ID NO 41
<211> LENGTH: 110
<212> TYPE: RNA
<213> ORGANISM: Artificial Sequence
<220> FEATURE:

<223> OTHER INFORMATION: Homo sapiens FAM86A miR-204

<400> SEQUENCE: 41
ggctacagtc tttcttcatg tgactcgtgg acttcccttt gtcatcctat gcctgagaat 60
atatgaagga ggctgggaag gcaaagggac gttcaattgt catcactggc 110

<210> SEQ ID NO 42
<211> LENGTH: 110
<212> TYPE: RNA
<213> ORGANISM: Artificial Sequence
<220> FEATURE:
<223> OTHER INFORMATION: Homo sapiens FAM86A miR-211

<400> SEQUENCE: 42
tcacctggcc atgtgacttg tgggcttccc tttgtcatcc ttcgcctagg gctctgagca 60
gggcagggac agcaaagggg tgctcagttg tcacttccca cagcacggag 110

<210> SEQ ID NO 43
<211> LENGTH: 79
<212> TYPE: RNA
<213> ORGANISM: Artificial Sequence
<220> FEATURE:
<223> OTHER INFORMATION: Mus musculus FAM86 miR-370

<400> SEQUENCE: 43
agacggagag accaggtcac gtctctgcag ttacacagct catgagtgcc tgctggggtg 60
gaacctggtt tgtctgtct 79

<210> SEQ ID NO 44
<211> LENGTH: 83
<212> TYPE: RNA
<213> ORGANISM: Artificial Sequence
<220> FEATURE:
<223> OTHER INFORMATION: Mus musculus FAM86 miR-290

<400> SEQUENCE: 44
ctcatcttgc ggtactcaaa ctatgggggc actttttttt ttctttaaaa agtgccgcct 60
agttttaagc cccgccggtt gag 83

<210> SEQ ID NO 45
<211> LENGTH: 82
<212> TYPE: RNA
<213> ORGANISM: Artificial Sequence
<220> FEATURE:
<223> OTHER INFORMATION: Mus musculus FAM86 miR-292

<400> SEQUENCE: 45
cagcctgtga tactcaaact gggggctctt ttggattttc atcggaagaa aagtgccgcc 60
aggttttgag tgtcaccggt tg 82

<210> SEQ ID NO 46
<211> LENGTH: 4795
<212> TYPE: DNA
<213> ORGANISM: Artificial Sequence
<220> FEATURE:
<223> OTHER INFORMATION: pCMV Myc mFAM86 full vector

<400> SEQUENCE: 46
gagttcgagc ttgcatgcct gcaggtcgtt acataactta cggtaaatgg cccgcctggc 60
tgaccgccca acgacccccg cccattgacg tcaataatga cgtatgttcc catagtaacg 120
ccaataggga ctttccattg acgtcaatgg gtggagtatt tacggtaaac tgcccacttg 180

-continued

```
gcagtacatc aagtgtatca tatgccaagt acgcccccta ttgacgtcaa tgacggtaaa    240
tggcccgcct ggcattatgc ccagtacatg accttatggg actttcctac ttggcagtac    300
atctacgtat tagtcatcgc tattaccatg gtgatgcggt tttggcagta catcaatggg    360
cgtggatagc ggtttgactc acggggattt ccaagtctcc accccattga cgtcaatggg    420
agtttgtttt ggcaccaaaa tcaacgggac tttccaaaat gtcgtaacaa ctccgcccca    480
ttgacgcaaa tgggcggtag gcgtgtacgg tgggaggtct atataagcag agctcgttta    540
gtgaaccgtc agatcgcctg gagacgccat ccacgctgtt ttgacctcca tagaagacac    600
cgggaccgat ccagcctccg gactctagag gatccggtac tagaggaact gaaaaaccag    660
aaagttaact ggtaagttta gtctttttgt cttttatttc aggtcccgga tccggtggtg    720
gtgcaaatca aagaactgct cctcagtgga tgttgccttt acttctaggc ctgtacggaa    780
gtgttacttc tgctctaaaa gctgcggaat tgtacccgcg ggcccaccat ggcatcaatg    840
cagaagctga tctcagagga ggacctgctt atggccatgg aggcccgaat tcggtcgact    900
gcgcctgagg accacgaggg ggccacgtct ctgctgcaga gtttcgagcg ccgcttcctg    960
gcggctcgcg cgctgccctc ctttccctgg cagagcctag aagaaaaact aaaggacccc   1020
tcgggttctg agctgttgct ggctattctg cagaggactg tgaagcaccc tgtgtgtgtg   1080
cagcacggac cttctgtgaa gtatgcccgc tgctttctct caaagctcat caaaaagcat   1140
gaggctgtac ccacggagcc tttggatgca ctgtatgagg cgttggcaga ggttctgatg   1200
acccaagagt ccacccagtg ccaccggagc tatttgctgc cttcaggaaa ctcagttaca   1260
ctctctgaga gcactgccat cgtgtcccat ggcaccacag gcttggttac atggacgct    1320
gctctctacc tggcagaatg ggccattgag aacccagcag ccttcactga caggactatc   1380
ctggagctag gcagtggagc tggccttaca ggcctggcaa tttgcaaggc atgctgcccc   1440
agagcataca tcttcagcga ctgtcatgcc caagtgcttg agcagctccg tggaaacgtt   1500
ctcctcaacg gcttctcctt agagccgcac acccccattg acgcaggcag ctcgaaggtg   1560
acagtggctc agctggactg ggacgaggtg acagcctctc agctctctgc cttccaggca   1620
gatgttgtca ttgcagcaga tgtactgtac tgctgggaga tgacactgtc actggtcagg   1680
gtcctgaaga tgctcgagga ctgccagagg aagagcgctc ctgatgtcta tgtagcctat   1740
actatccgca gccaggacac aggcaagctg ttcatcgaag agctggaccg tgctggaatc   1800
tactgggaag aggtgccccc tcacactggc aaactgttcc cttacgaaga gcattcagcc   1860
atcgtaatcc tgaagctggt gctgaccagt cgccatggtg tttgaagatc tctcgaggta   1920
ccgcggccgc ggggatccag acatgataag atacattgat gagtttggac aaaccacaac   1980
tagaatgcag tgaaaaaaat gctttatttg tgaaatttgt gatgctattg ctttatttgt   2040
aaccattata agctgcaata aacaagttaa caacaacaat tgcattcatt ttatgtttca   2100
ggttcagggg gaggtgtggg aggtttttc ggatcctcta gagtcgatct gcaggcatgc    2160
tagcttggcg taatcatggt catagctgtt tcctgtgtga aattgttatc cgctcacaat   2220
tccacacaac atacgagccg gaagcataaa gtgtaaagcc tggggtgcct aatgagtgag   2280
ctaactcaca ttaattgcgt tgcgctcact gcccgctttc cagtcgggaa acctgtcgtg   2340
ccagctgcat taatgaatcg gccaacgcgc ggggagaggc ggtttgcgta ttgggcgctc   2400
ttccgcttcc tcgctcactg actcgctgcg ctcggtcgtt cggctgcggc gagcggtatc   2460
agctcactca aaggcggtaa tacggttatc cacagaatca ggggataacg caggaaagaa   2520
```

```
catgtgagca aaaggccagc aaaaggccag gaaccgtaaa aaggccgcgt tgctggcgtt   2580
tttccatagg ctccgccccc ctgacgagca tcacaaaaat cgacgctcaa gtcagaggtg   2640
gcgaaacccg acaggactat aaagatacca ggcgtttccc cctggaagct ccctcgtgcg   2700
ctctcctgtt ccgaccctgc cgcttaccgg atacctgtcc gcctttctcc cttcgggaag   2760
cgtggcgctt tctcatagct cacgctgtag gtatctcagt tcggtgtagg tcgttcgctc   2820
caagctgggc tgtgtgcacg aaccccccgt tcagcccgac cgctgcgcct tatccggtaa   2880
ctatcgtctt gagtccaacc cggtaagaca cgacttatcg ccactggcag cagccactgg   2940
taacaggatt agcagagcga ggtatgtagg cggtgctaca gagttcttga agtggtggcc   3000
taactacggc tacactagaa gaacagtatt tggtatctgc gctctgctga agccagttac   3060
cttcggaaaa agagttggta gctcttgatc cggcaaacaa accaccgctg gtagcggtgg   3120
tttttttgtt tgcaagcagc agattacgcg cagaaaaaaa ggatctcaag aagatccttt   3180
gatcttttct acggggtctg acgctcagtg gaacgaaaac tcacgttaag ggattttggt   3240
catgagatta tcaaaaagga tcttcaccta gatcctttta aattaaaaat gaagttttaa   3300
atcaatctaa agtatatatg agtaaacttg gtctgacagt taccaatgct taatcagtga   3360
ggcacctatc tcagcgatct gtctatttcg ttcatccata gttgcctgac tccccgtcgt   3420
gtagataact acgatacggg agggcttacc atctggcccc agtgctgcaa tgataccgcg   3480
agacccacgc tcaccggctc cagatttatc agcaataaac cagccagccg gaagggccga   3540
gcgcagaagt ggtcctgcaa ctttatccgc ctccatccag tctattaatt gttgccggga   3600
agctagagta agtagttcgc cagttaatag tttgcgcaac gttgttgcca ttgctacagg   3660
catcgtggtg tcacgctcgt cgtttggtat ggcttcattc agctccggtt cccaacgatc   3720
aaggcgagtt acatgatccc ccatgttgtg caaaaaagcg gttagctcct tcggtcctcc   3780
gatcgttgtc agaagtaagt tggccgcagt gttatcactc atggttatgg cagcactgca   3840
taattctctt actgtcatgc catccgtaag atgcttttct gtgactggtg agtactcaac   3900
caagtcattc tgagaatagt gtatgcggcg accgagttgc tcttgcccgg cgtcaatacg   3960
ggataatacc gcgccacata gcagaacttt aaaagtgctc atcattggaa aacgttcttc   4020
ggggcgaaaa ctctcaagga tcttaccgct gttgagatcc agttcgatgt aacccactcg   4080
tgcacccaac tgatcttcag catcttttac tttcaccagc gtttctgggt gagcaaaaac   4140
aggaaggcaa aatgccgcaa aaaagggaat aagggcgaca cggaaatgtt gaatactcat   4200
actcttcctt tttcaatatt attgaagcat ttatcagggt tattgtctca tgagcggata   4260
catatttgaa tgtatttaga aaaataaaca aataggggtt ccgcgcacat ttccccgaaa   4320
agtgccacct gacgtctaag aaaccattat tatcatgaca ttaacctata aaaataggcg   4380
tatcacgagg ccctttcgtc tcgcgcgttt cggtgatgac ggtgaaaacc tctgacacat   4440
gcagctcccg gagacggtca cagcttgtct gtaagcggat gccgggagca gacaagcccg   4500
tcagggcgcg tcagcgggtg ttggcgggtg tcggggctgg cttaactatg cggcatcaga   4560
gcagattgta ctgagagtgc accatatgcg gtgtgaaata ccgcacagat gcgtaaggag   4620
aaaataccgc atcaggcgcc attcgccatt caggctgcgc aactgttggg aagggcgatc   4680
ggtgcgggcc tcttcgctat tacgccagct ggcgaaaggg ggatgtgctg caaggcgatt   4740
aagttgggta acgccagggt ttcccagtc acgacgttgt aaaacgacgg ccagt         4795
```

<210> SEQ ID NO 47
<211> LENGTH: 1008

<212> TYPE: DNA
<213> ORGANISM: Artificial Sequence
<220> FEATURE:
<223> OTHER INFORMATION: mFAM86

<400> SEQUENCE: 47
atggcgcctg aggaccacga gggggccacg tctctgctgc agagtttcga gcgccgcttc 60
ctggcggctc gcgcgctgcc ctcctttccc tggcagagcc tagaagaaaa actaaaggac 120
ccctcgggtt ctgagctgtt gctggctatt ctgcagagga ctgtgaagca ccctgtgtgt 180
gtgcagcacg gaccttctgt gaagtatgcc cgctgctttc tctcaaagct catcaaaaag 240
catgaggctg tacccacgga gcctttggat gcactgtatg aggcgttggc agaggttctg 300
atgacccaag agtccaccca gtgccaccgg agctatttgc tgccttcagg aaactcagtt 360
acactctctg agagcactgc catcgtgtcc catggcacca caggcttggt tacatgggac 420
gctgctctct acctggcaga atgggccatt gagaacccag cagccttcac tgacaggact 480
atcctggagc taggcagtgg agctggcctt acaggcctgg caatttgcaa ggcatgctgc 540
cccagagcat acatcttcag cgactgtcat gcccaagtgc ttgagcagct ccgtggaaac 600
gttctcctca acggcttctc cttagagccg cacacccccca ttgacgcagg cagctcgaag 660
gtgacagtgg ctcagctgga ctgggacgag gtgacagcct ctcagctctc tgccttccag 720
gcagatgttg tcattgcagc agatgtactg tactgctggg agatgacact gtcactggtc 780
agggtcctga agatgctcga ggactgccag aggaagagcg ctcctgatgt ctatgtagcc 840
tatactatcc gcagccagga cacaggcaag ctgttcatcg aagagctgga ccgtgctgga 900
atctactggg aagaggtgcc ccctcacact ggcaaactgt tcccttacga agagcattca 960
gccatcgtaa tcctgaagct ggtgctgacc agtcgccatg gtgtttga 1008

<210> SEQ ID NO 48
<211> LENGTH: 3791
<212> TYPE: DNA
<213> ORGANISM: Artificial Sequence
<220> FEATURE:
<223> OTHER INFORMATION: pCMV Myc vector

<400> SEQUENCE: 48
gagttcgagc ttgcatgcct gcaggtcgtt acataactta cggtaaatgg cccgcctggc 60
tgaccgccca acgacccccg cccattgacg tcaataatga cgtatgttcc catagtaacg 120
ccaataggga ctttccattg acgtcaatgg gtggagtatt tacggtaaac tgcccacttg 180
gcagtacatc aagtgtatca tatgccaagt acgcccccta ttgacgtcaa tgacggtaaa 240
tggcccgcct ggcattatgc ccagtacatg accttatggg actttcctac ttggcagtac 300
atctacgtat tagtcatcgc tattaccatg gtgatgcggt tttggcagta catcaatggg 360
cgtggatagc ggtttgactc acggggattt ccaagtctcc accccattga cgtcaatggg 420
agtttgtttt ggcaccaaaa tcaacgggac tttccaaaat gtcgtaacaa ctccgcccca 480
ttgacgcaaa tgggcggtag gcgtgtacgg tgggaggtct atataagcag agctcgttta 540
gtgaaccgtc agatcgcctg gagacgccat ccacgctgtt ttgacctcca tagaagacac 600
cgggaccgat ccagcctccg gactctagag gatccggtac tagaggaact gaaaaaccag 660
aaagttaact ggtaagttta gtctttttgt cttttatttc aggtcccgga tccggtggtg 720
gtgcaaatca aagaactgct cctcagtgga tgttgccttt acttctaggc ctgtacggaa 780
gtgttacttc tgctctaaaa gctgcggaat tgtacccgcg ggcccaccat ggcatcaatg 840

-continued

```
cagaagctga tctcagagga ggacctgctt atggccatgg aggcccgaat tcggtcgacc    900
gagatctctc gaggtaccgc ggccgcgggg atccagacat gataagatac attgatgagt    960
ttggacaaac cacaactaga atgcagtgaa aaaaatgctt tatttgtgaa atttgtgatg   1020
ctattgcttt atttgtaacc attataagct gcaataaaca agttaacaac aacaattgca   1080
ttcattttat gtttcaggtt cagggggagg tgtgggaggt tttttcggat cctctagagt   1140
cgatctgcag gcatgctagc ttggcgtaat catggtcata gctgtttcct gtgtgaaatt   1200
gttatccgct cacaattcca cacaacatac gagccggaag cataaagtgt aaagcctggg   1260
gtgcctaatg agtgagctaa ctcacattaa ttgcgttgcg ctcactgccc gctttccagt   1320
cgggaaacct gtcgtgccag ctgcattaat gaatcggcca acgcgcgggg agaggcggtt   1380
tgcgtattgg gcgctcttcc gcttcctcgc tcactgactc gctgcgctcg gtcgttcggc   1440
tgcggcgagc ggtatcagct cactcaaagg cggtaatacg gttatccaca gaatcagggg   1500
ataacgcagg aaagaacatg tgagcaaaag gccagcaaaa ggccaggaac cgtaaaaagg   1560
ccgcgttgct ggcgtttttc cataggctcc gcccccctga cgagcatcac aaaaatcgac   1620
gctcaagtca gaggtggcga aacccgacag gactataaag ataccaggcg tttccccctg   1680
gaagctccct cgtgcgctct cctgttccga ccctgccgct taccggatac ctgtccgcct   1740
ttctcccttc gggaagcgtg gcgctttctc atagctcacg ctgtaggtat ctcagttcgg   1800
tgtaggtcgt tcgctccaag ctgggctgtg tgcacgaacc ccccgttcag cccgaccgct   1860
gcgccttatc cggtaactat cgtcttgagt ccaacccggt aagacacgac ttatcgccac   1920
tggcagcagc cactggtaac aggattagca gagcgaggta tgtaggcggt gctacagagt   1980
tcttgaagtg gtggcctaac tacggctaca ctagaagaac agtatttggt atctgcgctc   2040
tgctgaagcc agttaccttc ggaaaaagag ttggtagctc ttgatccggc aaacaaacca   2100
ccgctggtag cggtggtttt tttgtttgca agcagcagat tacgcgcaga aaaaaaggat   2160
ctcaagaaga tcctttgatc ttttctacgg ggtctgacgc tcagtggaac gaaaactcac   2220
gttaagggat tttggtcatg agattatcaa aaaggatctt cacctagatc cttttaaatt   2280
aaaaatgaag ttttaaatca atctaaagta tatatgagta aacttggtct gacagttacc   2340
aatgcttaat cagtgaggca cctatctcag cgatctgtct atttcgttca tccatagttg   2400
cctgactccc cgtcgtgtag ataactacga tacgggaggg cttaccatct ggccccagtg   2460
ctgcaatgat accgcgagac ccacgctcac cggctccaga tttatcagca ataaaccagc   2520
cagccggaag ggccgagcgc agaagtggtc ctgcaacttt atccgcctcc atccagtcta   2580
ttaattgttg ccgggaagct agagtaagta gttcgccagt taatagtttg cgcaacgttg   2640
ttgccattgc tacaggcatc gtggtgtcac gctcgtcgtt tggtatggct tcattcagct   2700
ccggttccca acgatcaagg cgagttacat gatcccccat gttgtgcaaa aaagcggtta   2760
gctccttcgg tcctccgatc gttgtcagaa gtaagttggc cgcagtgtta tcactcatgg   2820
ttatggcagc actgcataat tctcttactg tcatgccatc cgtaagatgc ttttctgtga   2880
ctggtgagta ctcaaccaag tcattctgag aatagtgtat gcggcgaccg agttgctctt   2940
gcccggcgtc aatacgggat aataccgcgc cacatagcag aactttaaaa gtgctcatca   3000
ttggaaaacg ttcttcgggg cgaaaactct caaggatctt accgctgttg agatccagtt   3060
cgatgtaacc cactcgtgca cccaactgat cttcagcatc ttttactttc accagcgttt   3120
ctgggtgagc aaaaacagga aggcaaaatg ccgcaaaaaa gggaataagg gcgacacgga   3180
aatgttgaat actcatactc ttcctttttc aatattattg aagcatttat cagggttatt   3240
```

-continued

```
gtctcatgag cggatacata tttgaatgta tttagaaaaa taaacaaata ggggttccgc   3300

gcacatttcc ccgaaaagtg ccacctgacg tctaagaaac cattattatc atgacattaa   3360

cctataaaaa taggcgtatc acgaggccct ttcgtctcgc gcgtttcggt gatgacggtg   3420

aaaacctctg acacatgcag ctcccggaga cggtcacagc ttgtctgtaa gcggatgccg   3480

ggagcagaca agcccgtcag ggcgcgtcag cgggtgttgg cgggtgtcgg ggctggctta   3540

actatgcggc atcagagcag attgtactga gagtgcacca tatgcggtgt gaaataccgc   3600

acagatgcgt aaggagaaaa taccgcatca ggcgccattc gccattcagg ctgcgcaact   3660

gttgggaagg gcgatcggtg cgggcctctt cgctattacg ccagctggcg aaagggggat   3720

gtgctgcaag gcgattaagt tgggtaacgc cagggttttc ccagtcacga cgttgtaaaa   3780

cgacggccag t                                                        3791
```